US010301338B2

(12) United States Patent
Chen

(10) Patent No.: US 10,301,338 B2
(45) Date of Patent: *May 28, 2019

(54) ORGANIC ELECTROLUMINESCENT MATERIALS AND DEVICES

(71) Applicant: Universal Display Corporation, Ewing, NJ (US)

(72) Inventor: Hsiao-Fan Chen, Taipei (TW)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/948,031

(22) Filed: Apr. 9, 2018

(65) Prior Publication Data
US 2018/0282357 A1    Oct. 4, 2018

Related U.S. Application Data

(63) Continuation-in-part of application No. 15/825,798, filed on Nov. 29, 2017, and a continuation-in-part of application No. 15/399,724, filed on Jan. 5, 2017, and a continuation-in-part of application No. 14/933,684, filed on Nov. 5, 2015, said application No. 15/399,724 is a continuation-in-part of application No. 14/933,684, which is a continuation-in-part of application No. PCT/US2015/029269, filed on May 5, 2015.

(60) Provisional application No. 62/488,406, filed on Apr. 21, 2017, provisional application No. 62/488,107, filed on Apr. 21, 2017, provisional application No. 62/082,970, filed on Nov. 21, 2014, provisional application No. 61/990,239, filed on May 8, 2014.

(51) Int. Cl.
| | | |
|---|---|---|
| H01L 51/54 | (2006.01) |
| C09K 11/06 | (2006.01) |
| C07F 15/00 | (2006.01) |
| H01L 51/00 | (2006.01) |
| H01L 51/50 | (2006.01) |
| C07D 471/16 | (2006.01) |

(52) U.S. Cl.
CPC ........ *C07F 15/0086* (2013.01); *C07D 471/16* (2013.01); *C07F 15/006* (2013.01); *H01L 51/0087* (2013.01); *H01L 51/5016* (2013.01); *H01L 51/5056* (2013.01); *H01L 51/5072* (2013.01); *H01L 51/5024* (2013.01); *H01L 51/5036* (2013.01)

(58) Field of Classification Search
CPC ... C09K 11/06; C09K 11/025; C09K 2211/00; C09K 2211/10; C09K 2211/1007; C09K 2211/1011; C09K 2211/1022; C09K 2211/1044; C09K 2211/1088; C09K 2211/185; C07D 471/16; C07D 498/16; C07D 513/16; C07F 7/00; C07F 7/1852; C07F 15/00; C07F 15/0033; C07F 15/0086; H01L 27/32; H01L 51/0032; H01L 51/005; H01L 51/0071; H01L 51/0072; H01L 51/0073; H01L 51/0074; H01L 51/0085; H01L 51/0087; H01L 51/0086; H01L 51/50; H01L 51/5012; H01L 51/5016; H01L 51/5206; H01L 51/5221
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Andrew K Bohaty
(74) *Attorney, Agent, or Firm* — Duane Morris LLP

(57) ABSTRACT

Tetradentate ligand based on strapped phenenthradine-imidazole (SIP) based Pt or Pd complexes useful as emitters in PHOLEDs is disclosed.

19 Claims, 2 Drawing Sheets

(56) References Cited

U.S. PATENT DOCUMENTS

| | | | |
|---|---|---|---|
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2004/0247933 A1 | 12/2004 | Thoms | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0082284 A1 | 4/2007 | Stoessel et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2012/0223276 A1 | 9/2012 | Parham et al. | |
| 2012/0223634 A1* | 9/2012 | Xia ............... | C09K 11/06 313/504 |
| 2012/0292607 A1 | 11/2012 | Watanabe et al. | |
| 2013/0168656 A1 | 7/2013 | Tsai et al. | |
| 2014/0014306 A1 | 1/2014 | Hirose et al. | |
| 2014/0110642 A1 | 4/2014 | Stoessel et al. | |
| 2014/0364605 A1 | 12/2014 | Li et al. | |
| 2015/0194616 A1 | 7/2015 | Li et al. | |
| 2015/0207086 A1 | 7/2015 | Li et al. | |
| 2016/0072082 A1 | 3/2016 | Brooks et al. | |
| 2017/0162802 A1 | 6/2017 | Weaver et al. | |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2012-004529 | 1/2012 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2008/156879 | 12/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2015/171627 | 11/2015 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiciiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

(56) References Cited

OTHER PUBLICATIONS

Huang, Jinsong et al., "Highly Efficient Red-Emission Polymer Phosphorescent Light-Emitting Diodes Based on Two Novel Tris(1-phenylisoquinolinato-C2,N)indium(III) Derivatives," Adv. Mater, 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater, 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylbory1)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(1) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
International Search Report issued in connection with corresponding International patent application No. PCT/US15/29269, dated Jul. 24, 2015, 2 pages.
International Preliminary Report on Patentability issued in connection with International patent application No. PCT/US15/29269, dated Nov. 8, 2016, 10 pages.
Extended European Search Report dated Aug. 31, 2016 for corresponding European Application No. 16001000.5.
Notice of Reasons for Rejection dated Jul. 3, 2018 for corresponding Japanese Patent Application No. 2016-567017.
Li, G.uijie et al. "Modifying Emission Spectral Bandwidth of Phosphorescent Platinum(II) Complexes Through Synthetio Control" Inorg. Chem. 2017, 56, pp. 8244-8256.
Fleetham, Tyler et al., "Effi cient "Pure" Blue OLEDs Employing Tetradentate Pt Complexes with a Narrow Spectral Bandwidth" Adv. Mater. 2014, 26, pp. 7116-7121.
Zhu, Zhi-Qiang et al., "Efficient Cyclometalated Platinum(II) Complex with Superior Operational Stability" Adv. Mater. 2017, 29, 1605002, pp. 1-5.
Fleetham, Tyler B. et al. "Tetradentate Pt(II) Complexes with 6-Membered Chelate Rings: A New Route for Stable and Efficient Blue Organic Light Emitting Diodes" Chem. Mater. 2016, 28, pp. 3276-3282.
Fleetham, Tyler et al. "Efficient and stable single-doped white OLEDs using a palladium-based phosphorescent excimer†" Chem. Sci., 2017, 8, pp. 7983-7990.

* cited by examiner

ORGANIC ELECTROLUMINESCENT MATERIALS AND DEVICES

CROSS-REFERENCE TO RELATED APPLICATIONS

This application is a continuation-in-part application of U.S. patent application Ser. No. 15/825,798, filed Nov. 29, 2017, and U.S. patent application Ser. No. 15/399,724, filed Jan. 5, 2017, both of which are continuation-in-part applications of U.S. patent application Ser. No. 14/933,684, filed Nov. 5, 2015, which is a continuation-in-part application of International Application No. PCT/US2015/0029269, filed May 5, 2015, which claims priority to U.S. Provisional Application No. 62/082,970, filed Nov. 21, 2014, and U.S. Provisional Application No. 61/990,239, filed May 8, 2014, the entire contents of which are incorporated herein by reference. This application also claims priority under 35 U.S.C. § 119(e) to U.S. provisional Application No. 62/488,107, filed Apr. 21, 2017, and U.S. provisional Application No. 62/488,406, filed Apr. 21, 2017, the entire contents of which are incorporated herein by reference.

FIELD

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

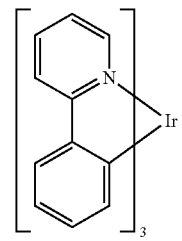

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

A compound having the formula:

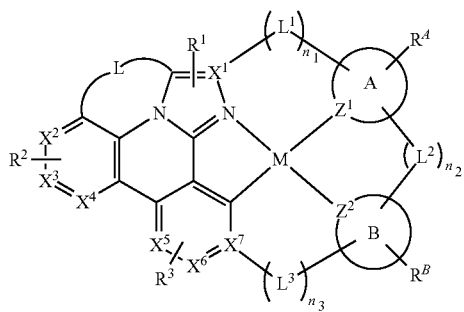

Formula I is disclosed. In Formula I, rings A and B are each independently a 5- or 6-membered carbocyclic or heterocyclic ring. At least one of the rings A and B is a 5-membered carbocyclic or heterocyclic ring. $Z^1$, $Z^2$, $X^1$ to $X^7$ are each independently selected from the group consisting of carbon and nitrogen. Each of $R^1$, $R^2$, $R^3$, $R^A$ and $R^B$ independently represents none to a maximum possible number of substitutions. Each of $R^1$, $R^2$, $R^3$, $R^A$ and $R^B$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any two substitutions in $R^1$, $R^2$, $R^3$, $R^A$ and $R^B$ are optionally joined or fused into a ring. Each of $n_1$, $n_2$, and $n_3$ is independently 0 or 1. When $n_1$, $n_2$ or $n_3$ is 1, each of the respective $L^1$, $L^2$, or $L^3$ is independently selected from the group consisting of a direct bond, BR, NR, PR, O, S, Se, C=O, S=O, $SO_2$, CRR', SiRR', GeRR', alkyl, cycloalkyl, and combinations thereof, wherein R and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. When $n_1$, $n_2$ or $n_3$ is 0, the respective $L^1$, $L^2$, or $L^3$ is not present. The value of $n_1+n_2+n_3$ is at least 2. When $L^1$ is present, $X^1$ is carbon. When $L^3$ is present, $X^7$ is carbon. L is a linking group having two to three linking atoms, wherein the linking atoms are each independently selected from the group consisting of C, Si, O, S, N, B or combinations thereof. M is Pt or Pd.

An organic light emitting device (OLED) comprising an anode, a cathode, and an organic layer, disposed between the anode and the cathode, where the organic layer comprises a compound having the formula:

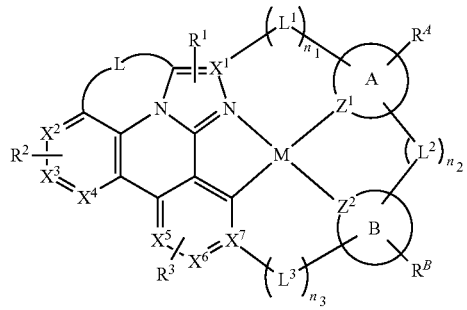

Formula I is also disclosed. In Formula I, rings A and B are each independently a 5- or 6-membered carbocyclic or heterocyclic ring. At least one of rings A and B is a 5-membered carbocyclic or heterocyclic ring. $Z^1$, $Z^2$, $X^1$ to $X^7$ are each independently selected from the group consisting of carbon and nitrogen. Each of $R^1$, $R^2$, $R^3$, $R^A$ and $R^B$ independently represents none to a maximum possible number of substitutions. $R^1$, $R^2$, $R^3$, $R^A$ and $R^B$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any two substitutions in $R^1$, $R^2$, $R^3$, $R^A$ and $R^B$ are optionally joined or fused into a ring. Each of $n_1$, $n_2$, and $n_3$ is independently 0 or 1. When $n_1$, $n_2$ or $n_3$ is 1, each of the respective $L^1$, $L^2$, or $L^3$ is independently selected from the group consisting of a direct bond, BR, NR, PR, O, S, Se, C=O, S=O, $SO_2$, CRR', SiRR', GeRR', alkyl, cycloalkyl, and combinations thereof, wherein R and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. When $n_1$, $n_2$ or $n_3$ is 0, the respective $L^1$, $L^2$, or $L^3$ is not present. $n_1+n_2+n_3$ is at least 2. When $L^1$ is present, $X^1$ is carbon. When $L^3$ is present, $X^7$ is carbon. L is a linking group having two to three linking atoms, wherein the linking atoms are each independently selected from the group consisting of C, Si, O, S, N, B or combinations thereof. M is Pt or Pd.

A consumer product comprising the OLED is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
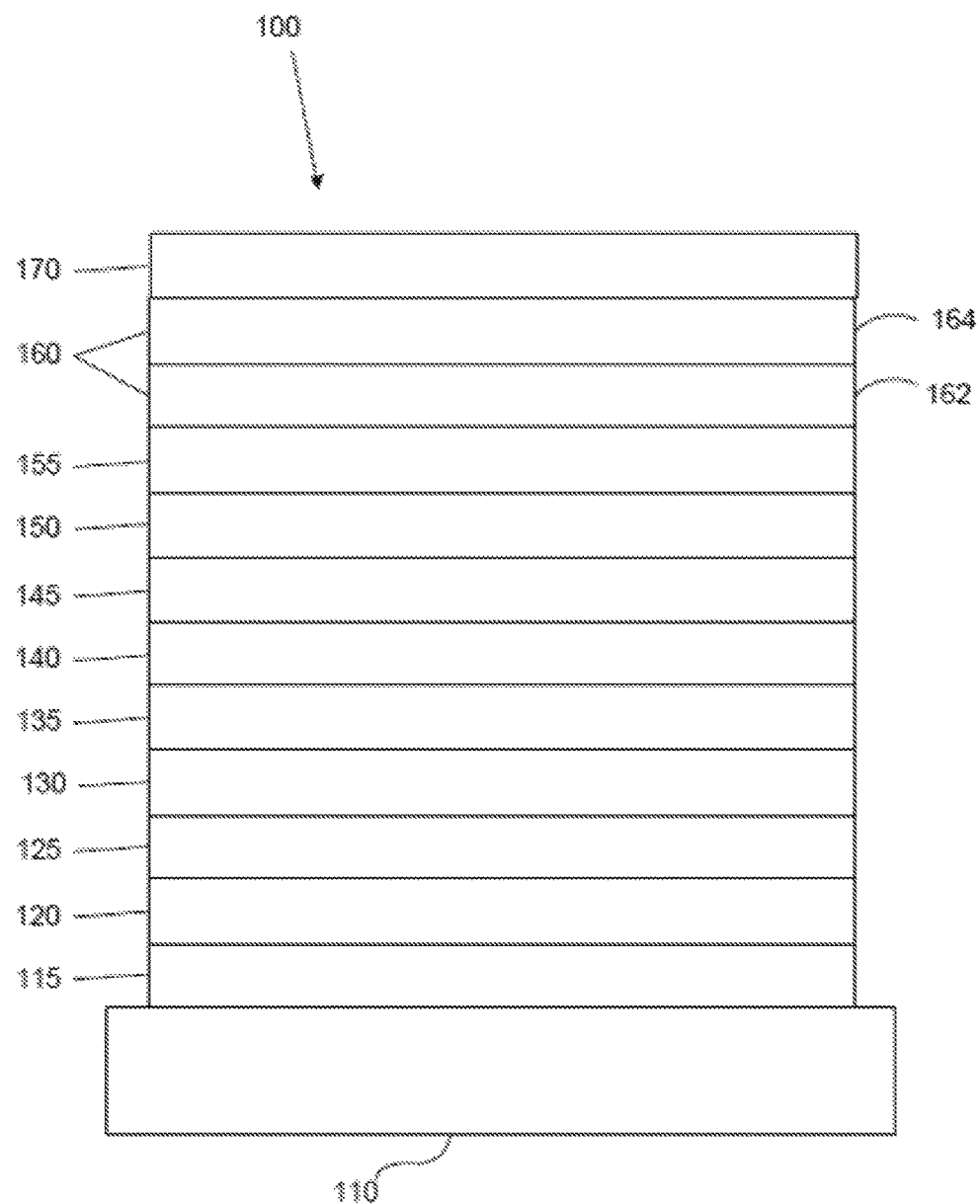
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
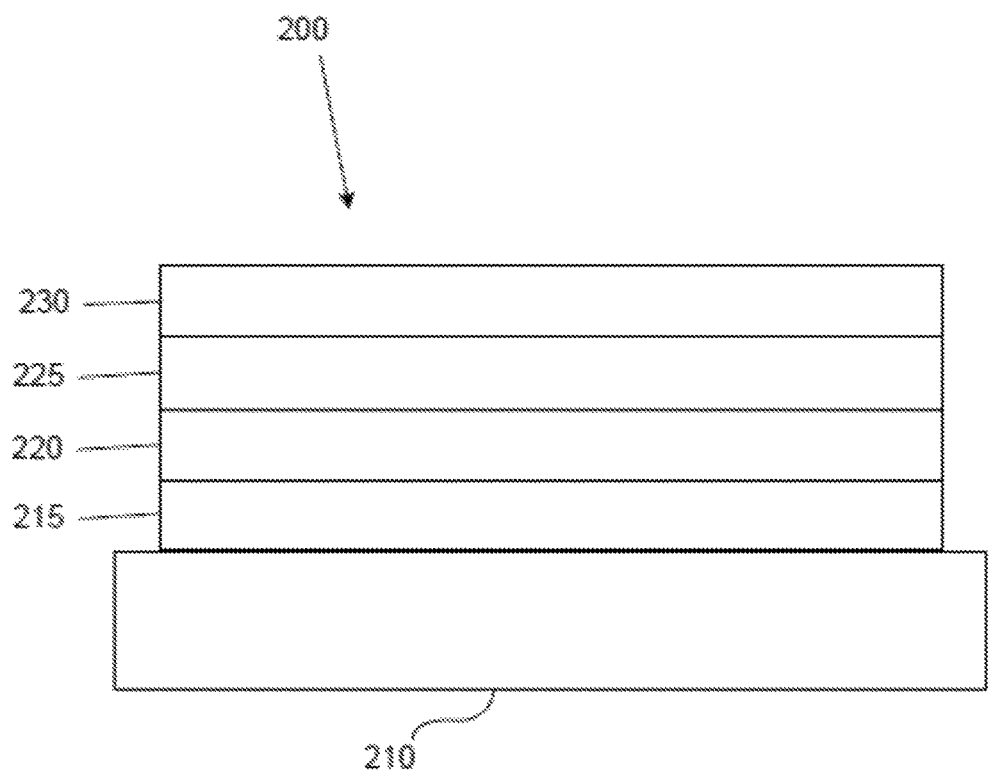
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, mobile phones, tablets, phablets, personal digital assistants (PDAs), wearable devices, laptop computers, digital cameras, camcorders, viewfinders, microdisplays (displays that are less than 2 inches diagonal), 3-D displays, virtual reality or augmented reality displays, vehicles, video walls comprising multiple displays tiled together, theater or stadium screen, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions. The maximum number of substitutions possible in a structure will depend on the number of atoms with available valencies.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

A compound having the formula:

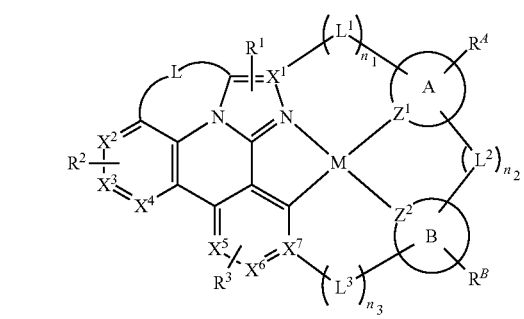

Formula I is disclosed. In Formula I, rings A and B are each independently a 5- or 6-membered carbocyclic or heterocyclic ring. At least one of the rings A and B is a 5-membered carbocyclic or heterocyclic ring. $Z^1$, $Z^2$, $X^1$ to $X^7$ are each independently selected from the group consisting of carbon and nitrogen. Each of $R^1$, $R^2$, $R^3$, $R^A$ and $R^B$ independently represents none to a maximum possible number of substitutions. Each of $R^1$, $R^2$, $R^3$, $R^A$ and $R^B$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any two substitutions in $R^1$, $R^2$, $R^3$, $R^A$ and $R^B$ are optionally joined or fused into a ring. Each of $n_1$, $n_2$, and $n_3$ is independently 0 or 1. When $n_1$, $n_2$ or $n_3$ is 1, each of the respective $L^1$, $L^2$, or $L^3$ is independently selected from the group consisting of a direct bond, BR, NR, PR, O, S, Se, C=O, S=O, SO$_2$, CRR', SiRR', GeRR', alkyl, cycloalkyl, and combinations thereof, wherein R and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. When $n_1$, $n_2$ or $n_3$ is 0, the respective $L^1$, $L^2$, or $L^3$ is not present. The value of $n_1+n_2+n_3$ is at least 2. When $L^1$ is present, $X^1$ is carbon. When $L^3$ is present, $X^7$ is carbon. L is a linking group having two to three linking atoms, wherein the linking atoms are each independently selected from the group consisting of C, Si, O, S, N, B or combinations thereof. M is Pt or Pd.

Strapped phenanthridine-imidazole (SIP) as the emitting ligand for Ir and Pt organometallic complexes shows decent blue color and superior device lifetime. The photophysical properties of platinum complexes based on SIP is highly dependent on the ancillary part of the ligand, the ancillary part being the part containing the rings A and B. For example, high EQE devices can be achieved with the ancillary part consisting of a 5-membered ring moiety such as phenylpyrazole (ppz) and phenylisoimidazole. This includes different possible ancillary parts of the tetradentate ligand based on SIP for Pt or Pd complexes. The ancillary part plays an important role for photophysical properties as well as device performance. Specifically, when the A ring is a 5-membered ring which directly links to B (e.g., phenylpyrazole, phenylbenzimidazole, and phenylisoimidazole), high device EQE can be achieved.

In some embodiments of the compound, each of $R^1$, $R^2$, $R^3$, $R^A$, $R^B$, R and R' is independently selected from the group consisting of hydrogen, deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof.

In some embodiments of the compound, M is Pt.

In some embodiments of the compound, the linking atoms in L form at least one single aliphatic bond between two linking atoms.

In some embodiments of the compound, ring A is a 5-membered aromatic ring and ring B is a 6-membered aromatic ring. In some embodiments, ring A is a 6-membered aromatic ring and ring B is a 5-membered aromatic ring. In some embodiments, rings A and B are 5-membered aromatic rings.

In some embodiments of the compound, at least one of rings A and B is selected from the group consisting of imidazole, pyrazole, thiazole, oxazole, and derived carbene thereof.

In some embodiments of the compound, $X^1$ to $X^7$ are carbon. In some embodiments, at least one of $X^1$ to $X^7$ is nitrogen.

In some embodiments, one of $Z^1$ and $Z^2$ is nitrogen, and the other one of $Z^1$ and $Z^2$ is carbon. In some embodiments, one of $Z^1$ and $Z^2$ is neutral carbene carbon, and the other one of $Z^1$ and $Z^2$ is anionic carbon.

In some embodiments of the compound, $L^2$ is present and is a direct bond.

In some embodiments of the compound, $L^3$ is present and is O or NR.

In some embodiments, $n_1$ is 0, $n_2$ and $n_3$ is 1; in some embodiments, $n_1$ and $n_2$ is 1, and $n_3$ is 0.

In some embodiments, when $n_1$, $n_2$ or $n_3$ is 1, each of the respective $L^1$, $L^2$, or $L^3$ is independently selected from the group consisting of a direct bond, NR, O, S, CRR', SiRR', alkyl, cycloalkyl, and combinations thereof. In some embodiments of the compound, at least one pair of substituents in $R^A$, $L^2$, and $R^B$ are joined or fused into a ring.

In some embodiments of the compound, the linking group L is independently selected from the group consisting of —$CR^4R^5$—$CR^6R^7$—, —$CR^4R^5$—$CR^6R^7$—$CR^8R^9$—, —$CR^4R^5$—$NR^6$—, —$CR^4$=$CR^5$—$CR^6R^7$—, —O—$SiR^4R^5$—, —$CR^4R^5$—S—, —$CR^4R^5$—O—, and —C—$SiR^4R^5$—, wherein each $R^4$ to $R^9$ can be same or different, and are independently selected from the group consisting of hydrogen, deuterium, alkyl, cycloalkyl, aryl, heteroaryl, and combinations thereof; wherein any two of $R^4$ to $R^9$ are optionally joined or fused into a 5-membered or a 6-membered ring.

In some embodiments of the compound, the linking group L is selected from the group consisting of:

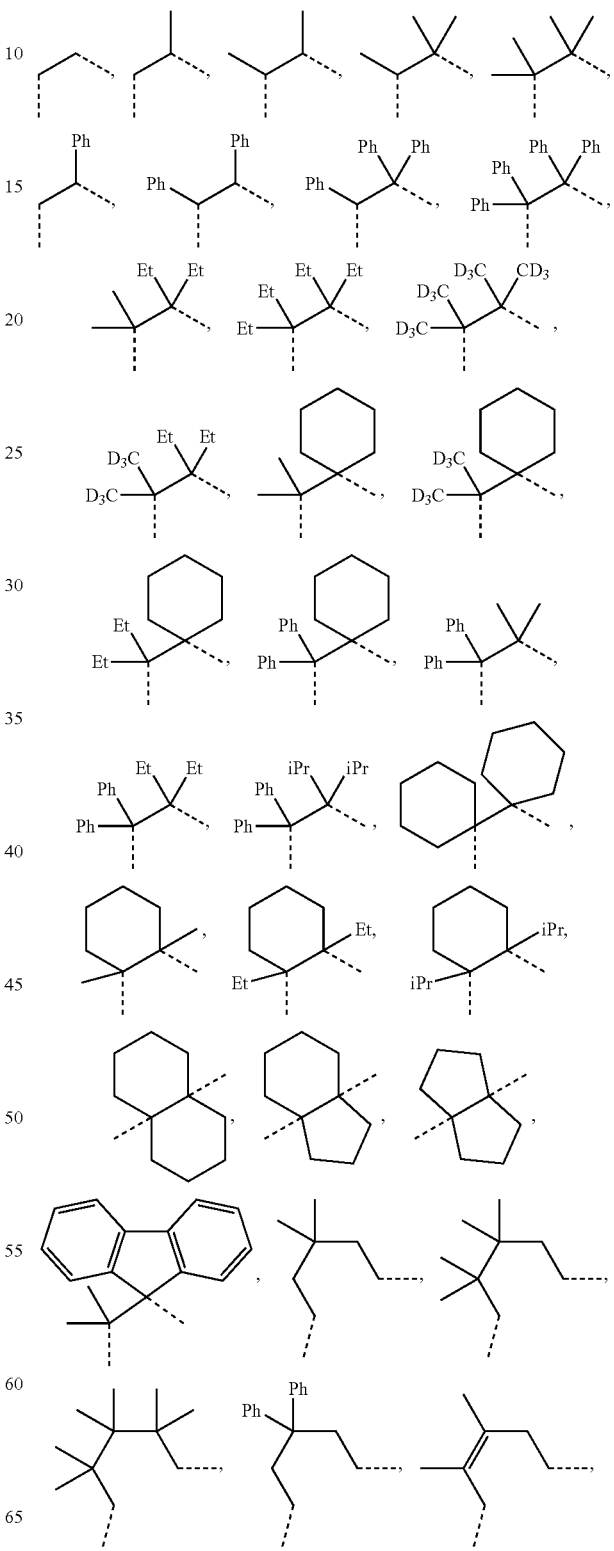

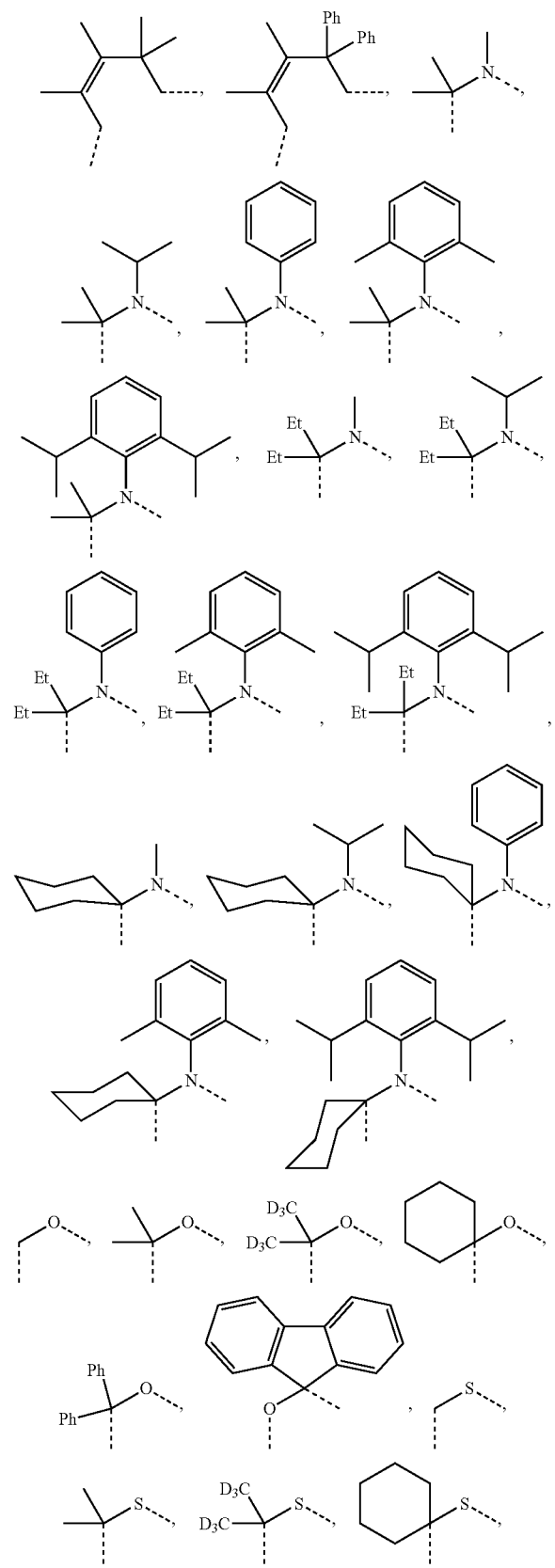
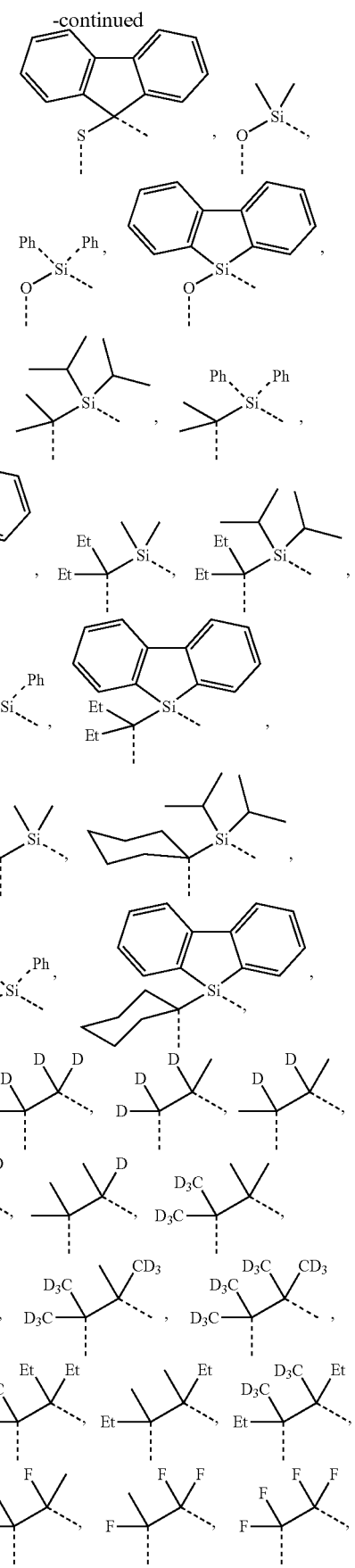

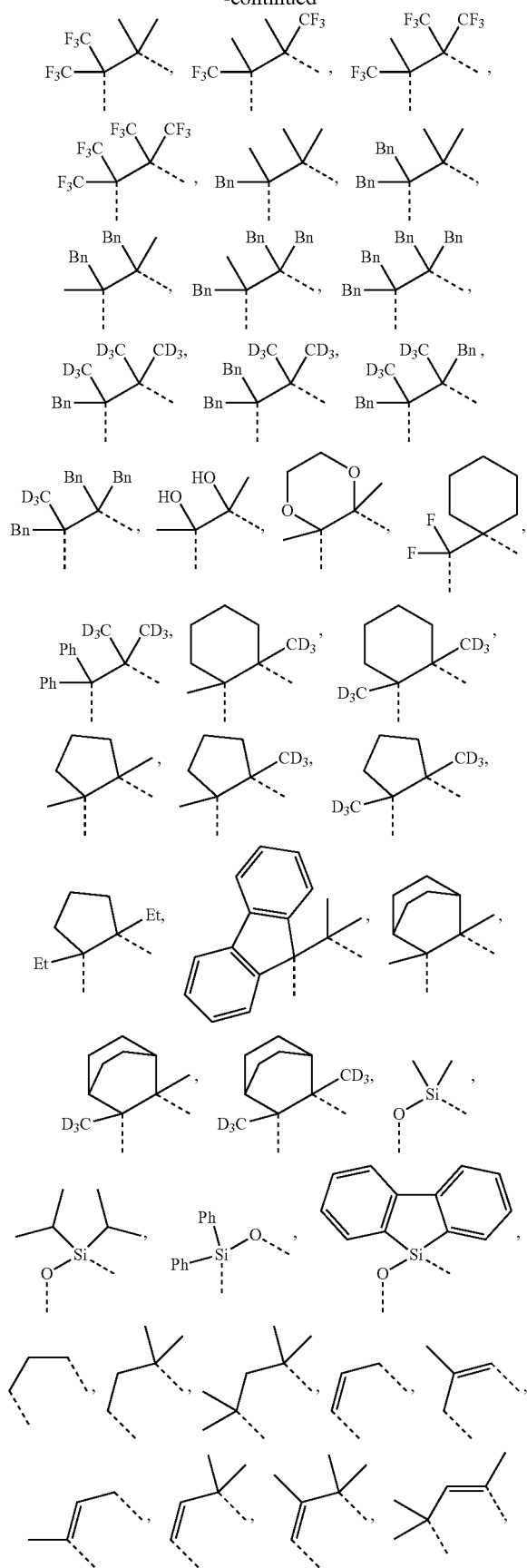
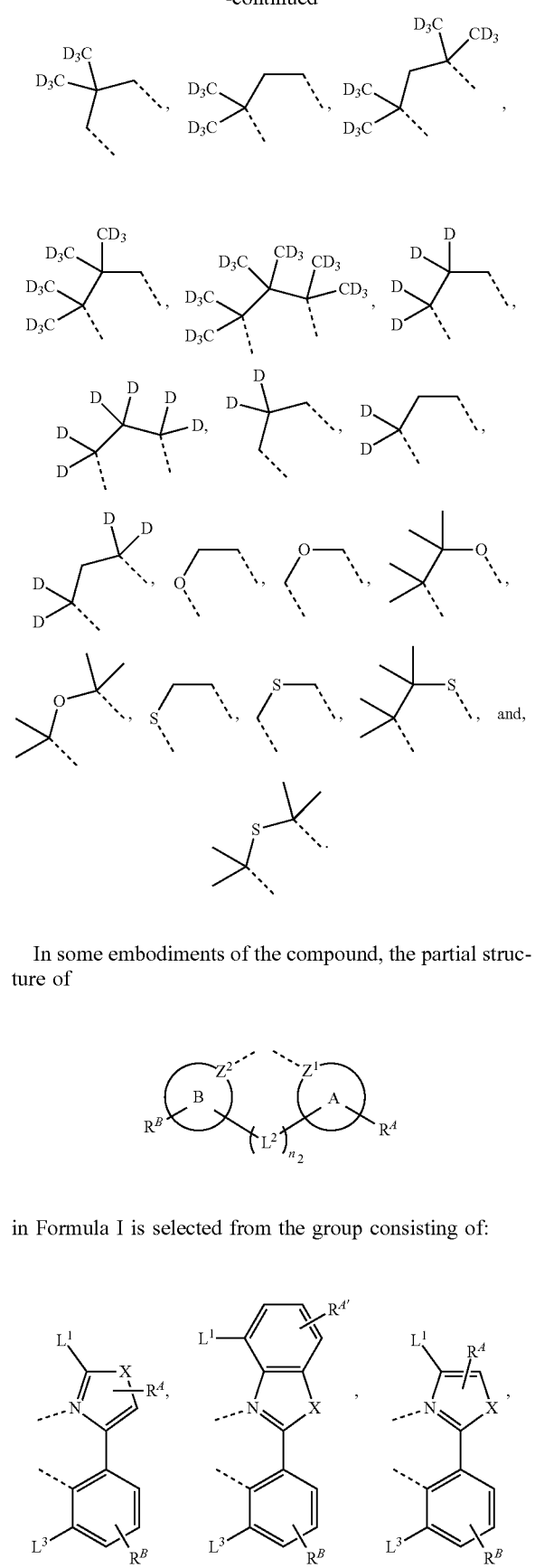
In some embodiments of the compound, the partial structure of
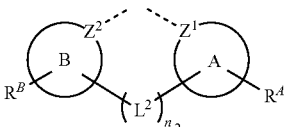
in Formula I is selected from the group consisting of:
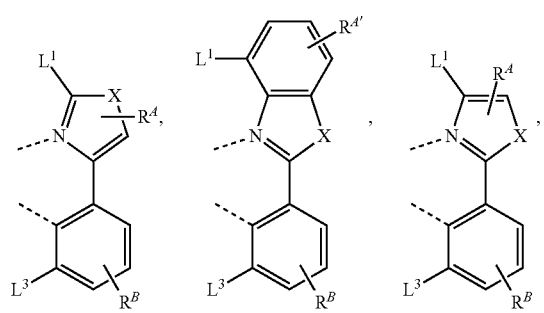

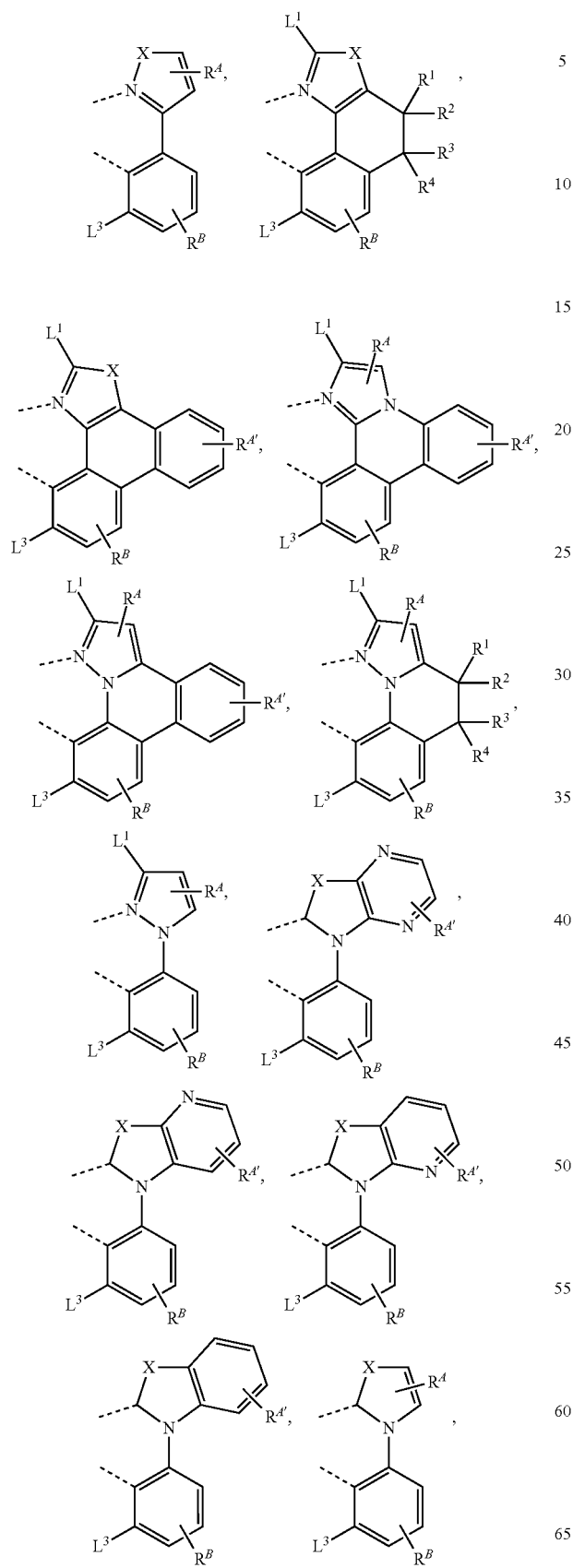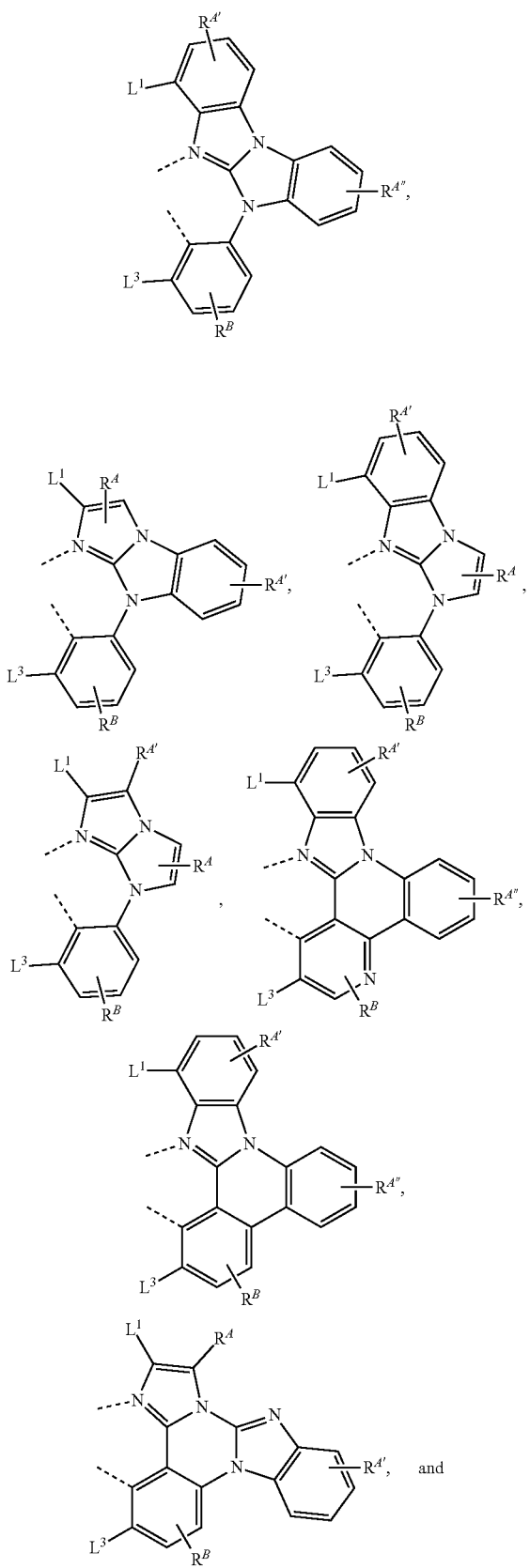

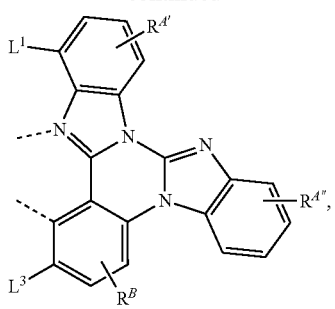

wherein X is one of O, S, NR', BR', CR'R", or SiR'R"; and wherein each of R⁴, R^{A'}, R^{A"}, and R" is independently selected from the group consisting of hydrogen, deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof.

In some embodiments of the compound, the compound is selected from group consisting of Compound x, wherein x is an integer defined by 44i+j−44, wherein i is an integer from 1 to 34, and j is an integer from 1 to 44; wherein each Compound x has a structure according to formula Pt(L_{Ai})(L_{Bj}); wherein L_{Ai} and L_{Bj} are based on the following formulas:

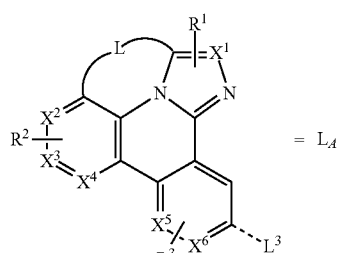 = L_A

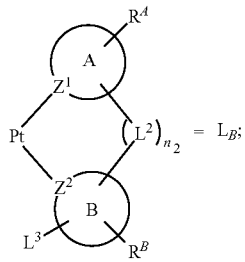 = L_B;

and have the following structures:

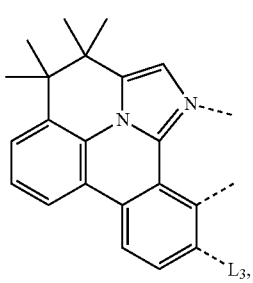 L_{A1}

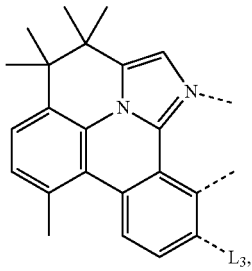 L_{A2}

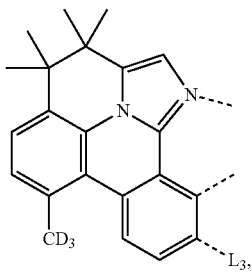 L_{A3}

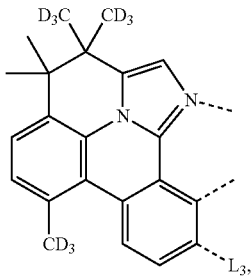 L_{A4}

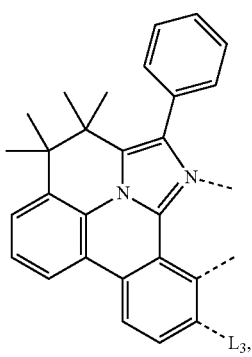 L_{A5}

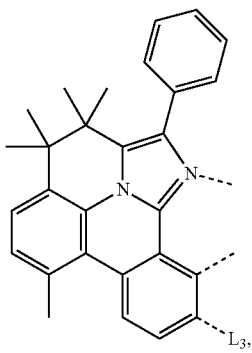 L_{A6}

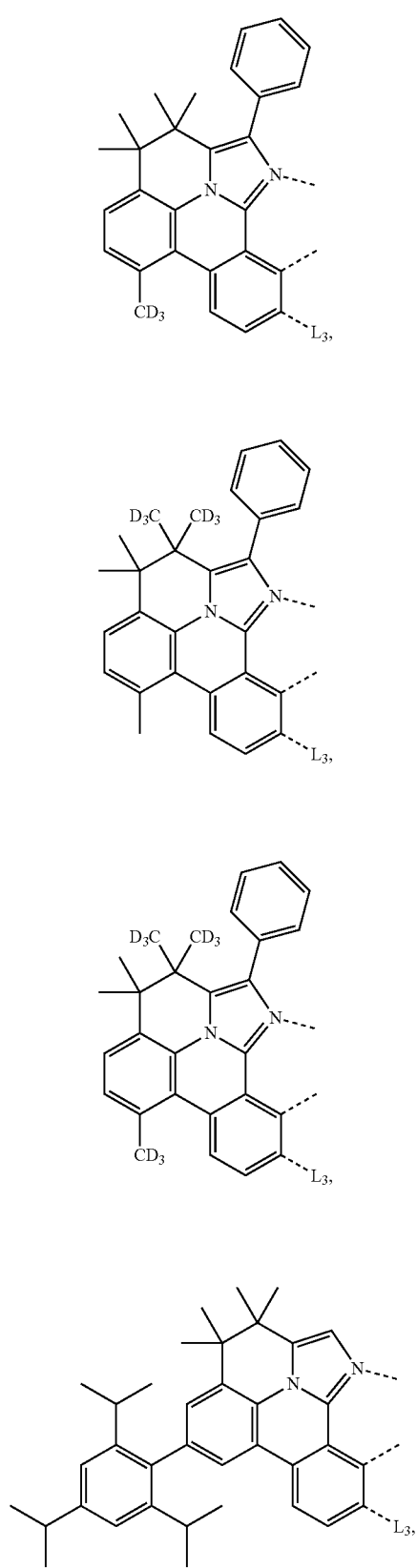
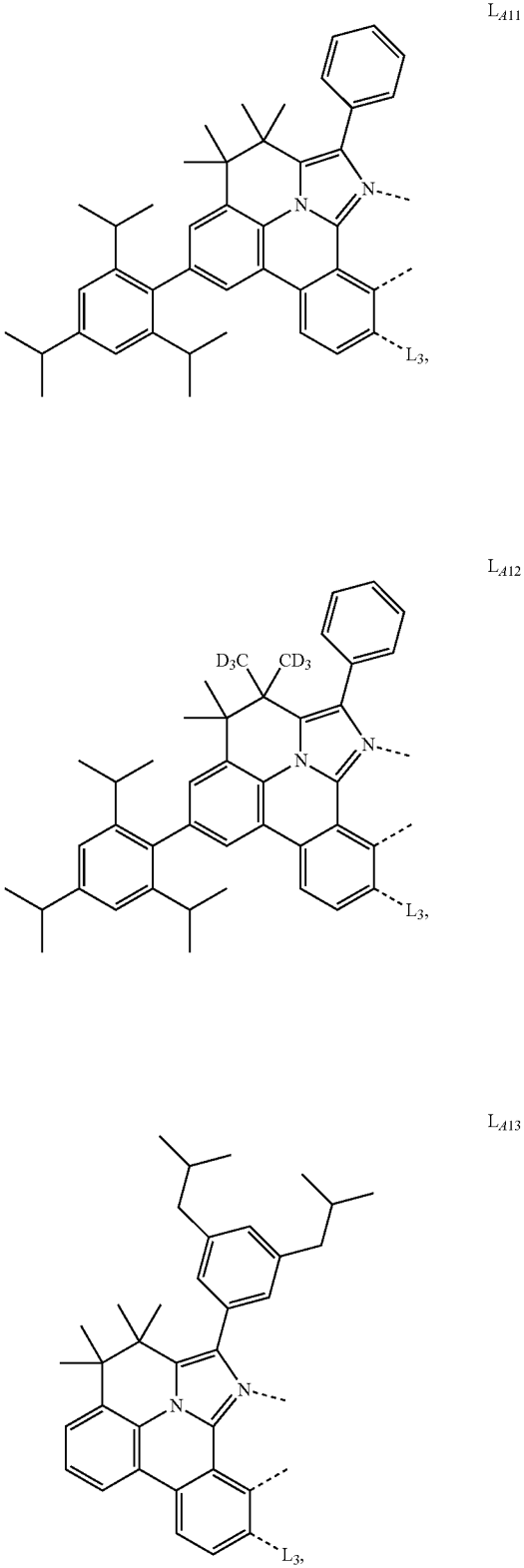

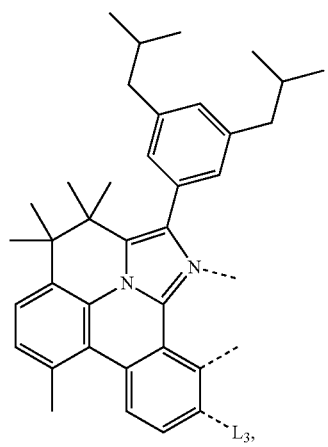
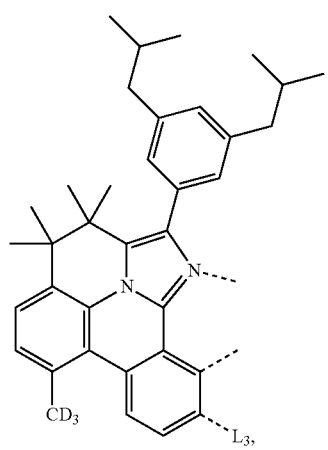
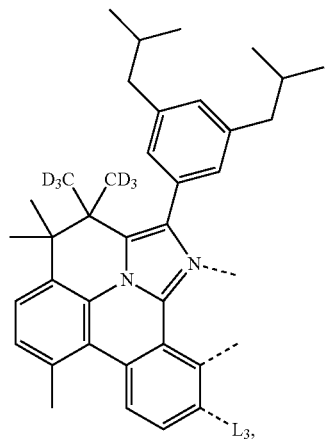
$L_{A14}$
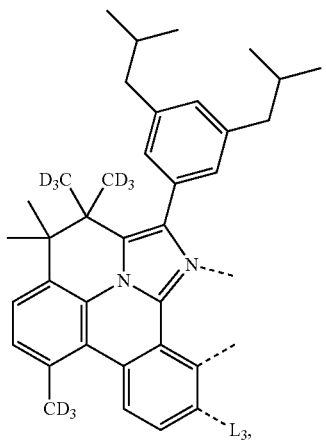
$L_{A15}$
$L_{A16}$
$L_{A17}$
$L_{A18}$
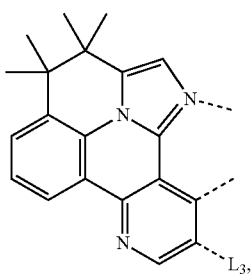
$L_{A19}$
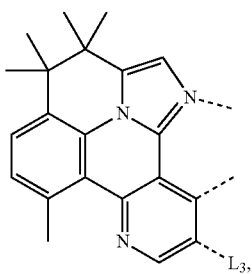
$L_{A20}$
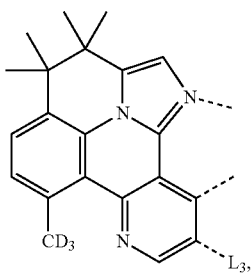
$L_{A21}$
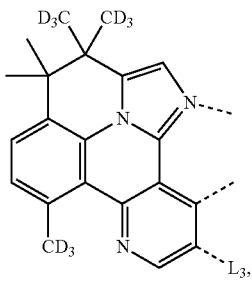

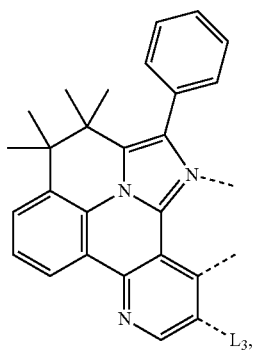
L<sub>A22</sub>
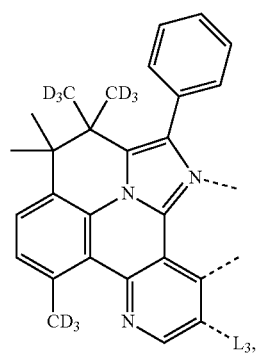
L<sub>A26</sub>
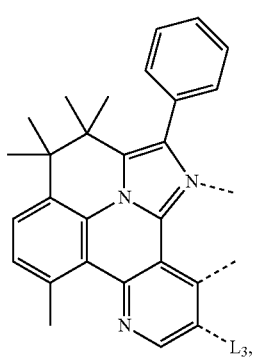
L<sub>A23</sub>
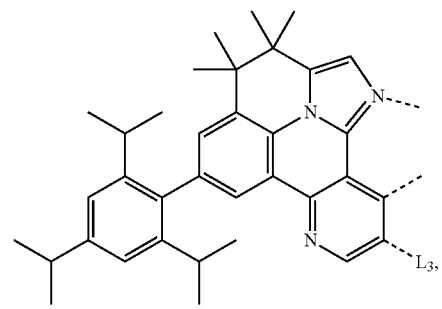
L<sub>A27</sub>
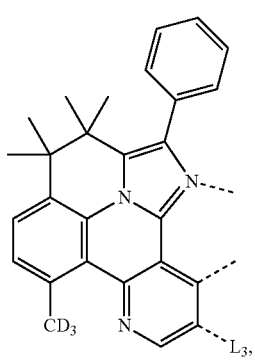
L<sub>A24</sub>
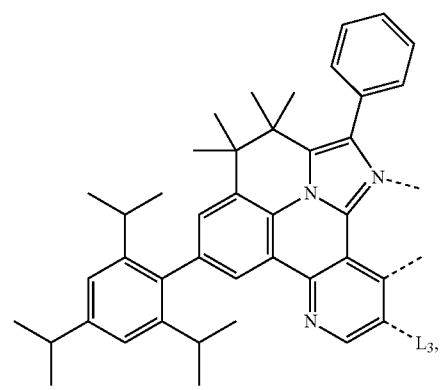
L<sub>A28</sub>
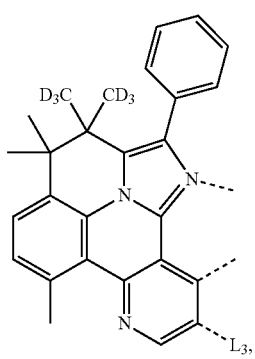
L<sub>A25</sub>
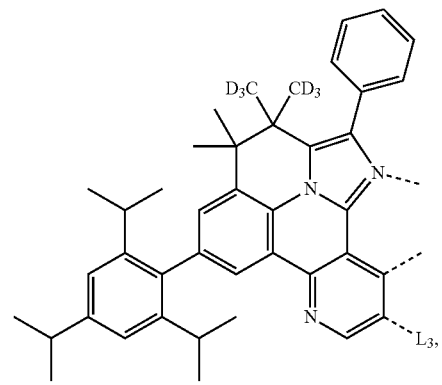
L<sub>A29</sub>

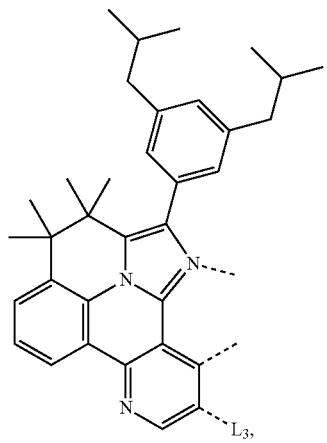
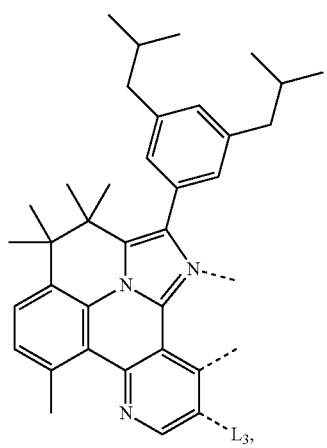
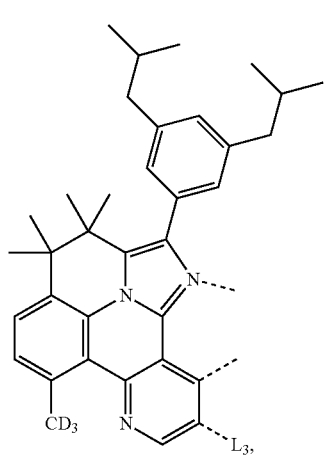
L_{A30}
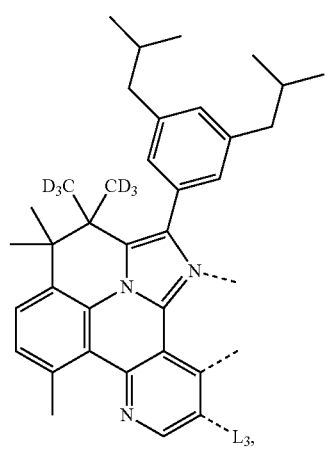
L_{A31}
L_{A32}
L_{A33}
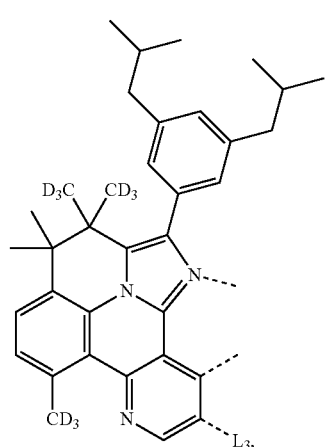
L_{A34}
L_{B1}
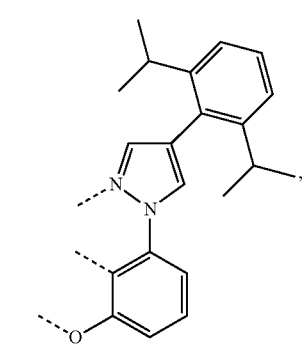
L_{B2}
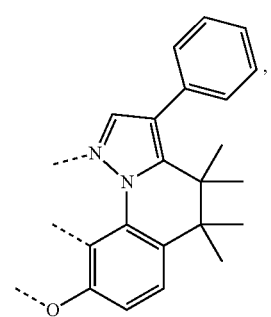

L_{B3} 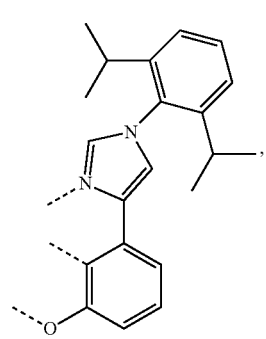
L_{B4} 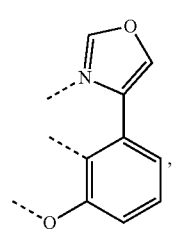
L_{B5} 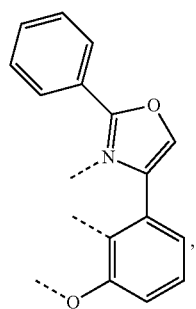
L_{B6} 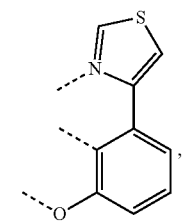
L_{B7} 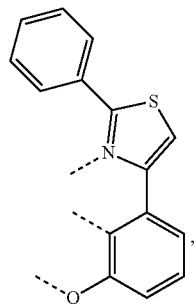
L_{B8} 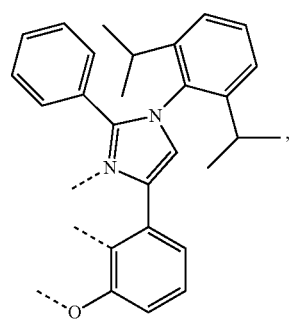
L_{B9} 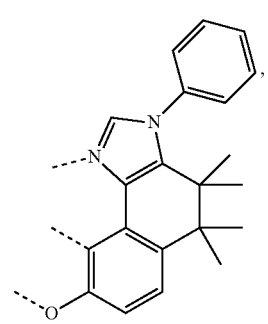
L_{B10} 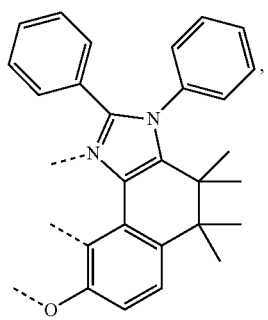
L_{B11} 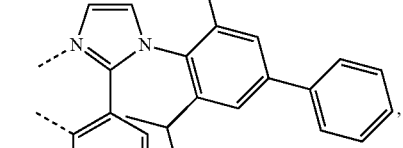
L_{B12} 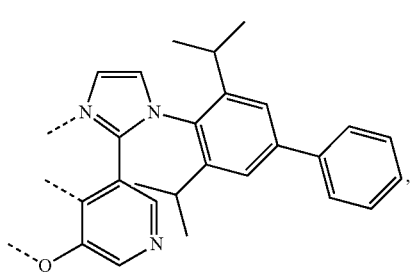

| | |
|---|---|
| 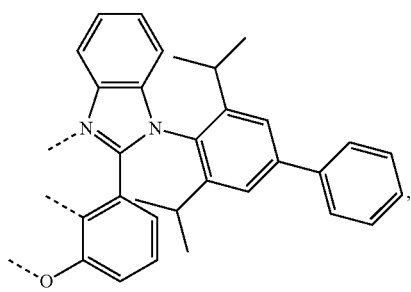 L$_{B13}$ | 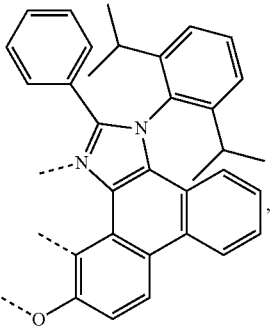 L$_{B18}$ |
| 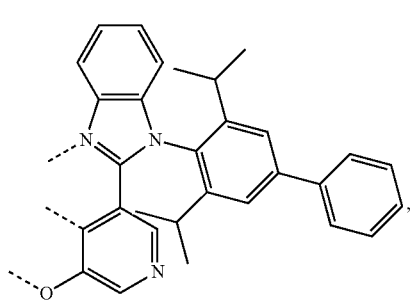 L$_{B14}$ | 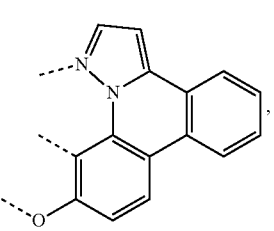 L$_{B19}$ |
| 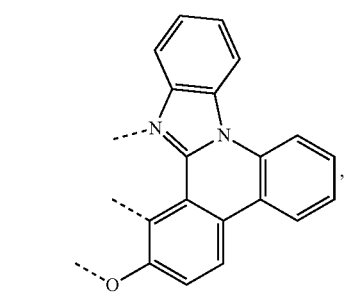 L$_{B15}$ | 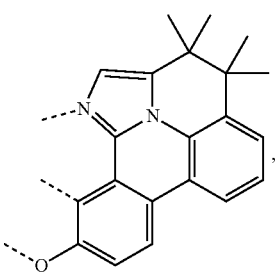 L$_{B20}$ |
| 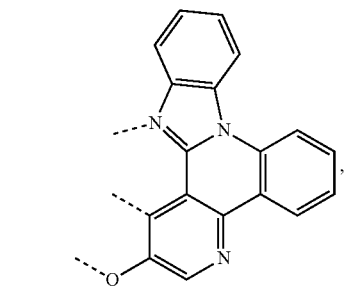 L$_{B16}$ | 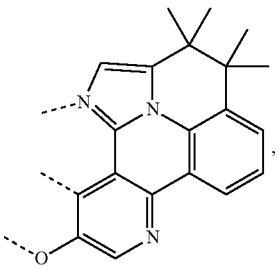 L$_{B21}$ |
| 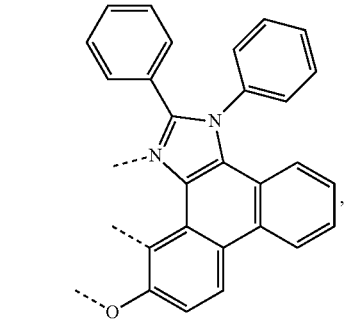 L$_{B17}$ | 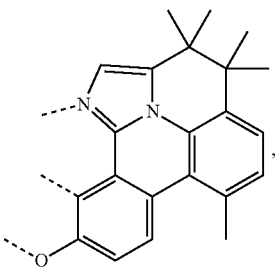 L$_{B22}$ |

$L_{B23}$
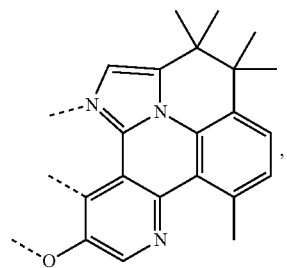
$L_{B24}$
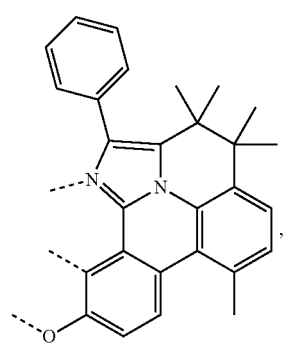
$L_{B25}$
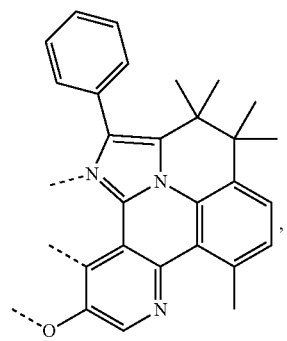
$L_{B26}$
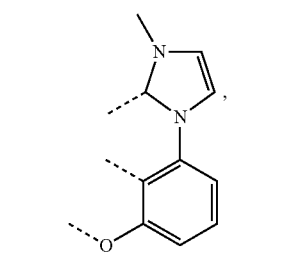
$L_{B27}$
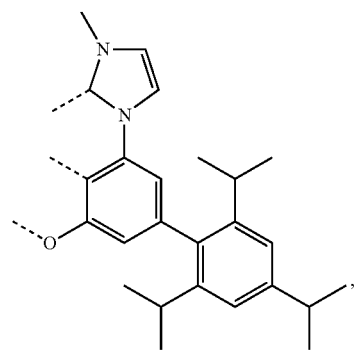
$L_{B28}$
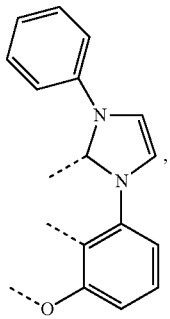
$L_{B29}$
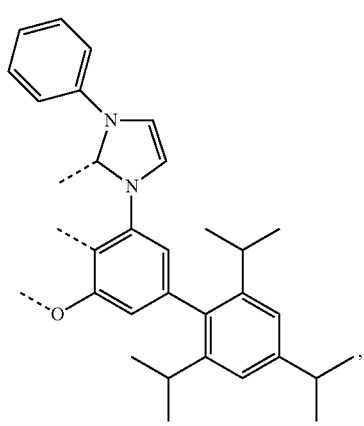
$L_{B30}$
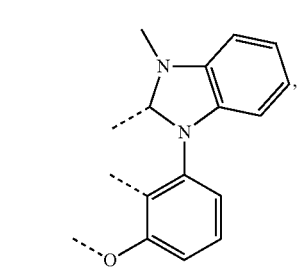
$L_{B31}$
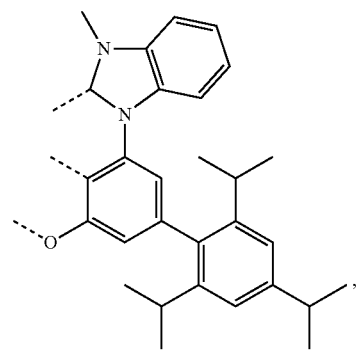

L<sub>B32</sub>
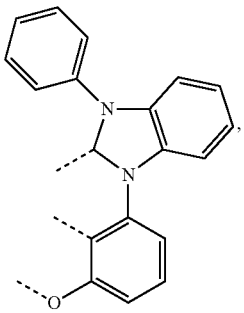
L<sub>B33</sub>
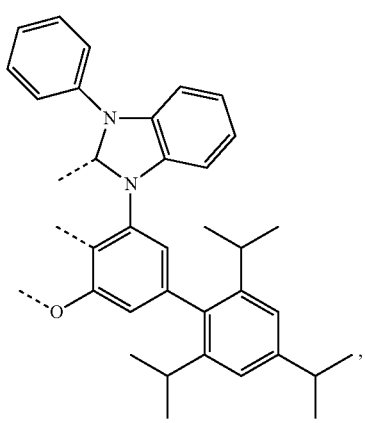
L<sub>B34</sub>
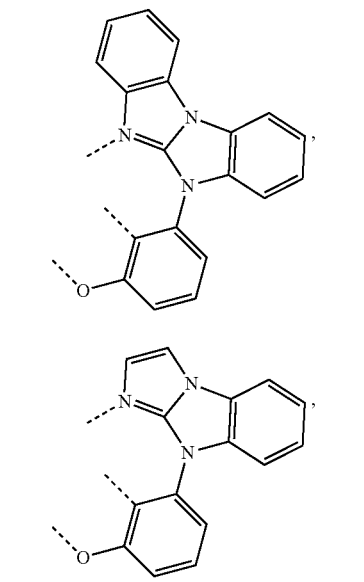
L<sub>B35</sub>
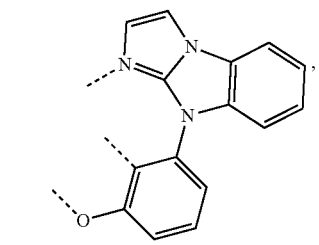
L<sub>B36</sub>
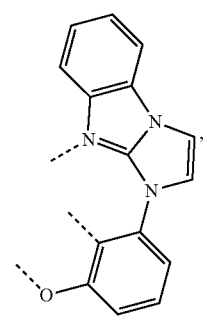
L<sub>B37</sub>
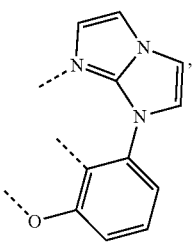
L<sub>B38</sub>
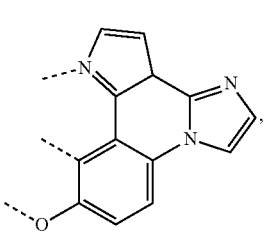
L<sub>B39</sub>
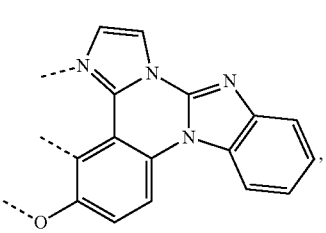
L<sub>B40</sub>
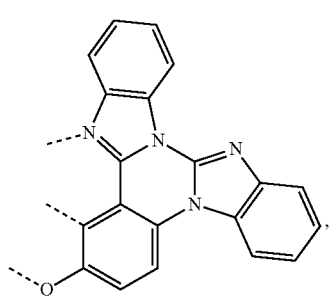
L<sub>B41</sub>
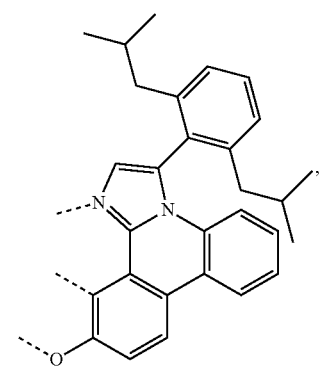

-continued

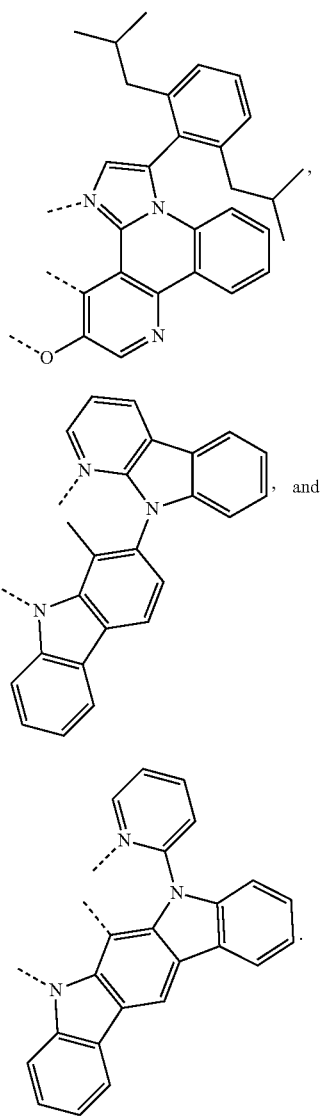
$L_{B42}$, $L_{B43}$, and $L_{B44}$.

An OLED comprising an anode, a cathode, and an organic layer, disposed between the anode and the cathode, where the organic layer comprises a compound having the formula:

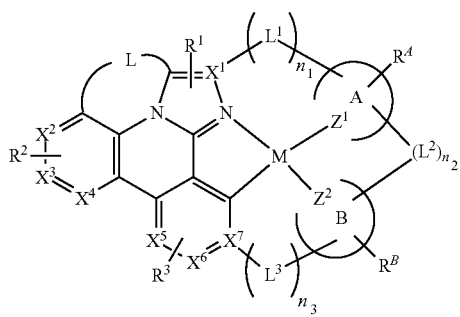

Formula I is also disclosed. In Formula I, rings A and B are each independently a 5- or 6-membered carbocyclic or heterocyclic ring. At least one of rings A and B is a 5-membered carbocyclic or heterocyclic ring. $Z^1$, $Z^2$, $X^1$ to $X^7$ are each independently selected from the group consisting of carbon and nitrogen. Each of $R^1$, $R^2$, $R^3$, $R^A$ and $R^B$ independently represents none to a maximum possible number of substitutions. $R^1$, $R^2$, $R^3$, $R^A$ and $R^B$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any two substitutions in $R^1$, $R^2$, $R^3$, $R^A$ and $R^B$ are optionally joined or fused into a ring. Each of $n_1$, $n_2$, and $n_3$ is independently 0 or 1. When $n_1$, $n_2$ or $n_3$ is 1, each of the respective $L^1$, $L^2$, or $L^3$ is independently selected from the group consisting of a direct bond, BR, NR, PR, O, S, Se, C=O, S=O, $SO_2$, CRR', SiRR', GeRR', alkyl, cycloalkyl, and combinations thereof, wherein R and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. When $n_1$, $n_2$ or $n_3$ is 0, the respective $L^1$, $L^2$, or $L^3$ is not present. $n_1+n_2+n_3$ is at least 2. When $L^1$ is present, $X^1$ is carbon. When $L^3$ is present, $X^7$ is carbon. L is a linking group having two to three linking atoms, wherein the linking atoms are each independently selected from the group consisting of C, Si, O, S, N, B or combinations thereof. M is Pt or Pd.

In some embodiments of the OLED, $R^1$, $R^2$, $R^3$, $R^A$, $R^B$, R and R' are each independently selected from the group consisting of hydrogen, deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof.

A consumer product comprising the OLED is also disclosed.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

An emissive region in an OLED is also disclosed. The emissive region comprises a compound having the formula:

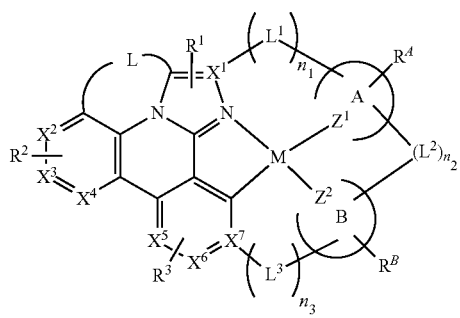

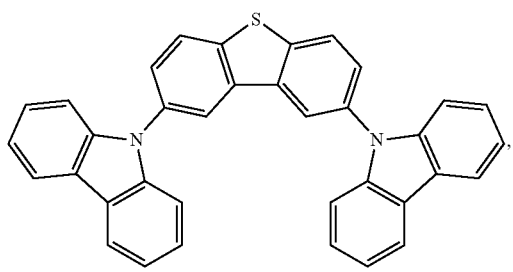

Formula I is also disclosed. In Formula I, rings A and B are each independently a 5- or 6-membered carbocyclic or heterocyclic ring. At least one of rings A and B is a 5-membered carbocyclic or heterocyclic ring. $Z^1$, $Z^2$, $X^1$ to $X^7$ are each independently selected from the group consisting of carbon and nitrogen. Each of $R^1$, $R^2$, $R^3$, $R^A$ and $R^B$ independently represents none to a maximum possible number of substitutions. $R^1$, $R^2$, $R^3$, $R^A$ and $R^B$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Any two substitutions in $R^1$, $R^2$, $R^3$, $R^A$ and $R^B$ are optionally joined or fused into a ring. Each of $n_1$, $n_2$, and $n_3$ is independently 0 or 1. When $n_1$, $n_2$ or $n_3$ is 1, each of the respective $L^1$, $L^2$, or $L^3$ is independently selected from the group consisting of a direct bond, BR, NR, PR, O, S, Se, C=O, S=O, $SO_2$, CRR', SiRR', GeRR', alkyl, cycloalkyl, and combinations thereof, wherein R and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. When $n_1$, $n_2$ or $n_3$ is 0, the respective $L^1$, $L^2$, or $L^3$ is not present. $n_1+n_2+n_3$ is at least 2. When $L^1$ is present, $X^1$ is carbon. When $L^3$ is present, $X^7$ is carbon. L is a linking group having two to three linking atoms, wherein the linking atoms are each independently selected from the group consisting of C, Si, O, S, N, B or combinations thereof. M is Pt or Pd.

In some embodiments of the emissive region, the compound is an emissive dopant or a non-emissive dopant. In some embodiments of the emissive region, the emissive region further comprises a host, wherein the host comprises at least one selected from the group consisting of metal complex, triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene.

In some embodiments of the emissive region, the emissive region further comprises a host, wherein the host is selected from the group consisting of:

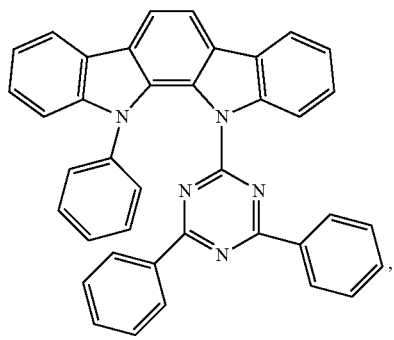

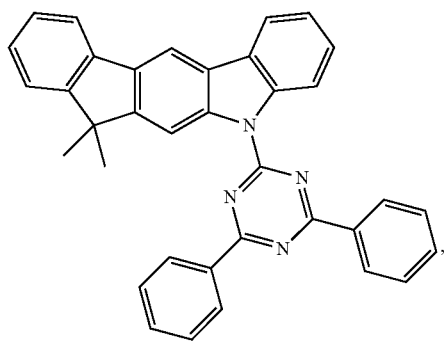

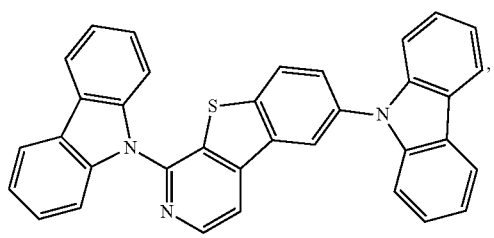

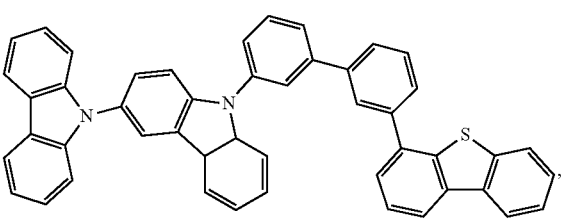

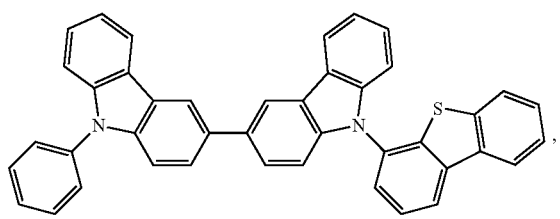

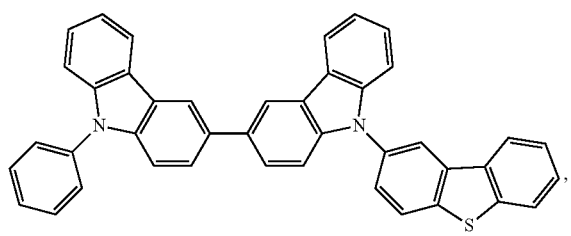
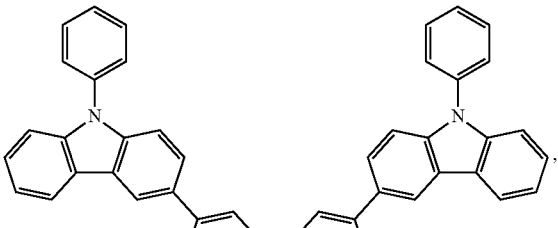
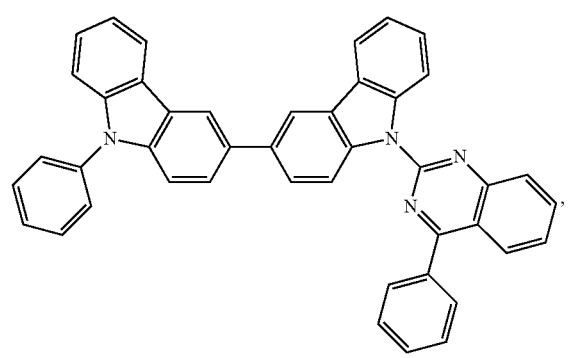
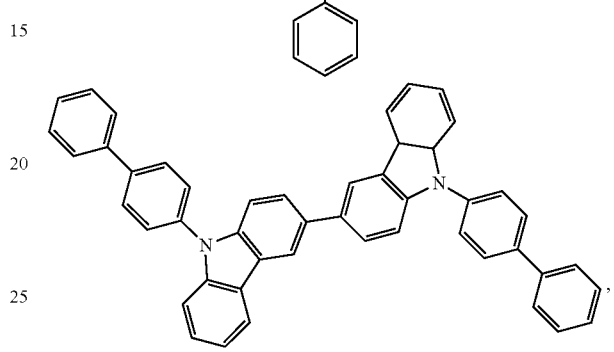
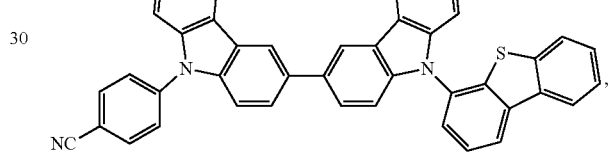
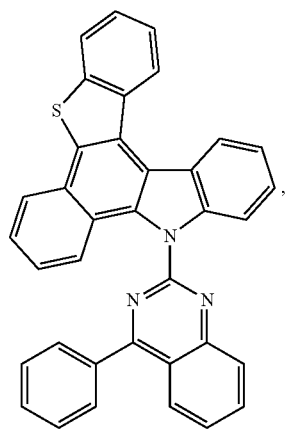
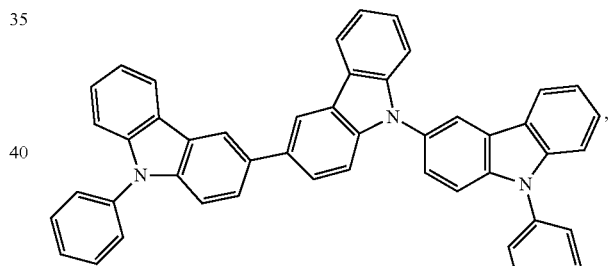
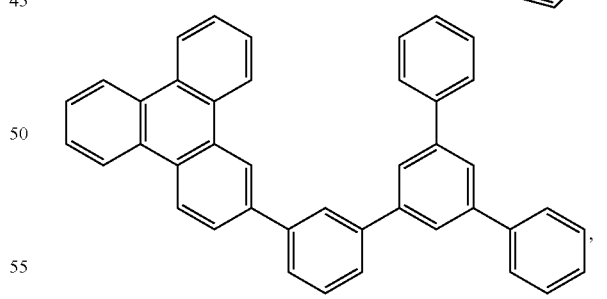
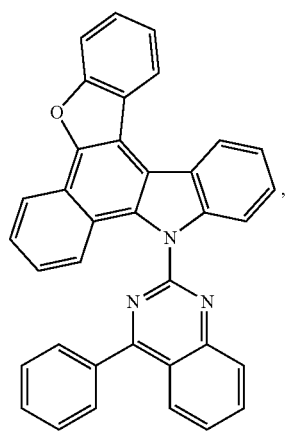
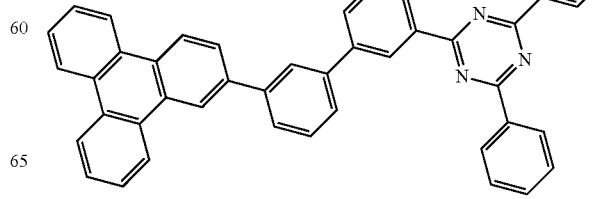

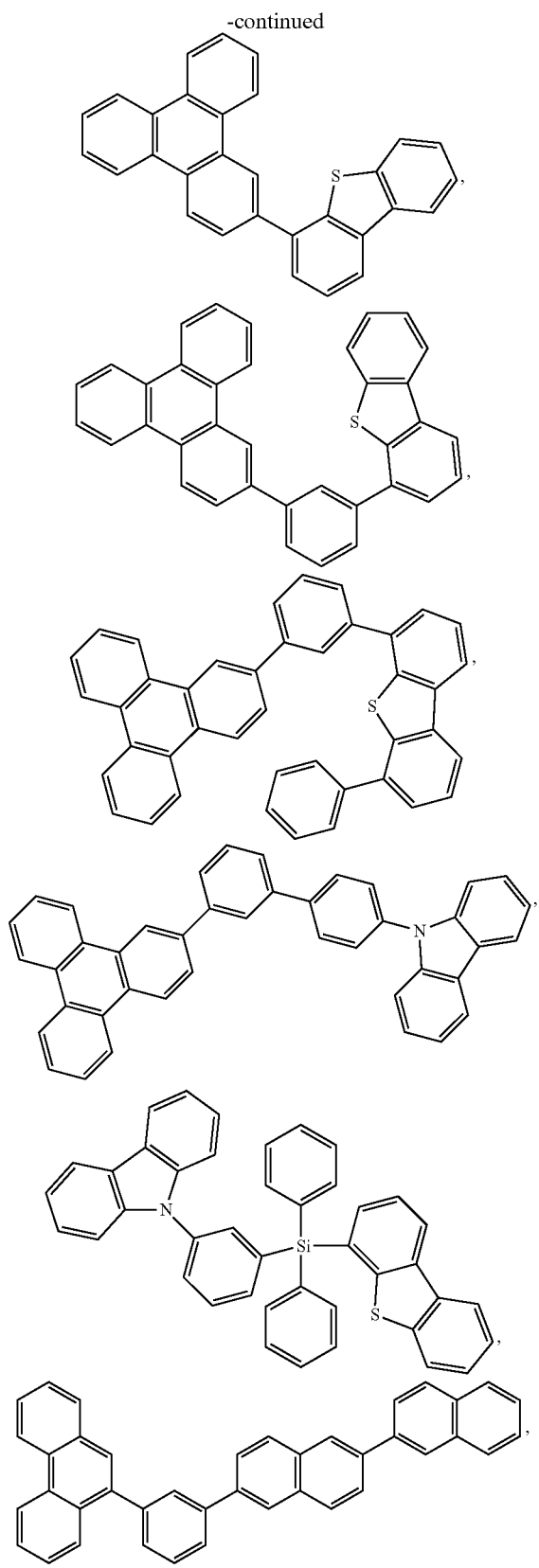

and combinations thereof.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used may be a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

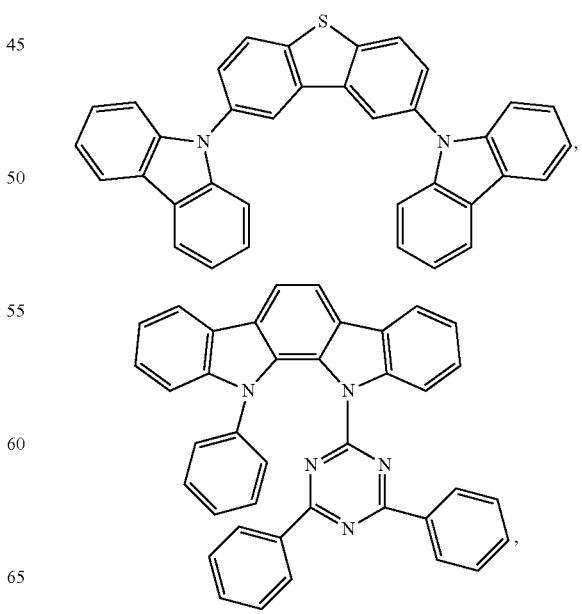

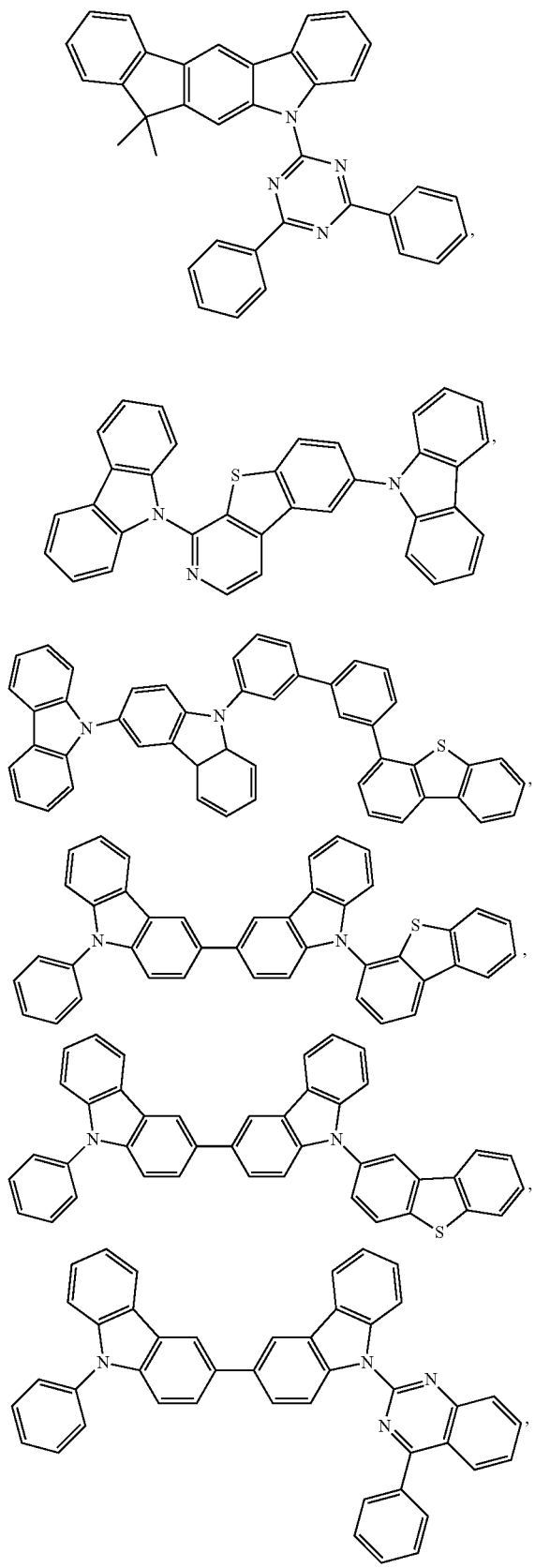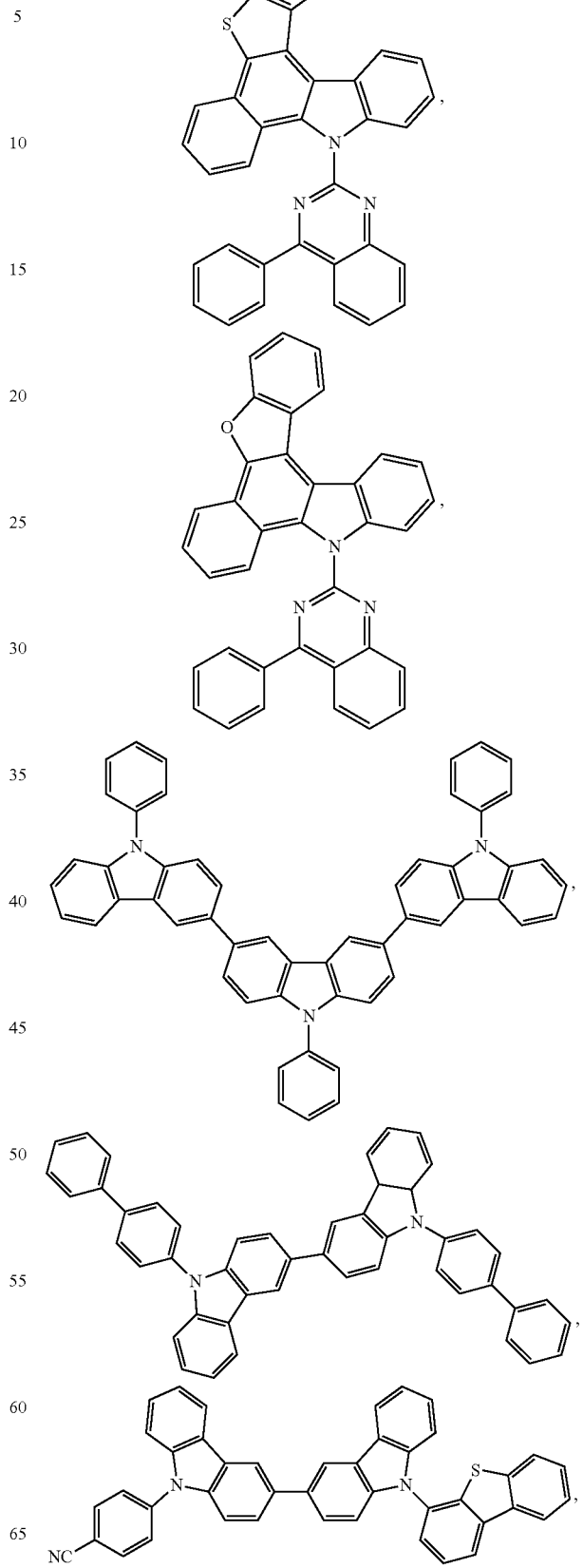

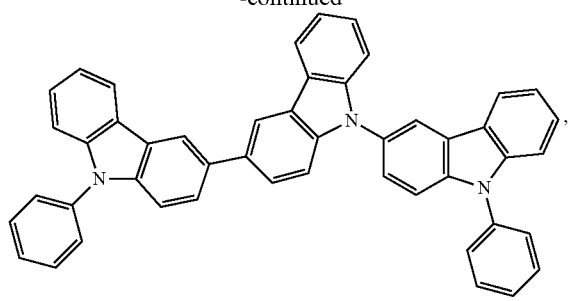

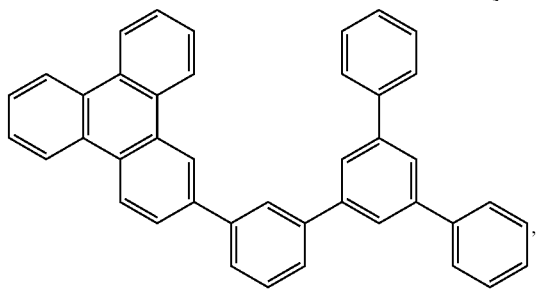

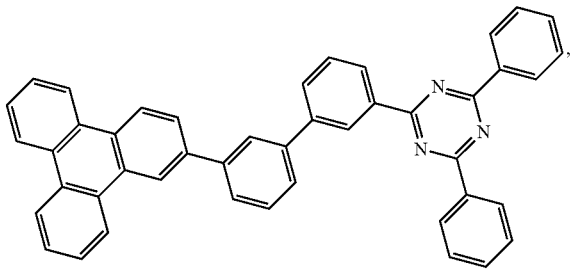

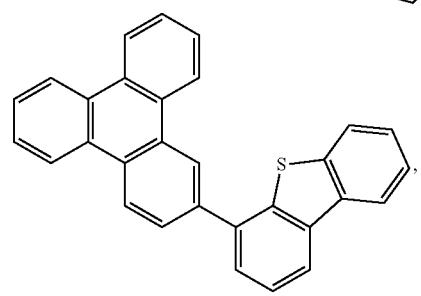

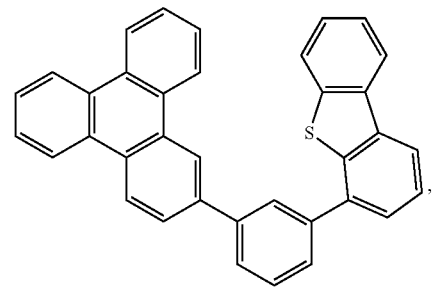

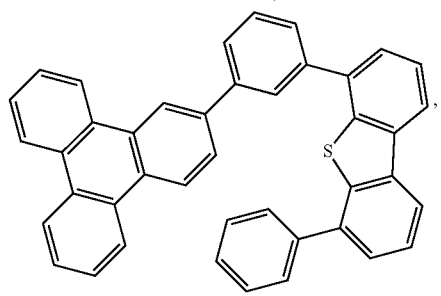

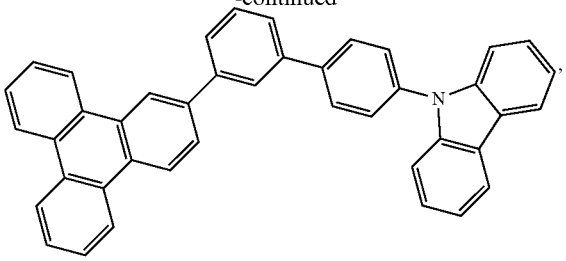

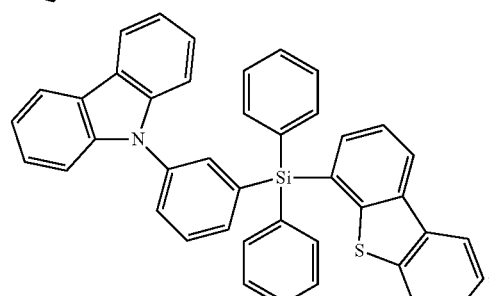

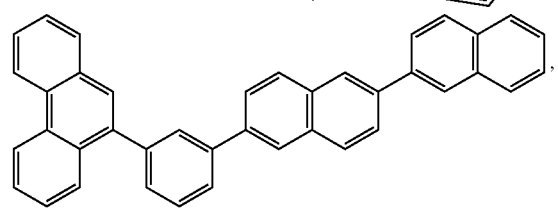

and combinations thereof.

Additional information on possible hosts is provided below.

In yet another aspect of the present disclosure, a formulation that comprises the novel compound disclosed herein is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.
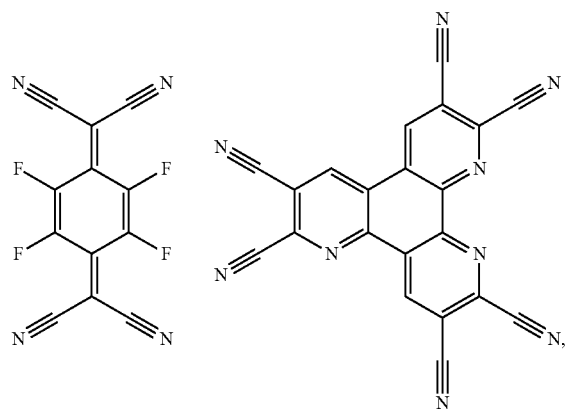
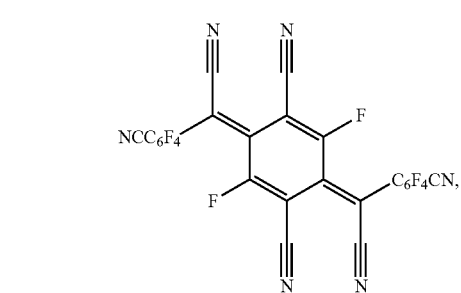
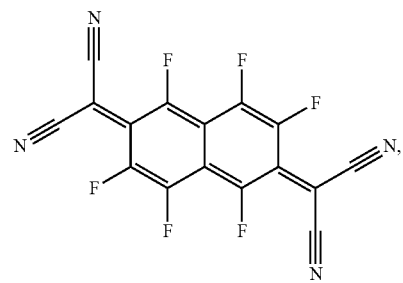
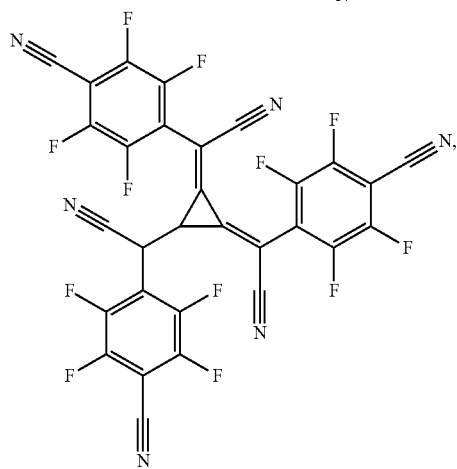
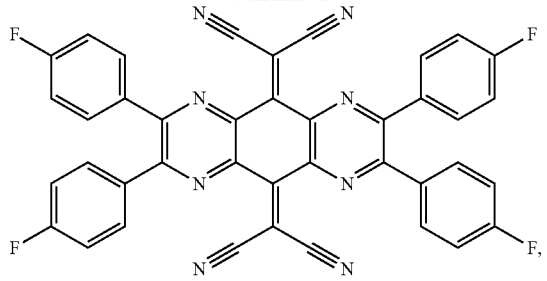
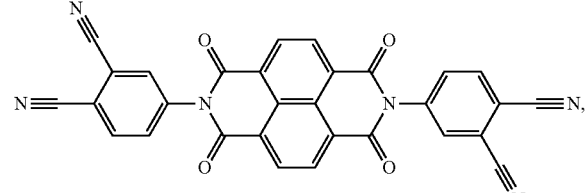
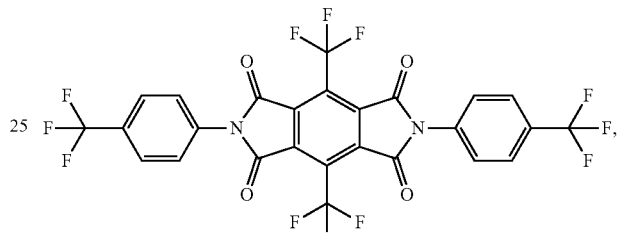
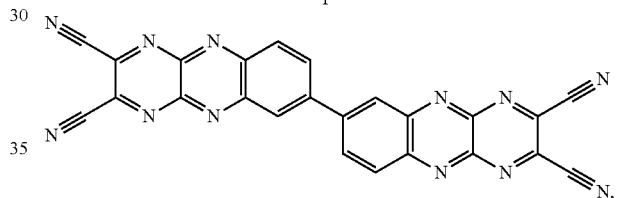
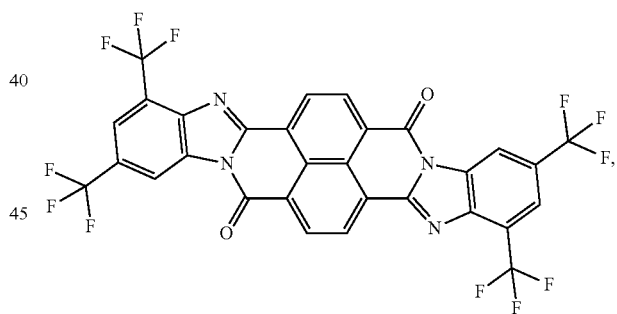
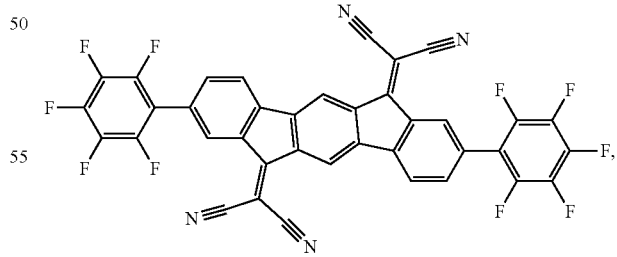
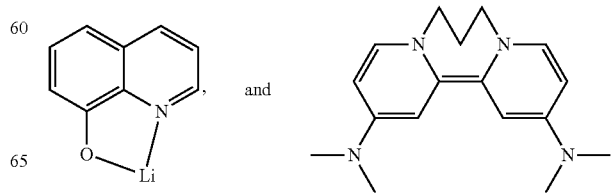

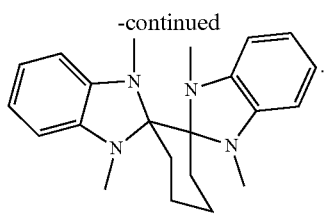

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

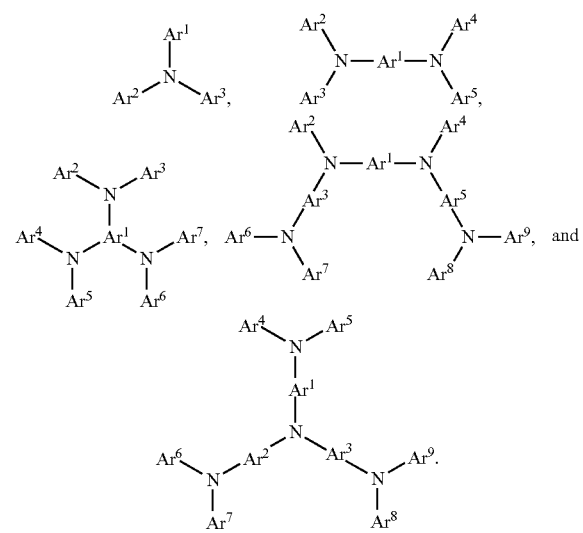

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

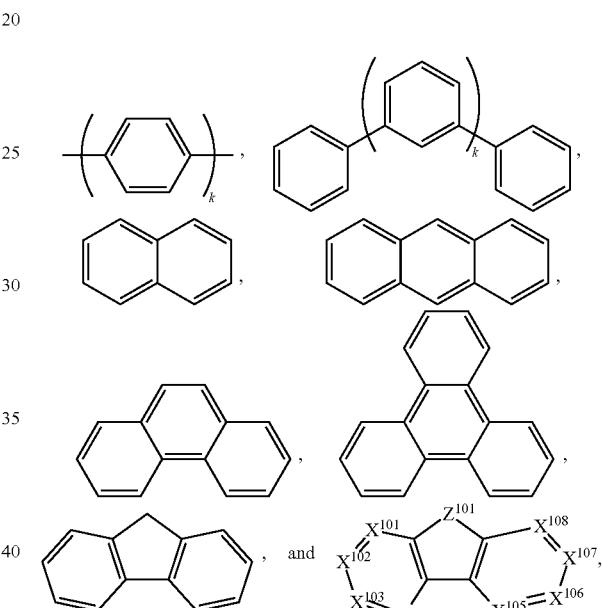

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

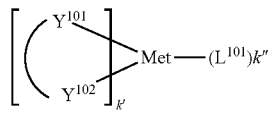

wherein Met is a metal, which can have an atomic weight greater than 40; ($Y^{101}$—$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$—$Y^{102}$) is a 2-phenylpyridine derivative. In another aspect, ($Y^{101}$—$Y^{102}$) is a carbene ligand. In another aspect, Met is selected from Ir, Pt, Os, and Zn. In a further aspect, the metal complex has a smallest oxidation potential in solution vs. Fc⁺/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

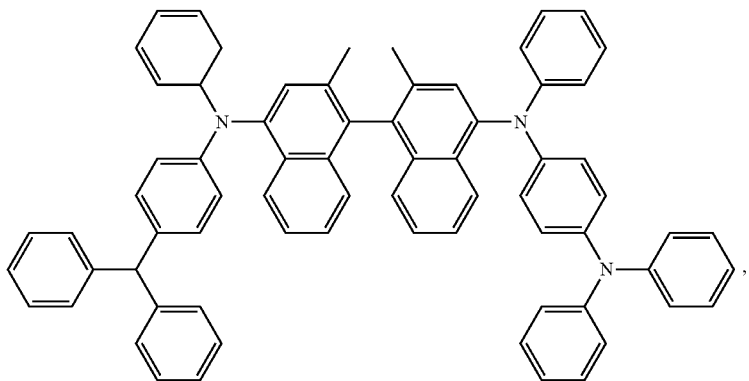

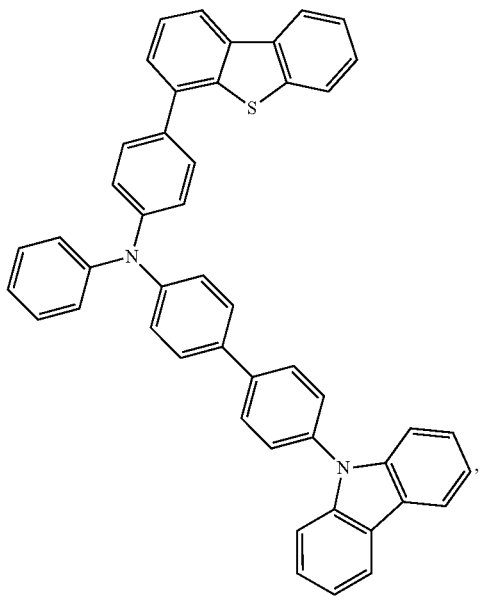

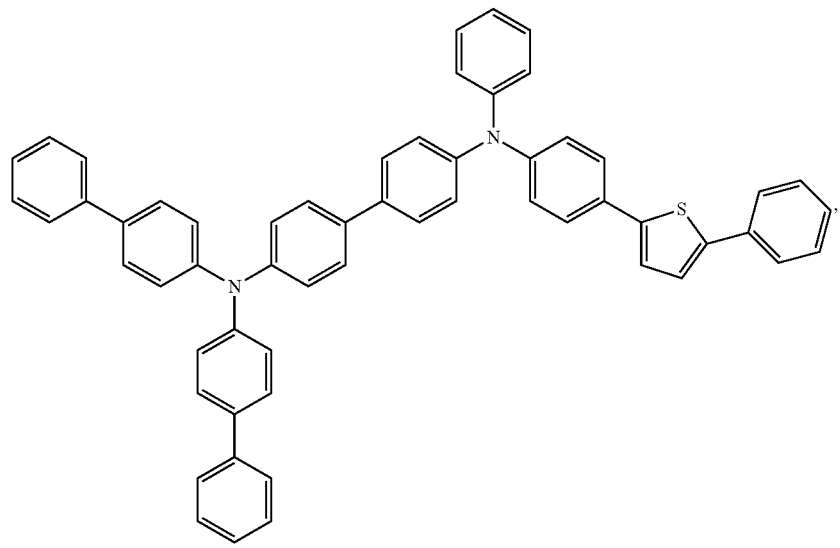
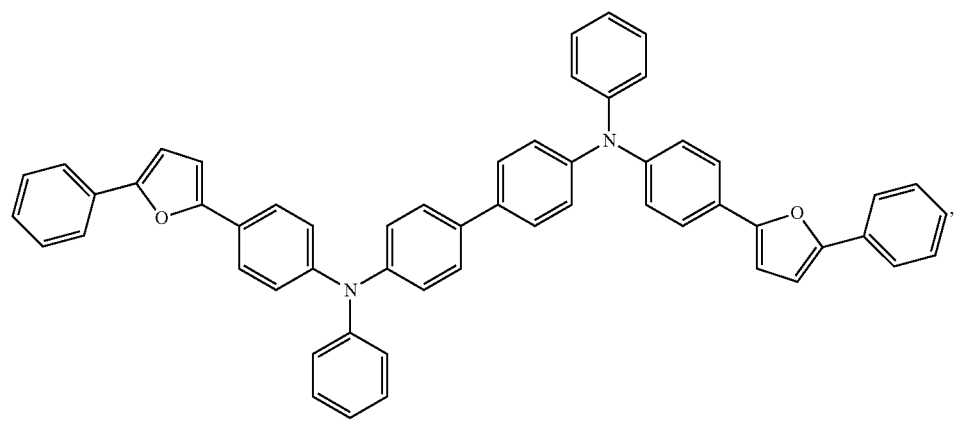
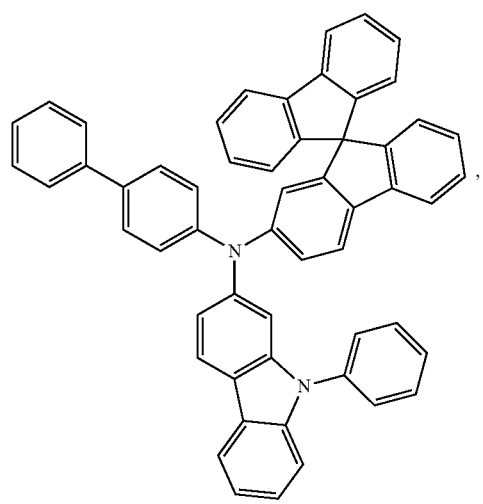

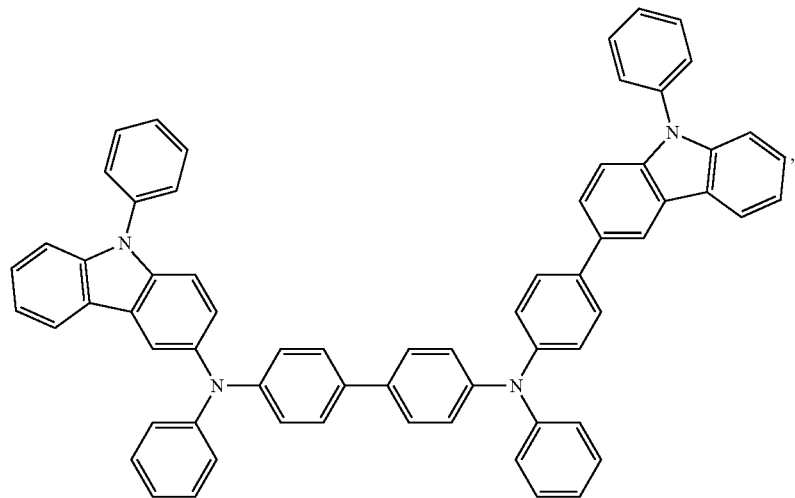
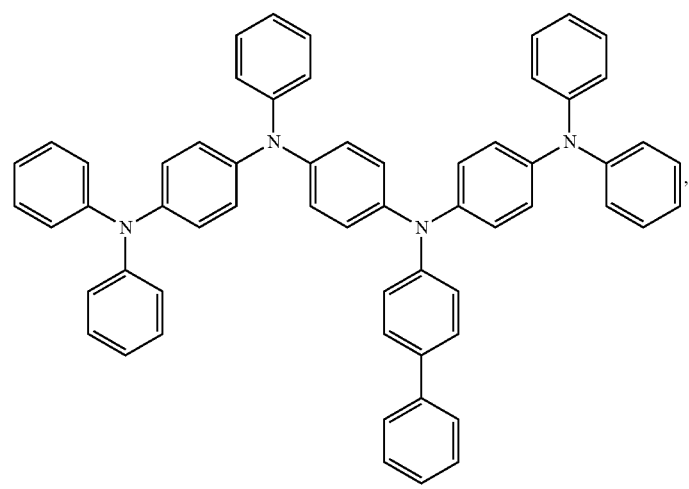
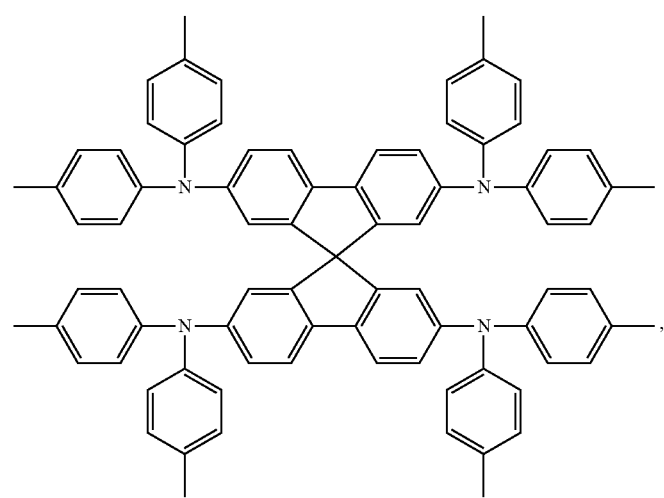

-continued
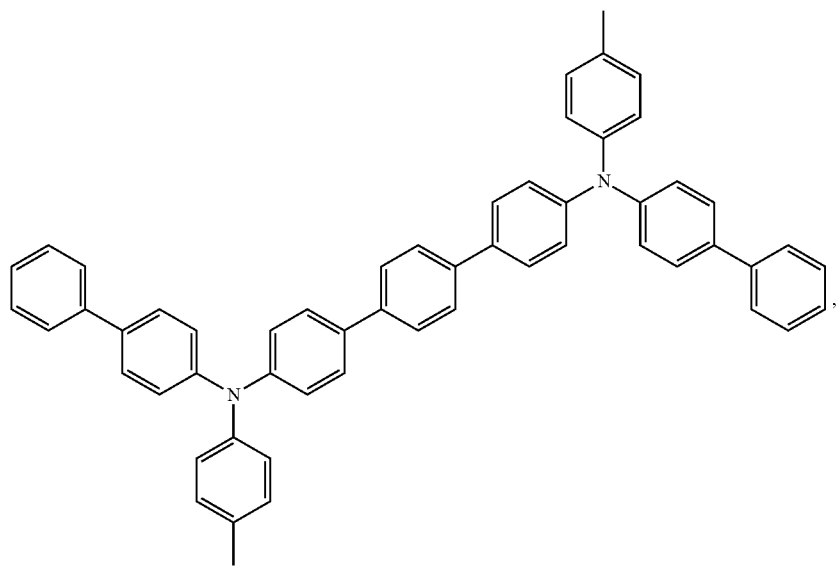
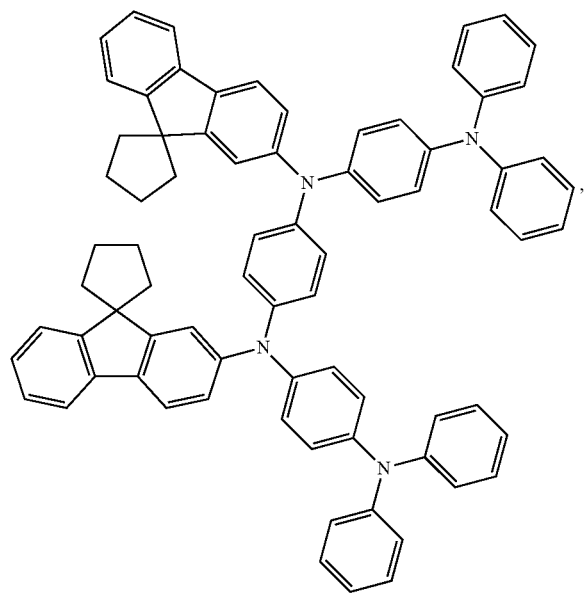
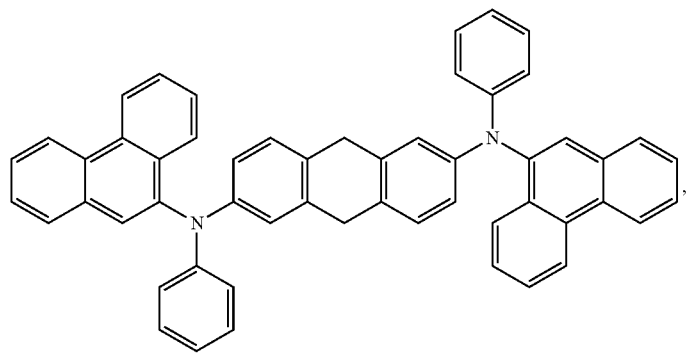

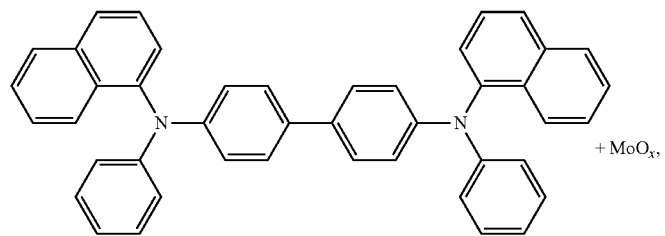
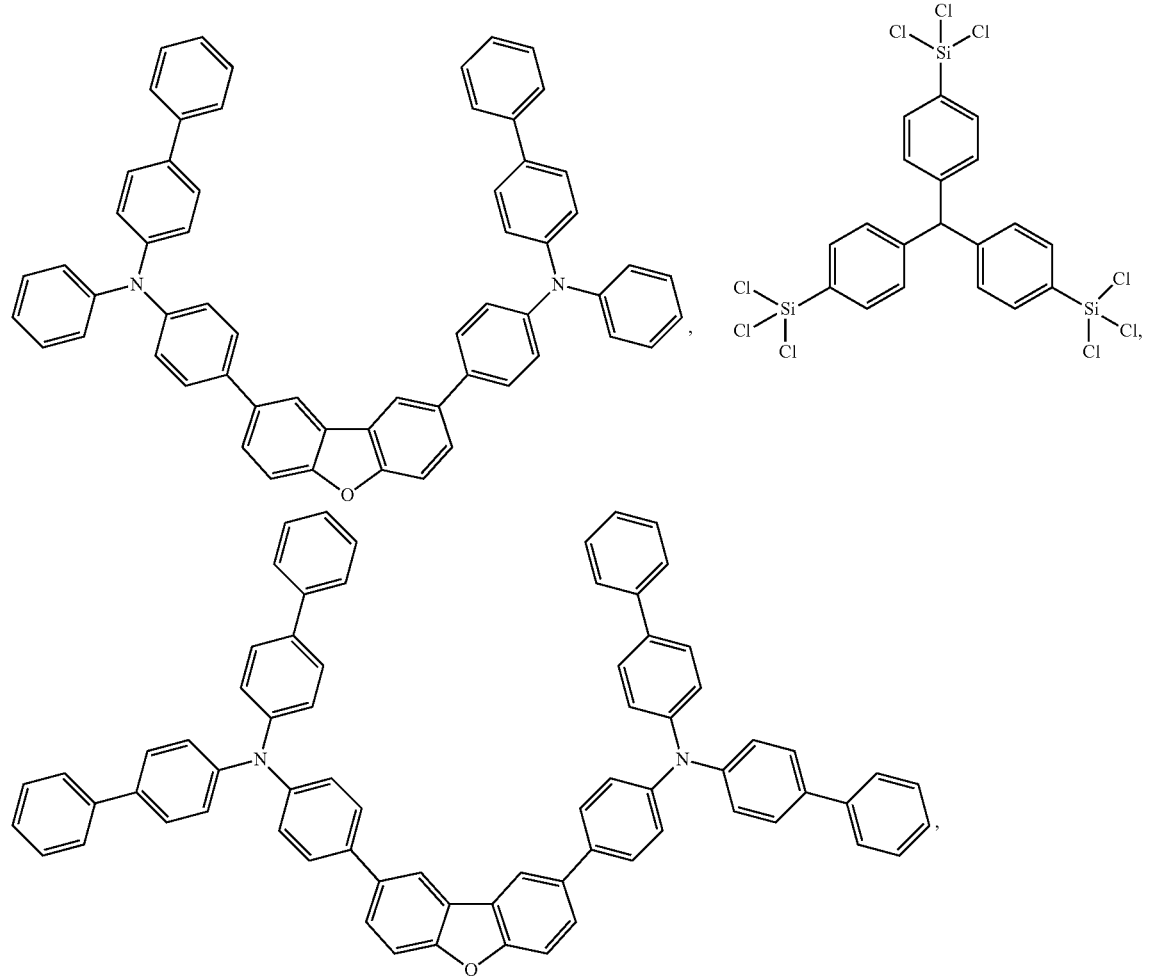
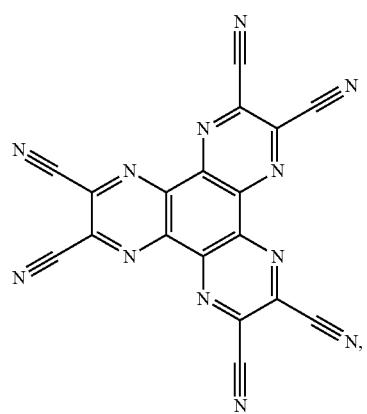

-continued
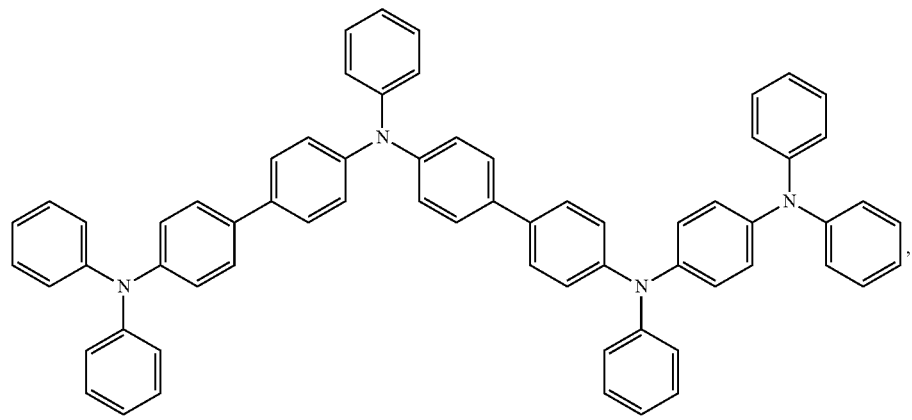
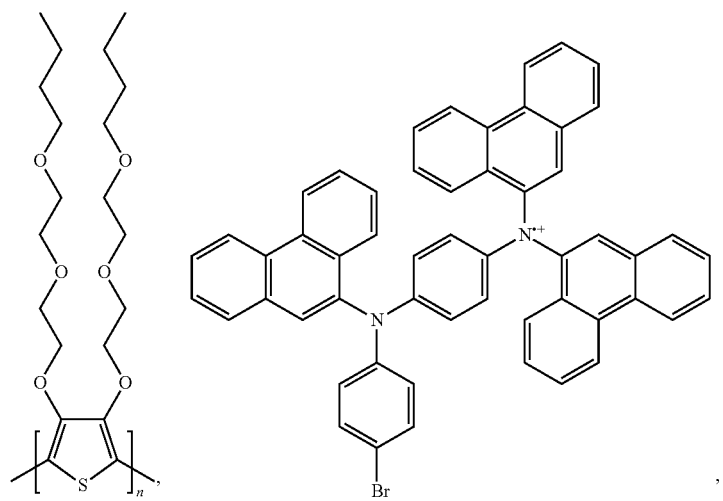
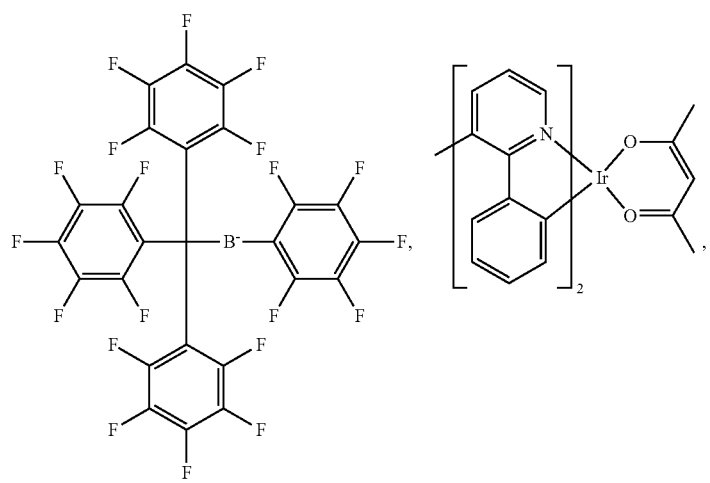

-continued
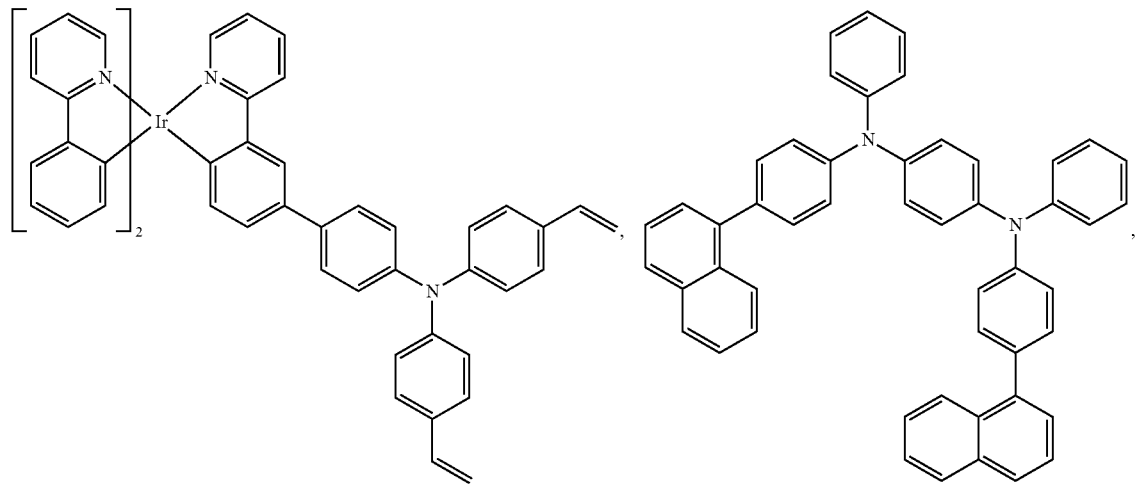
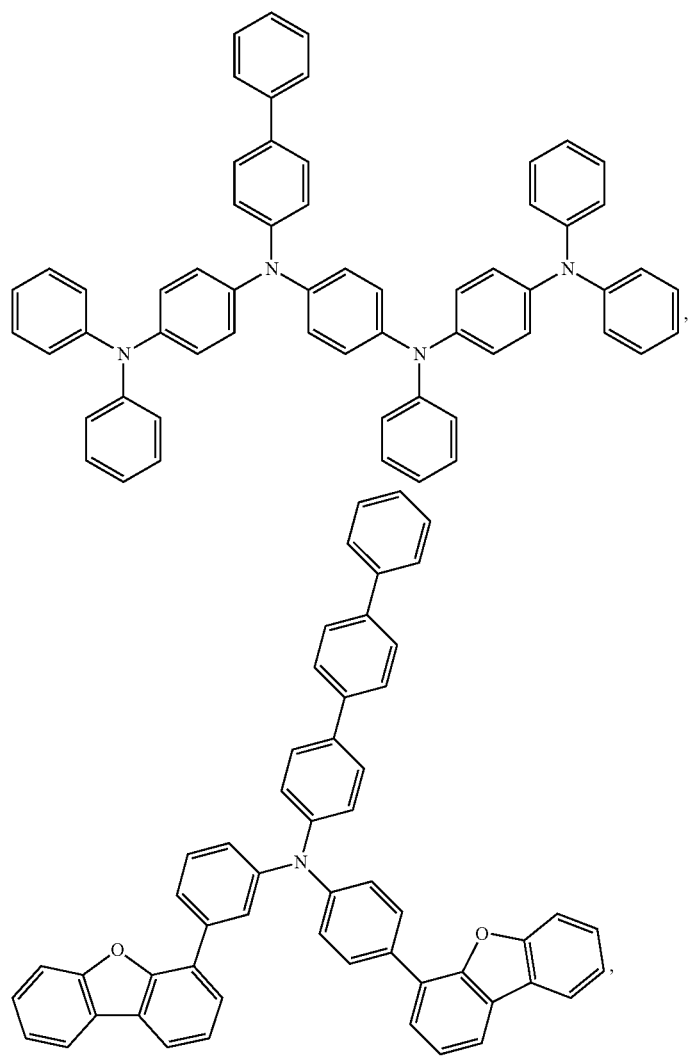

-continued
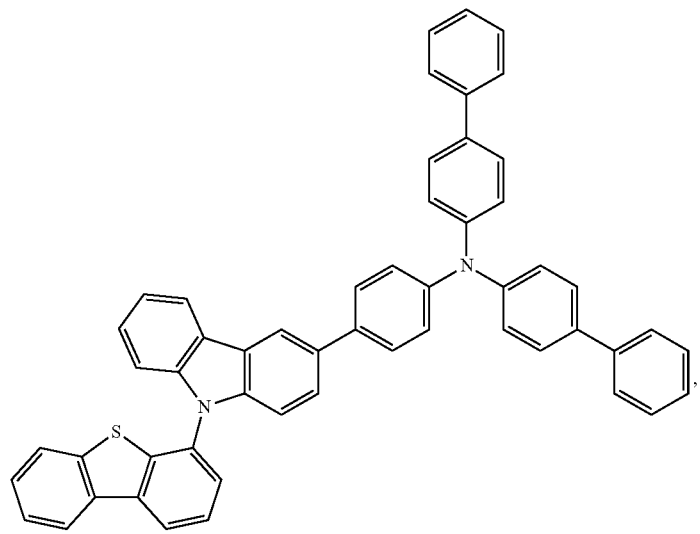
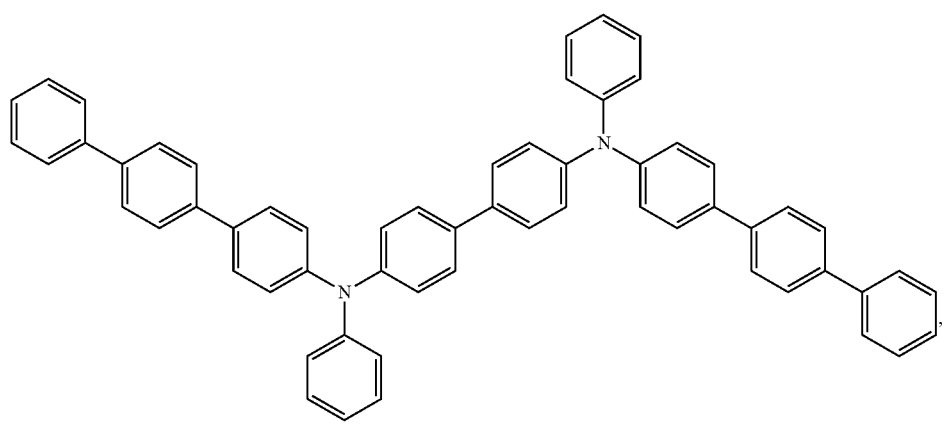
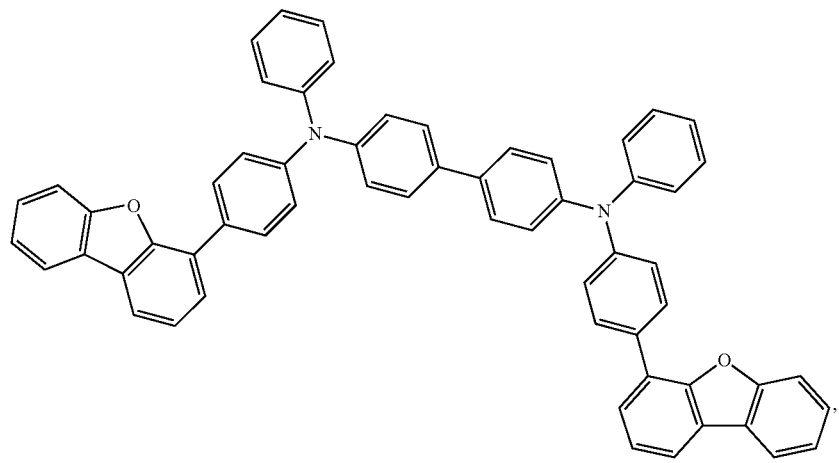

-continued
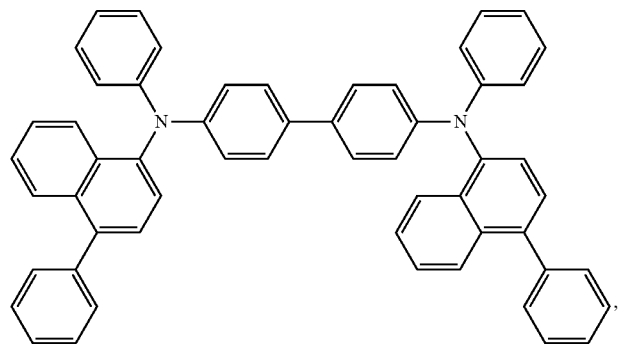
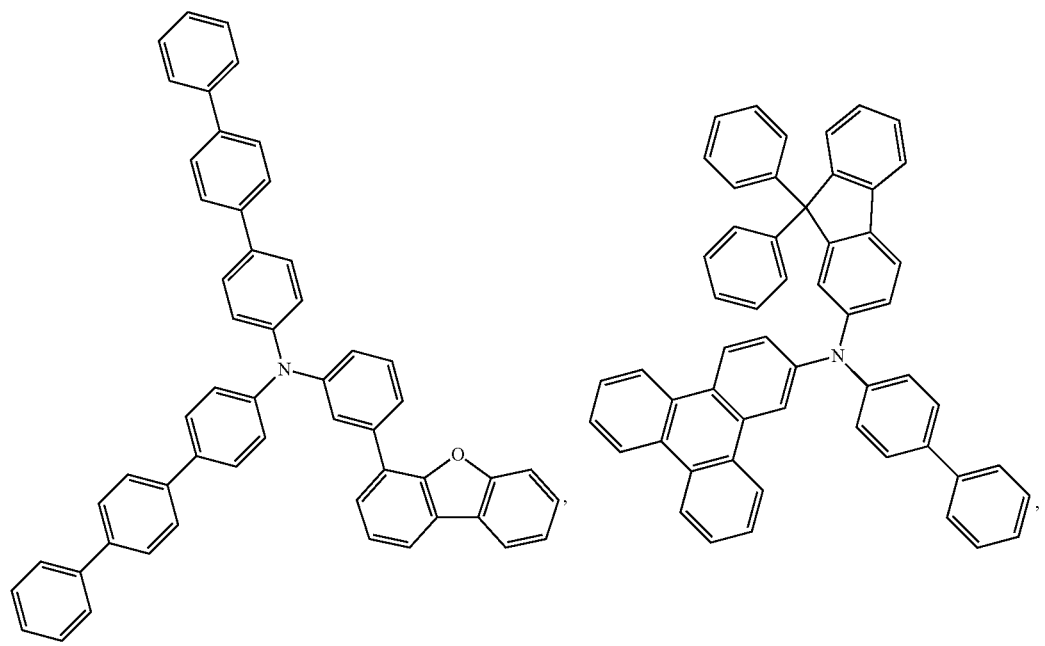
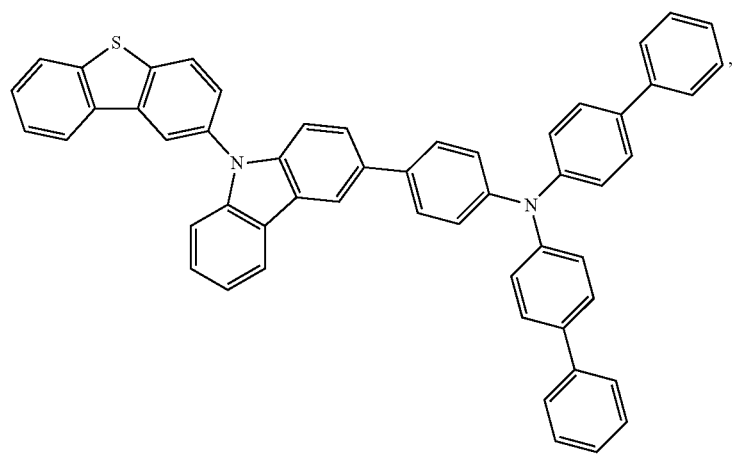

-continued
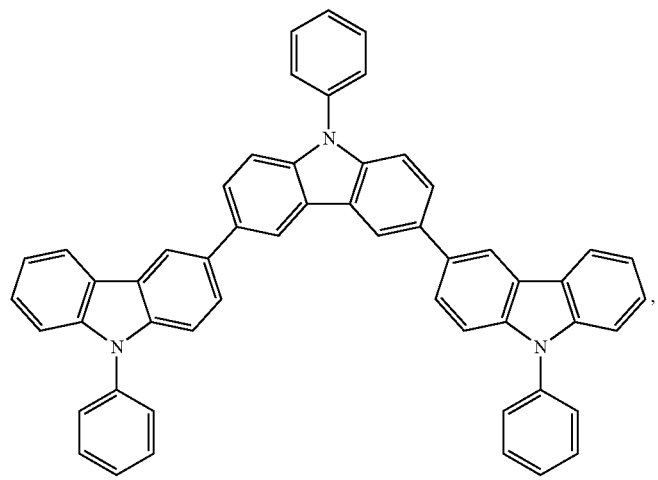
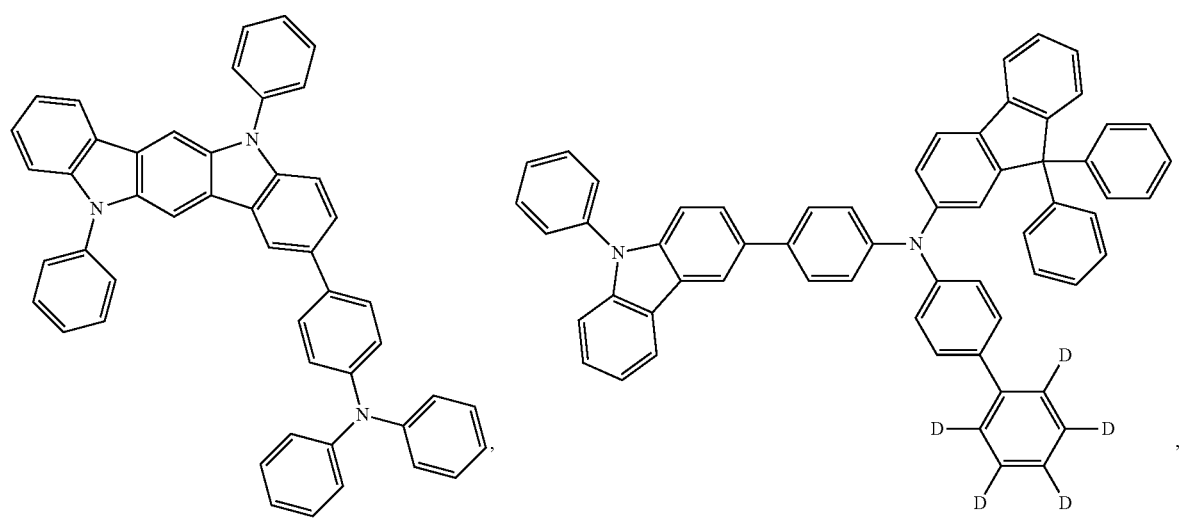
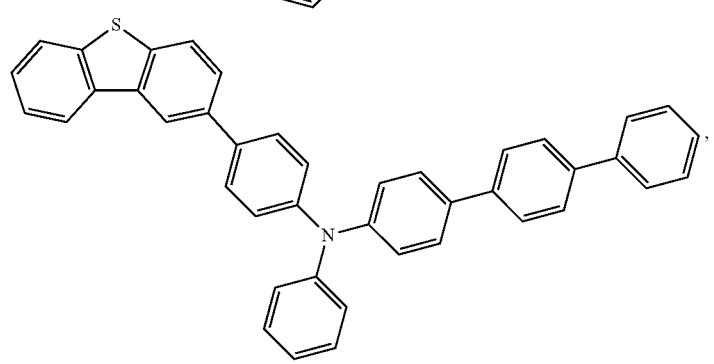
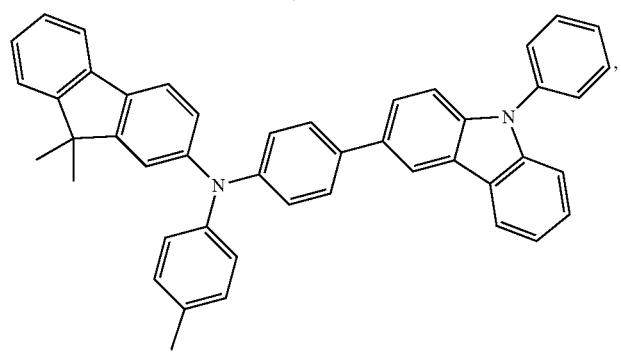

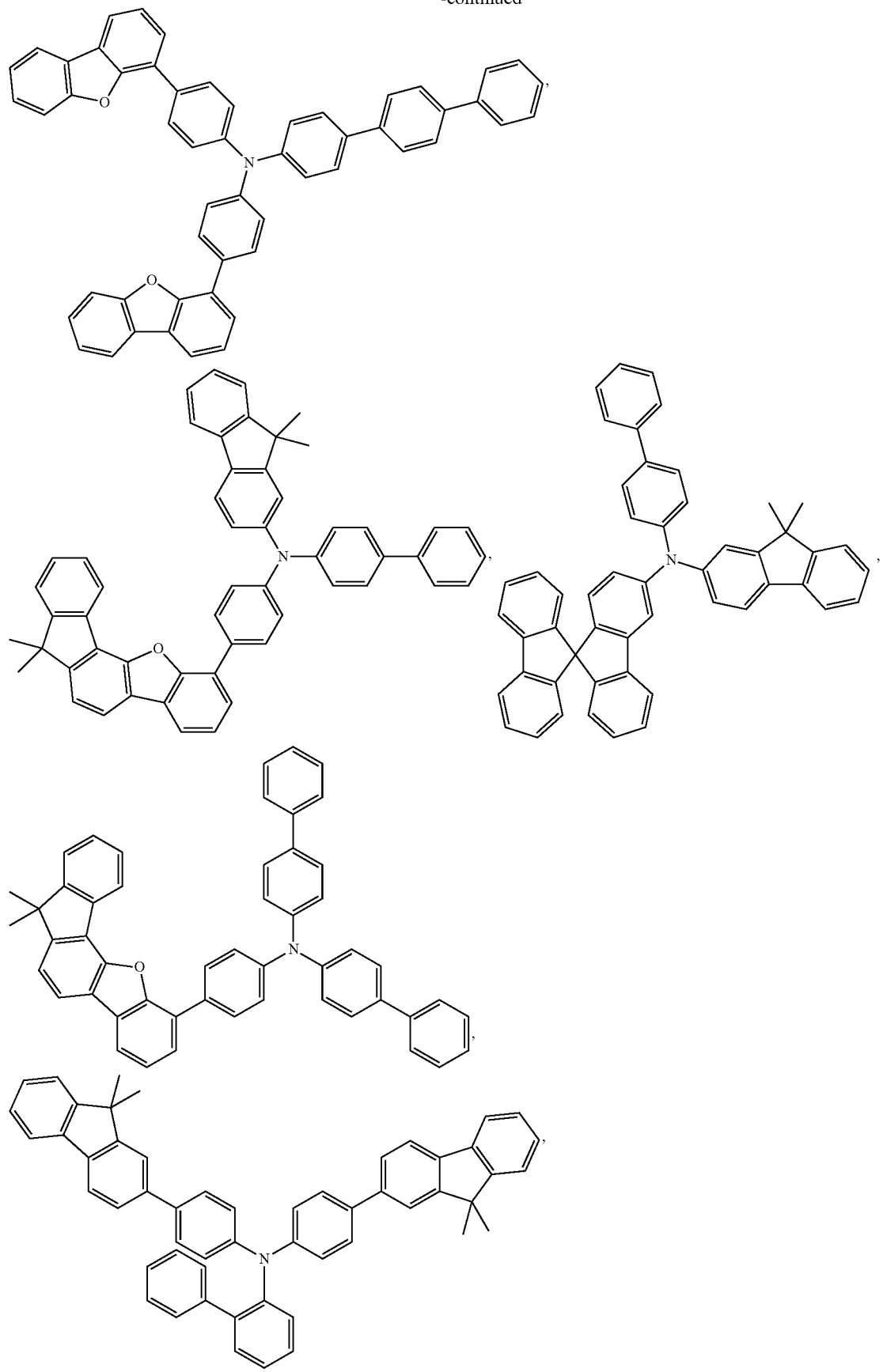

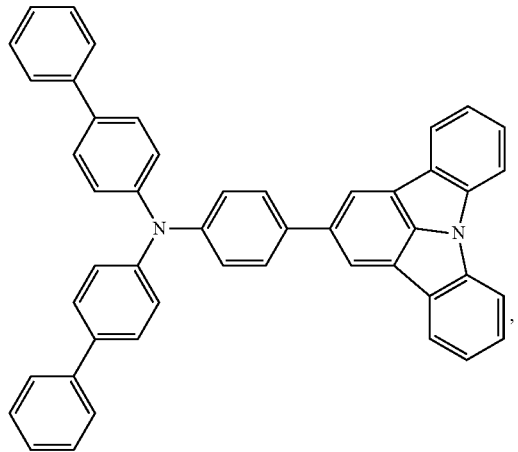
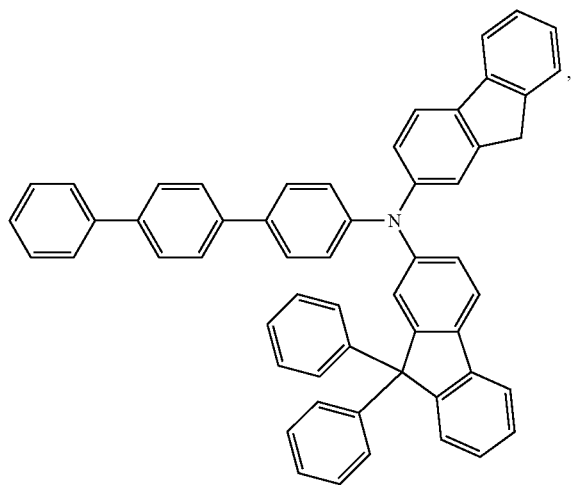
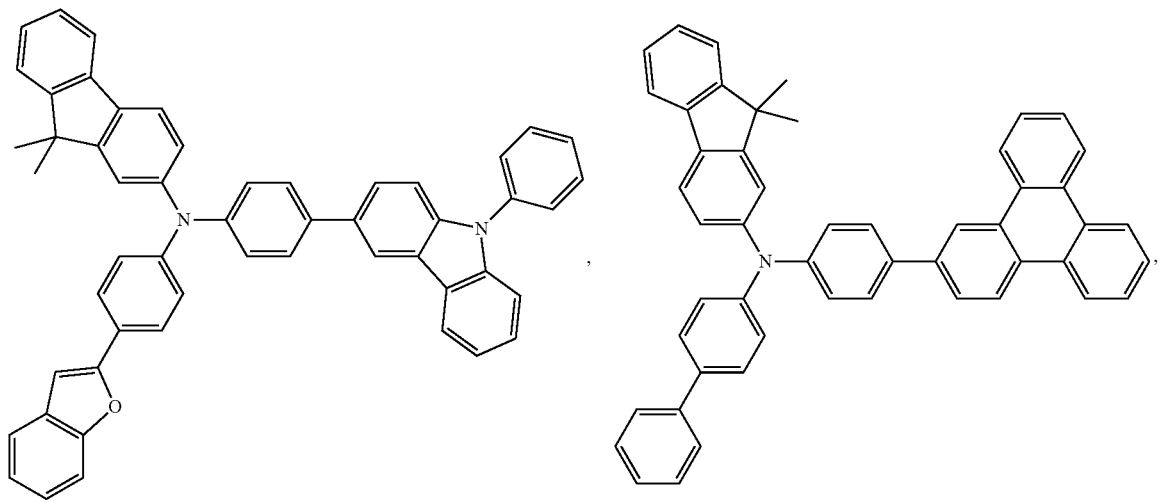

-continued
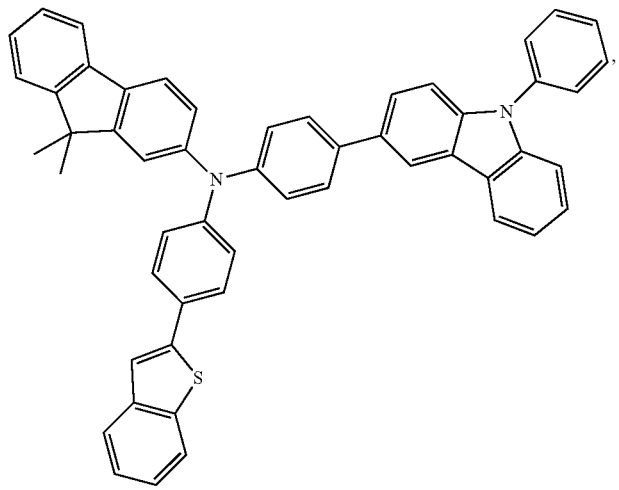
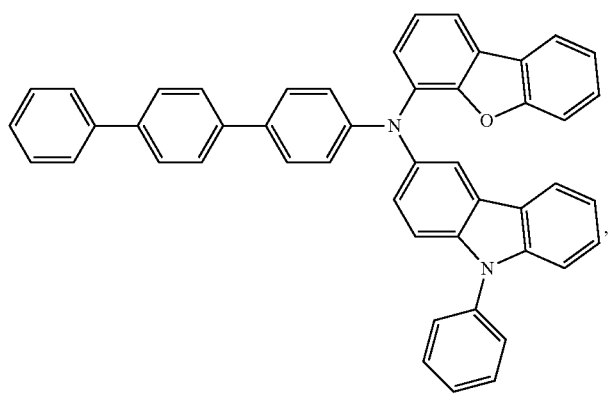
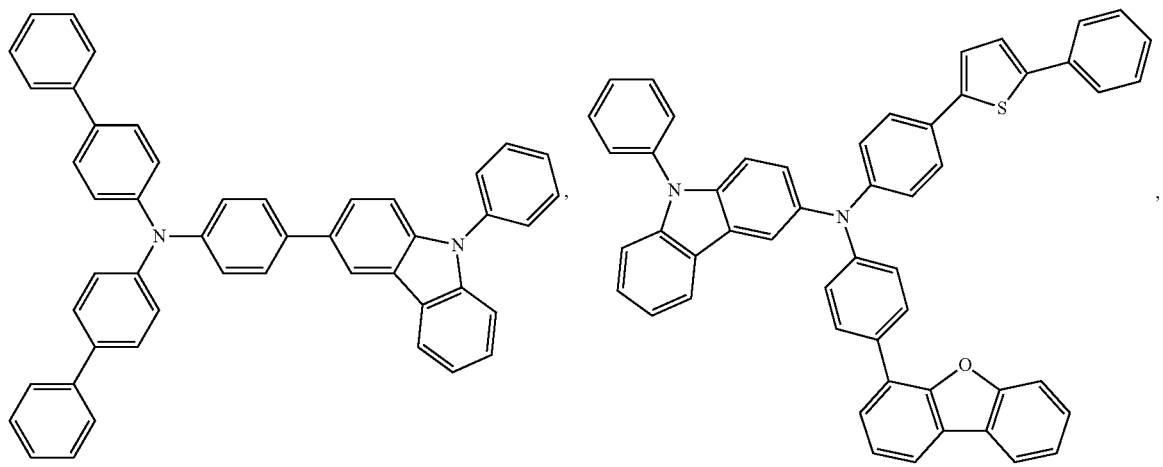

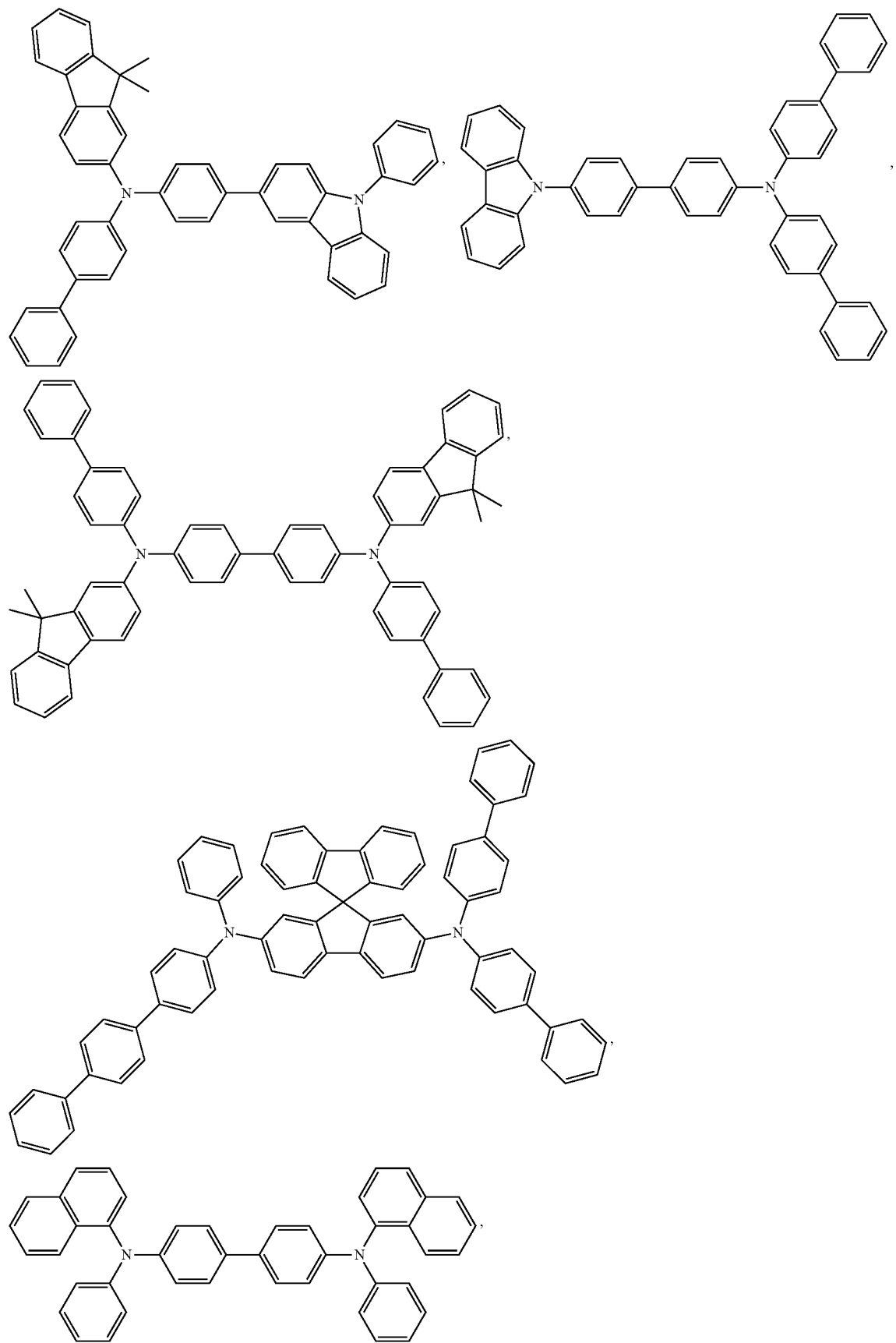

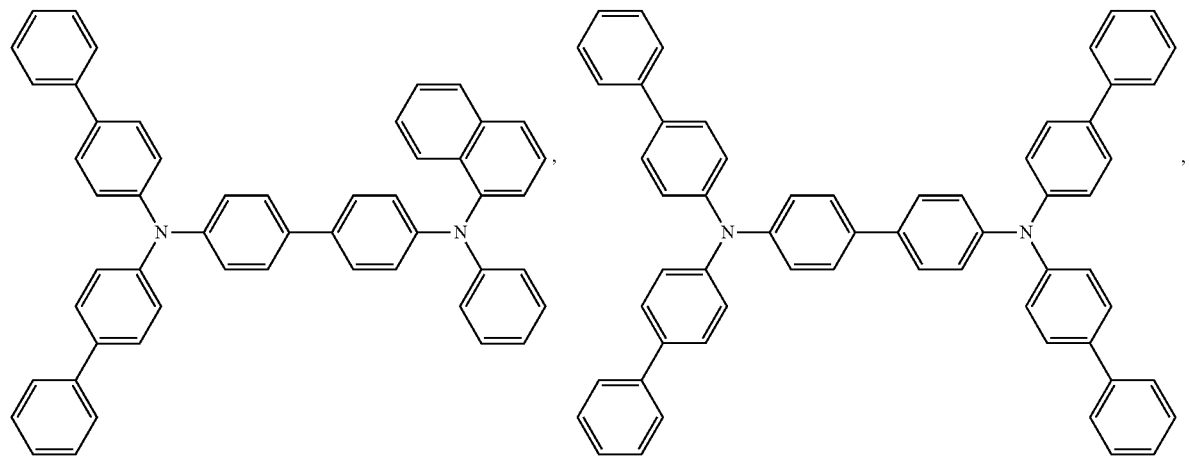
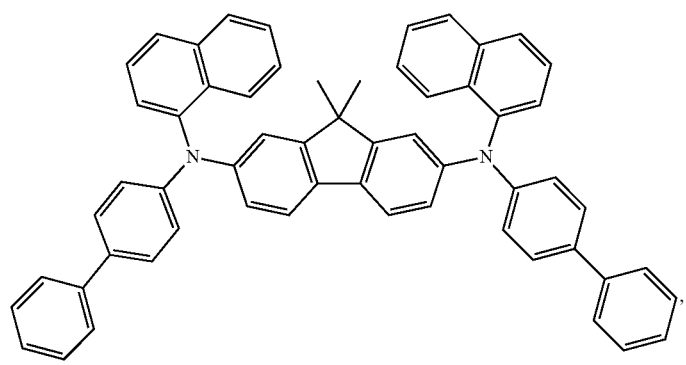
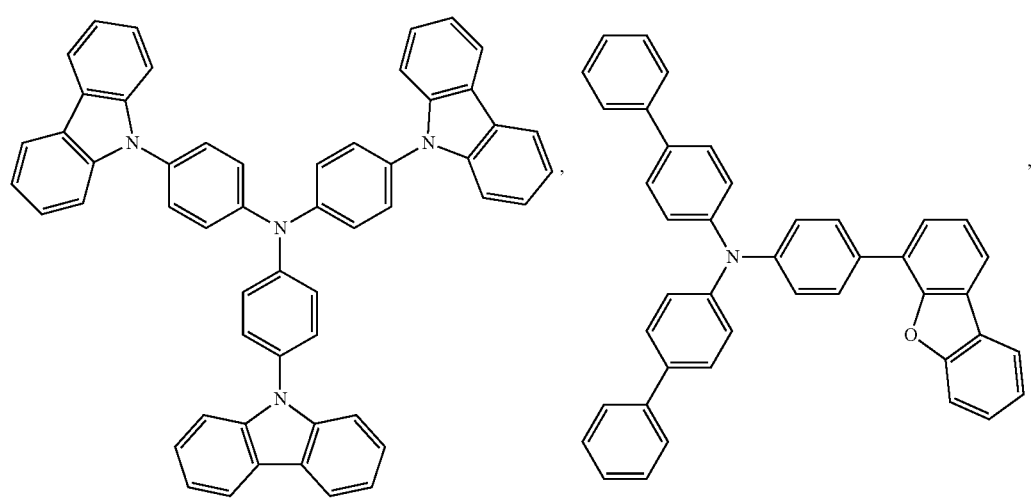

-continued

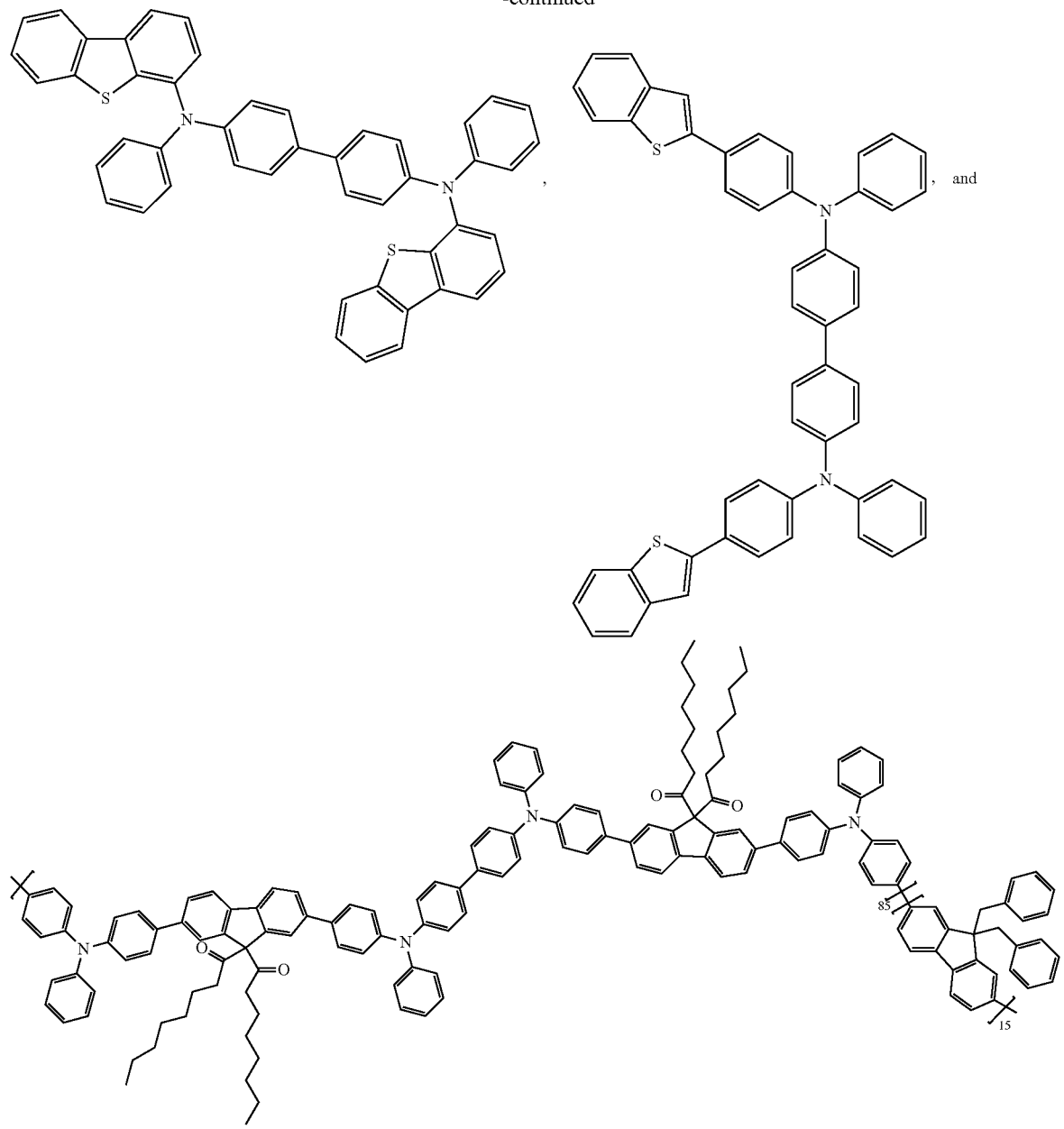

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

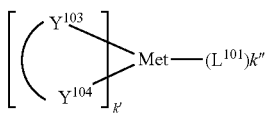

wherein Met is a metal; ($Y^{103}$—$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

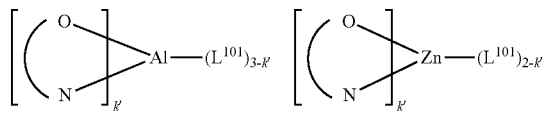

wherein (O—N) is a bidentate ligand, having metal coordinated to atoms O and N.

In another aspect, Met is selected from Ir and Pt. In a further aspect, ($Y^{103}$—$Y^{104}$) is a carbene ligand.

Examples of other organic compounds used as host are selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

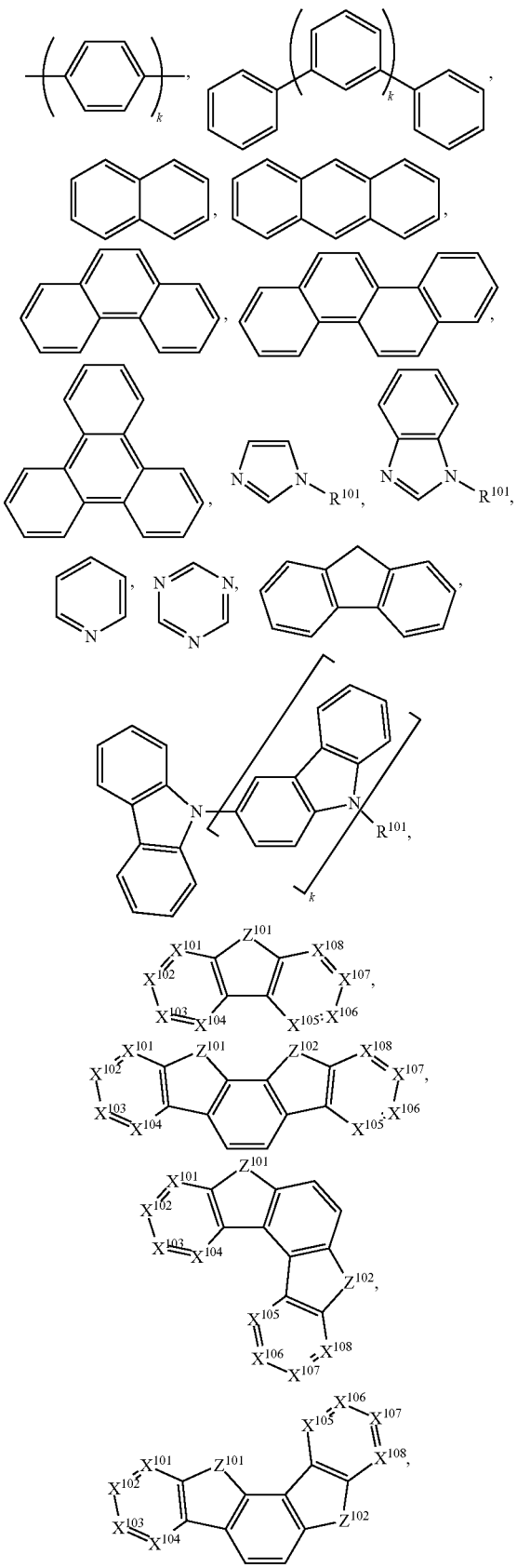

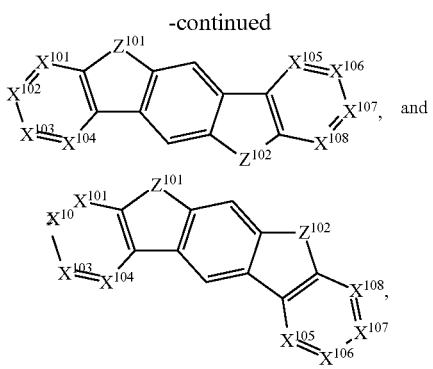

wherein R[101] is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472,

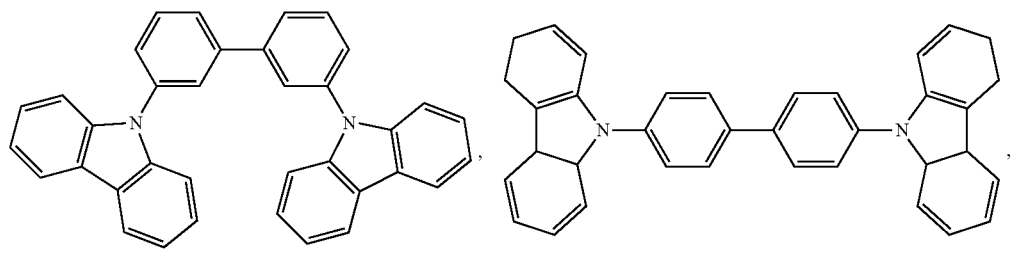

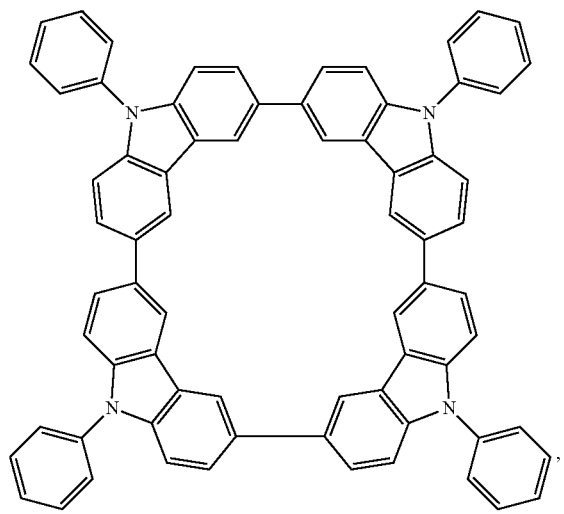

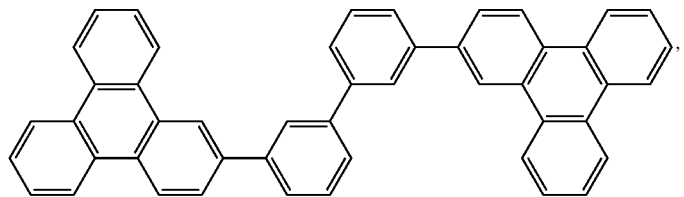
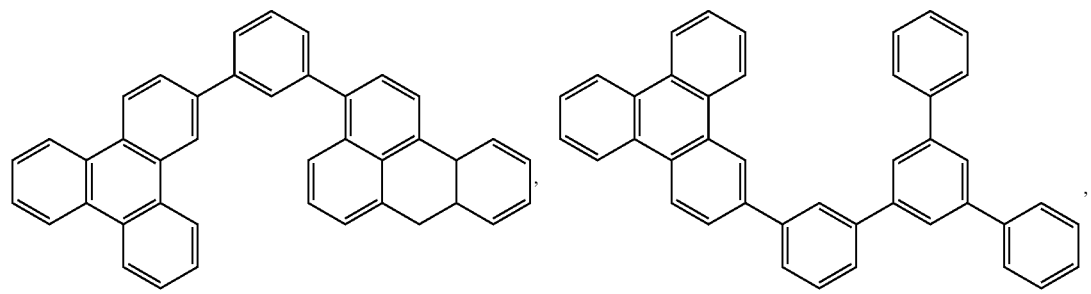
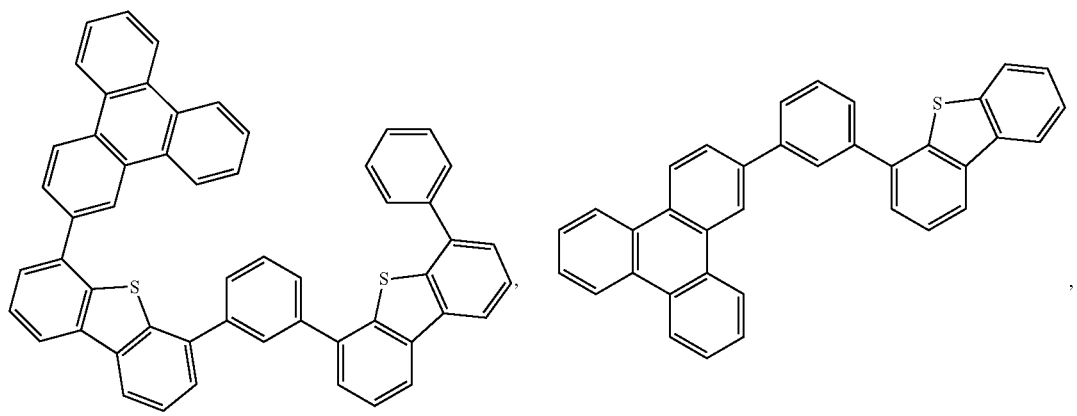
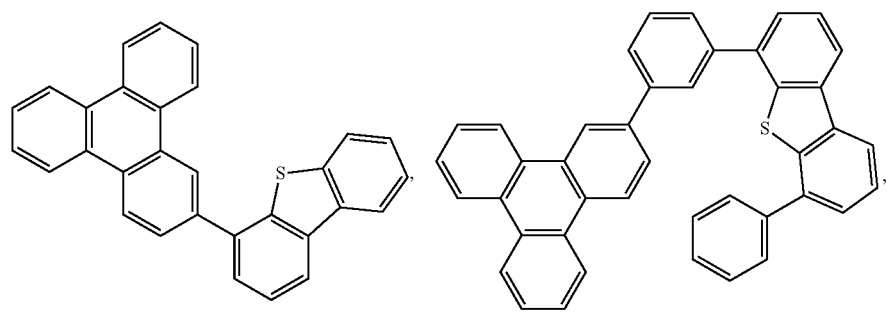

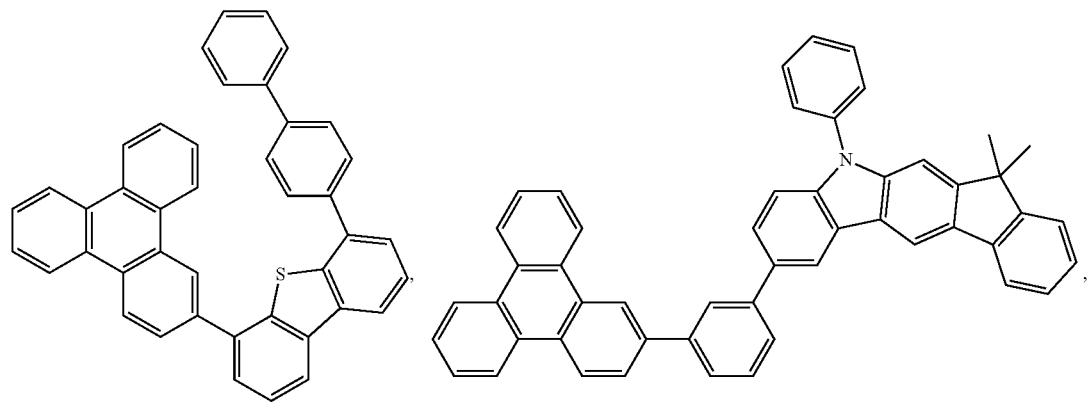
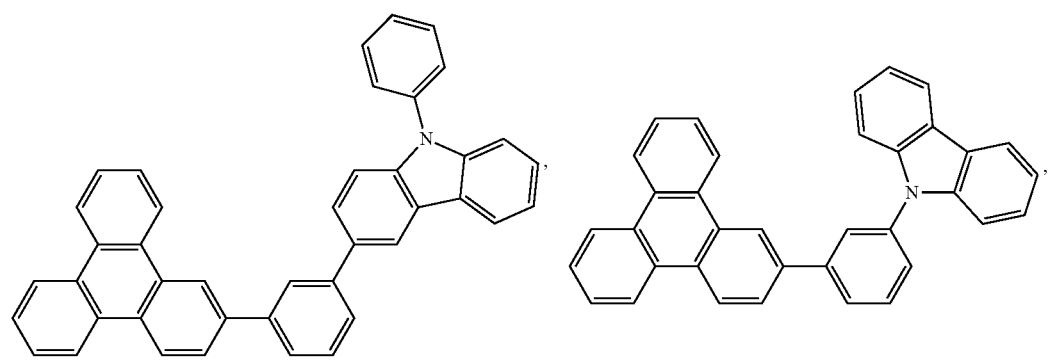
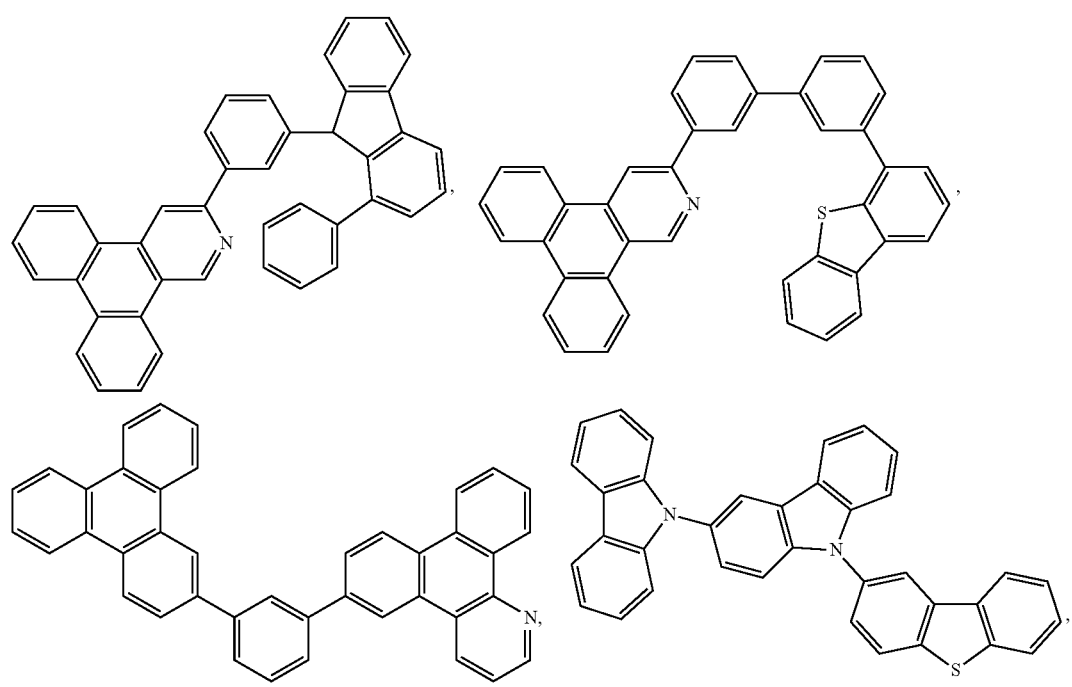

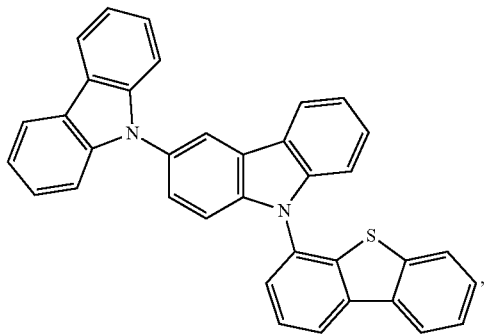
,
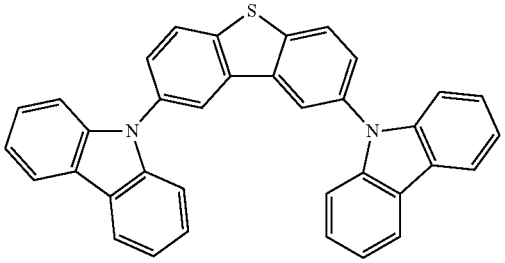
,
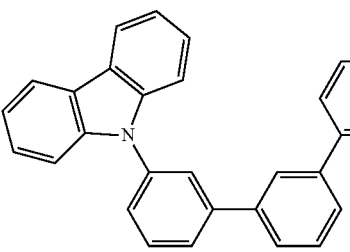
,
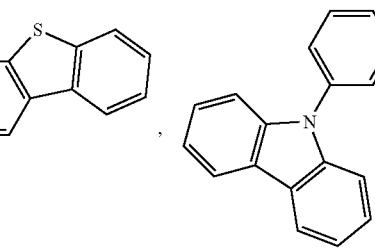
,
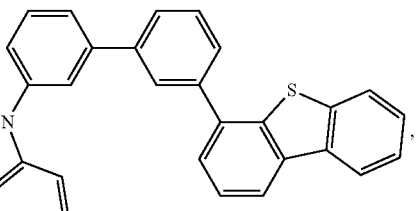
,
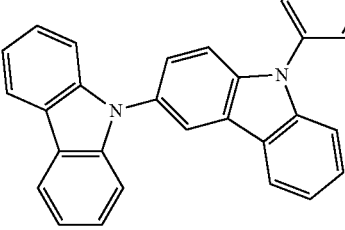
,
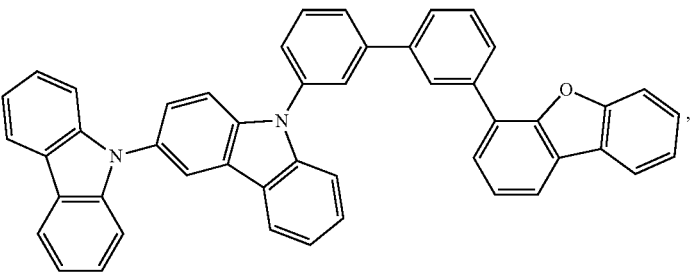
,
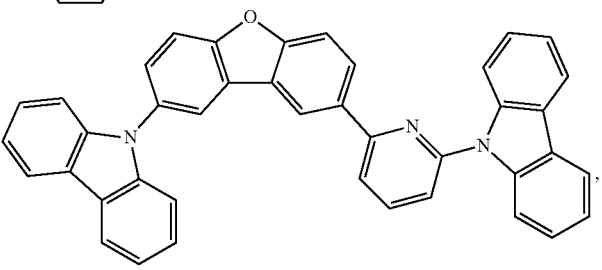
,
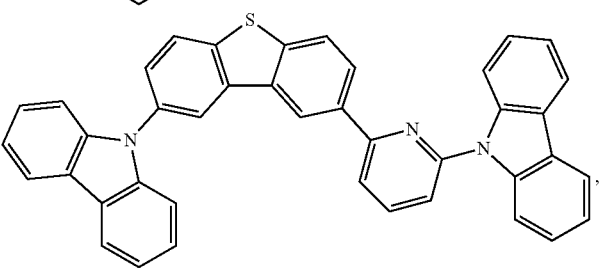
,

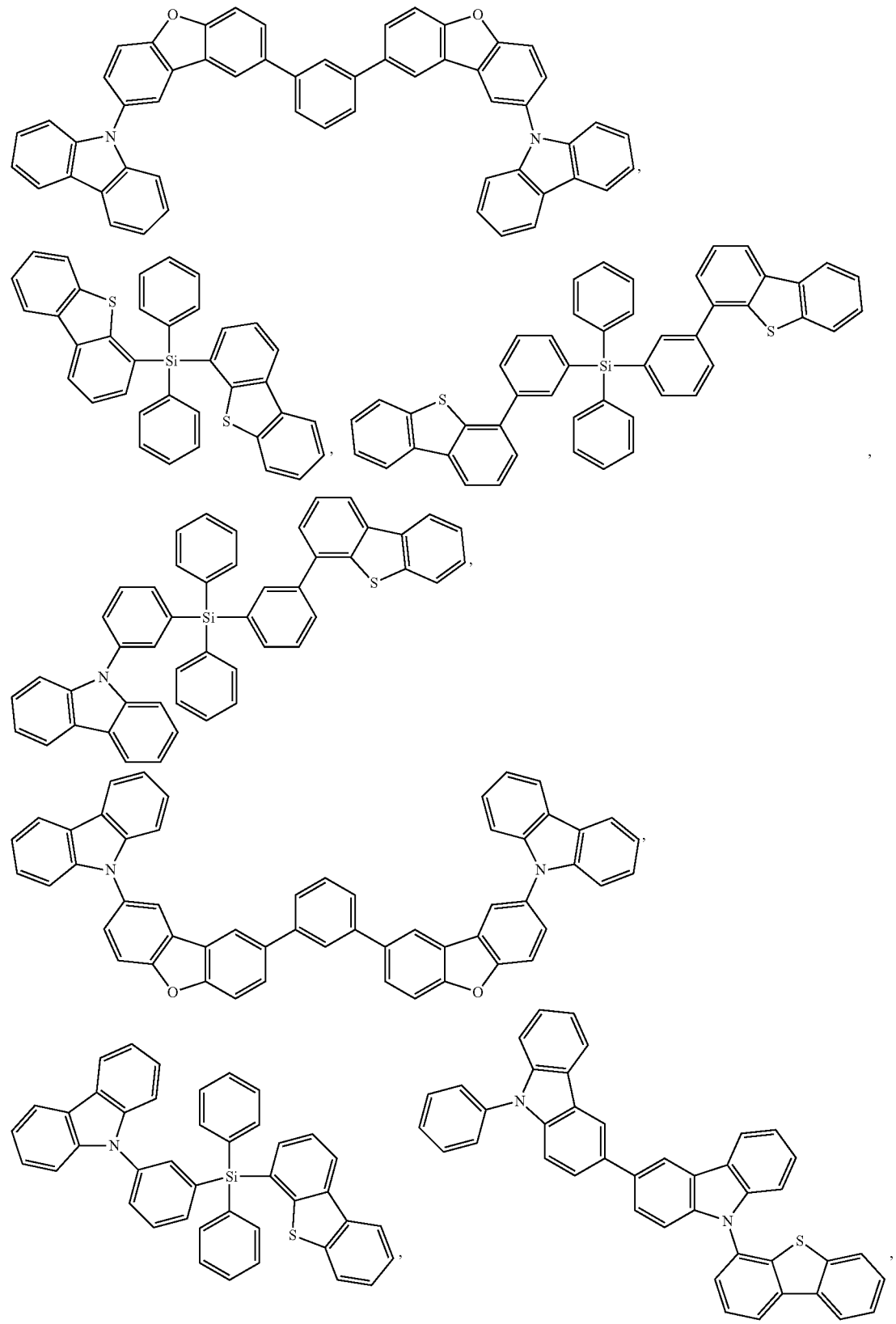

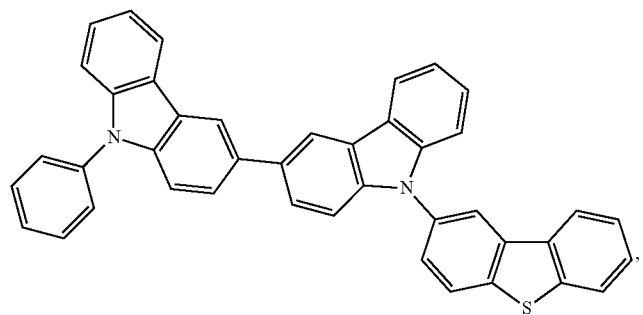
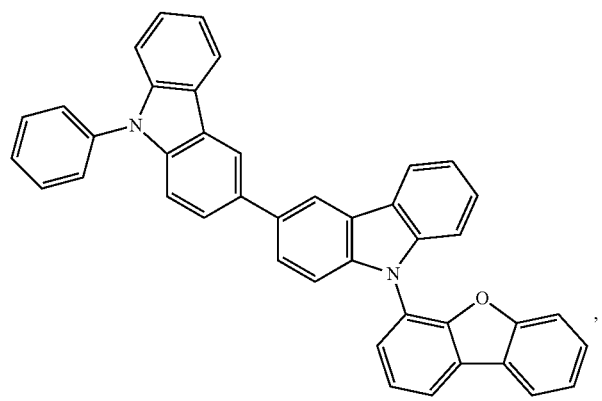
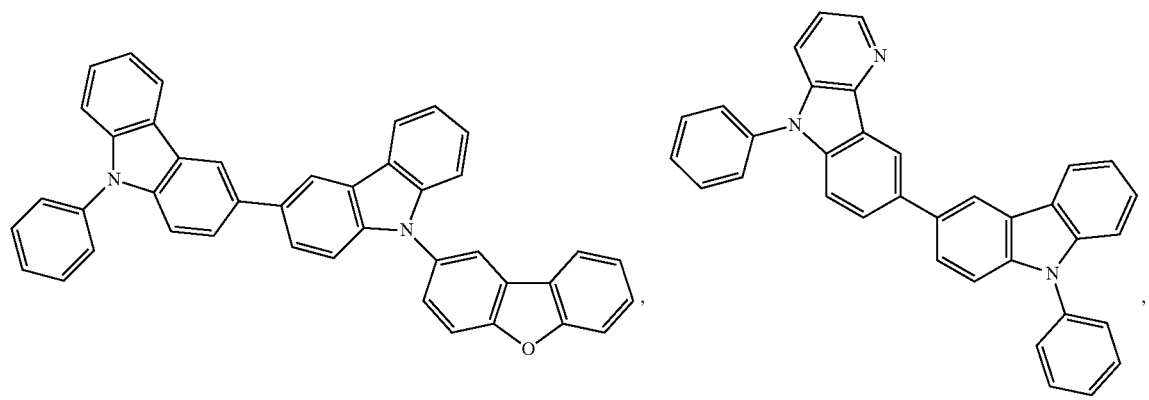
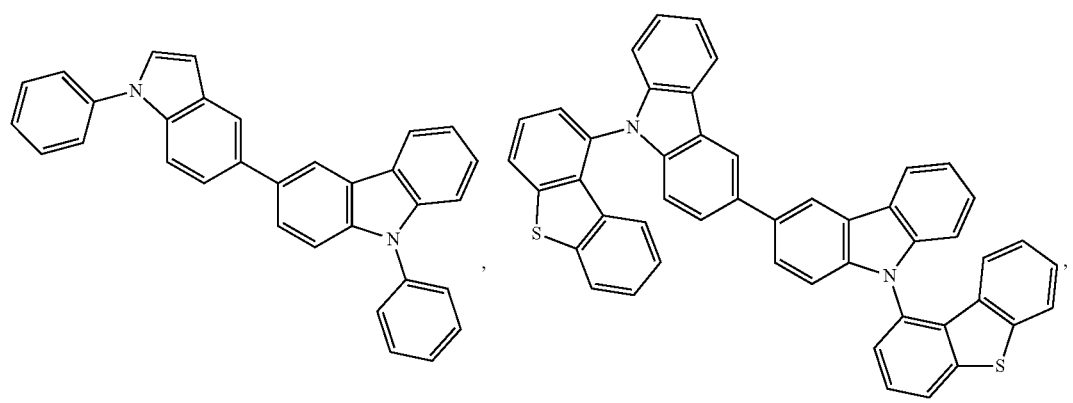

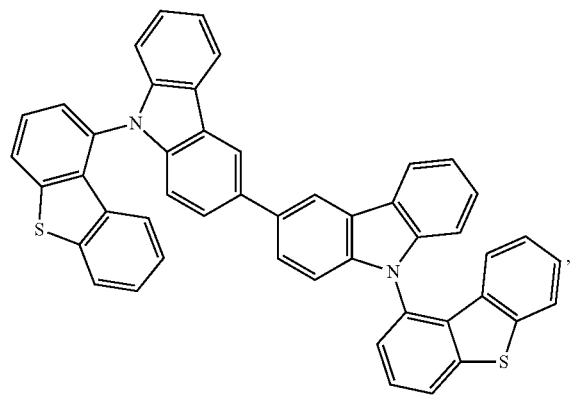
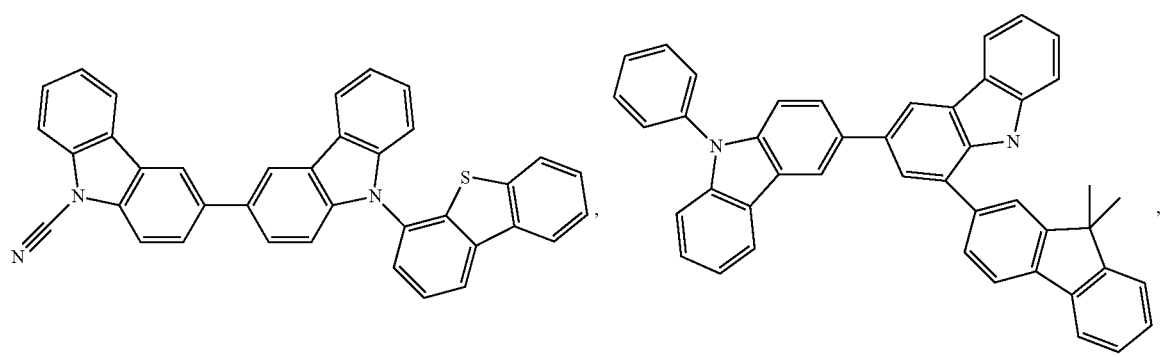
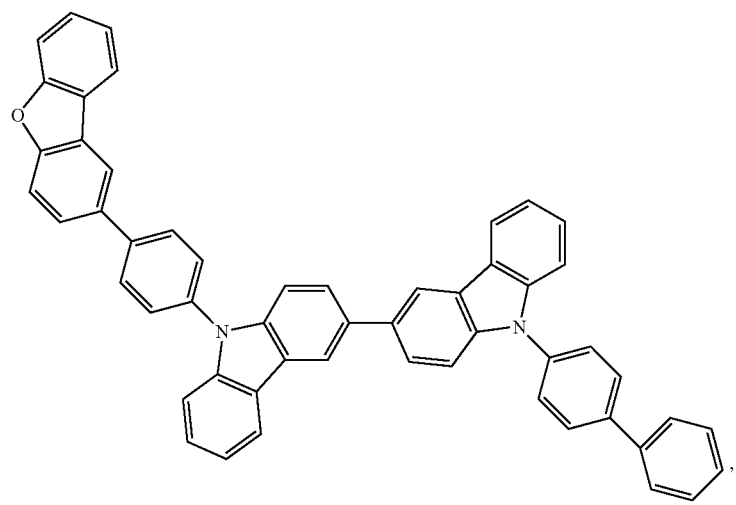

-continued
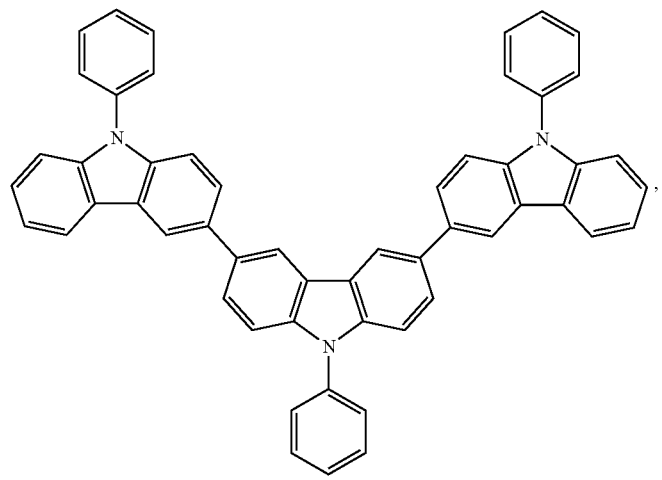
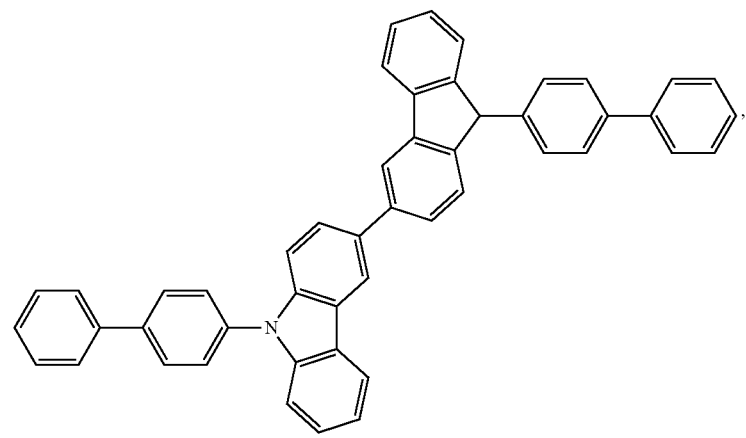
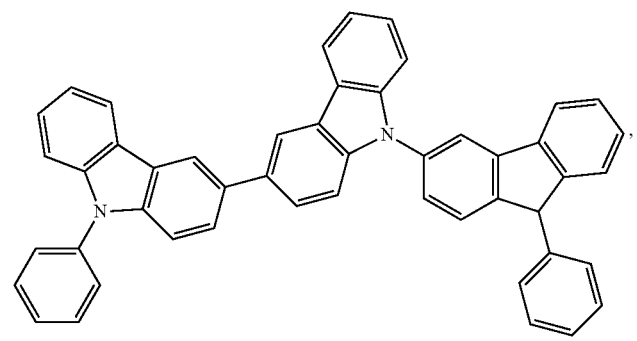

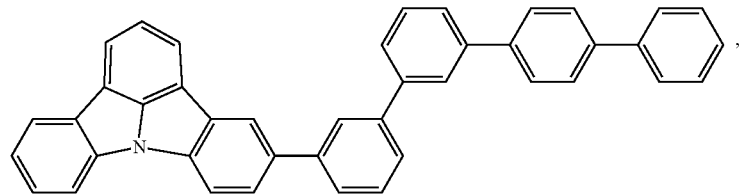
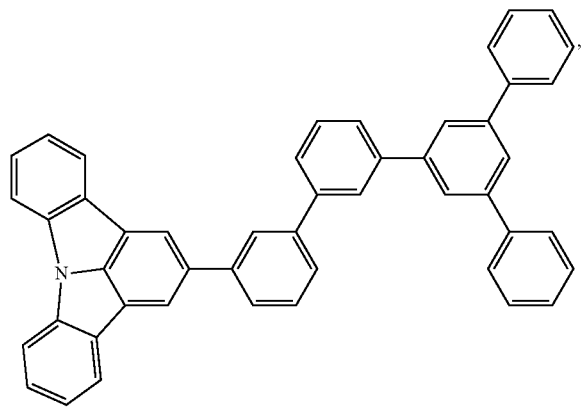
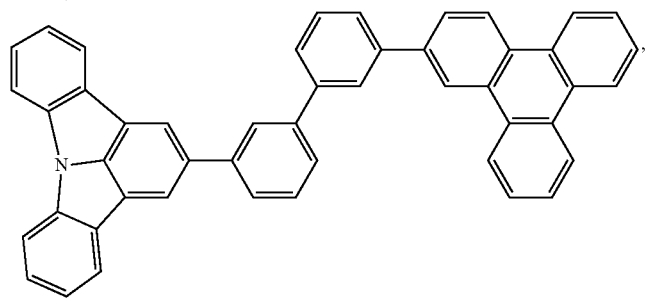
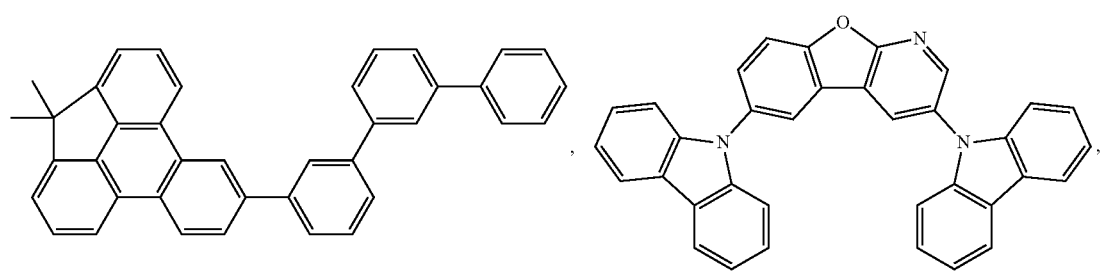
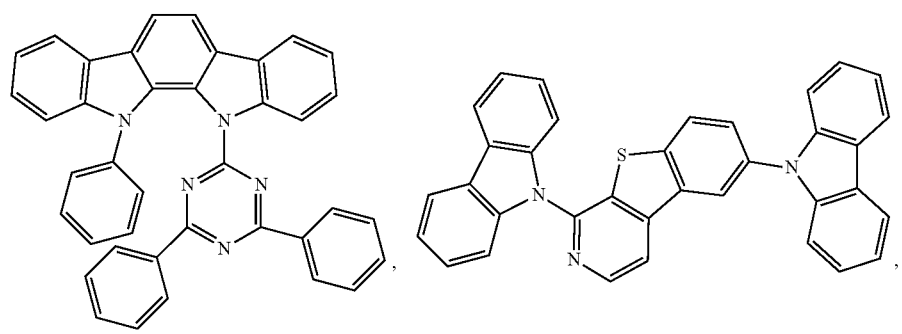

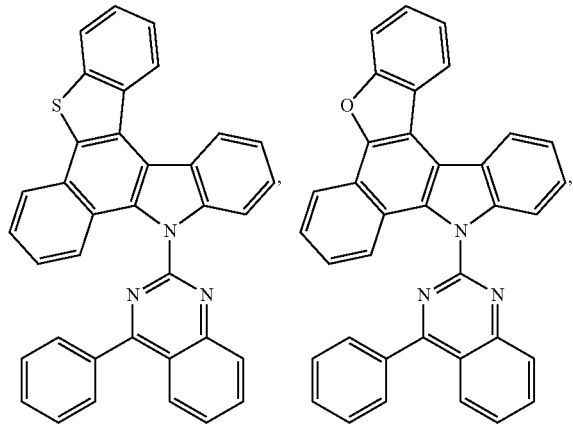
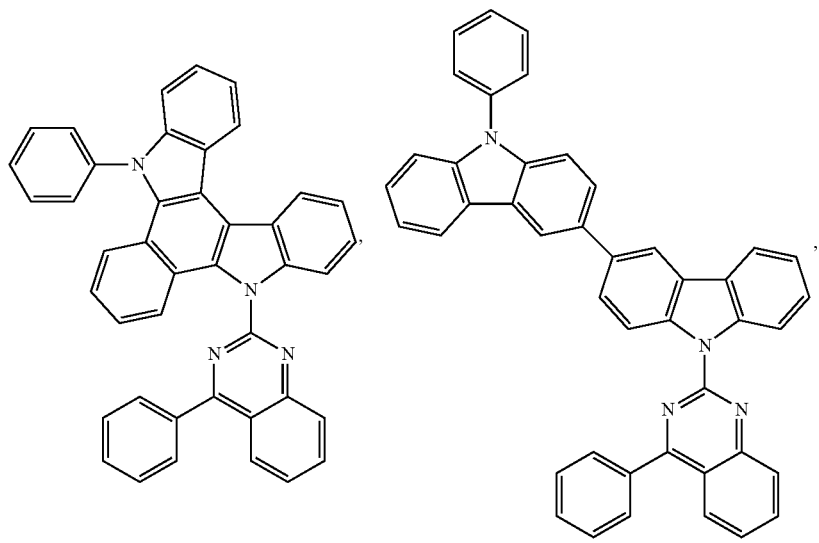
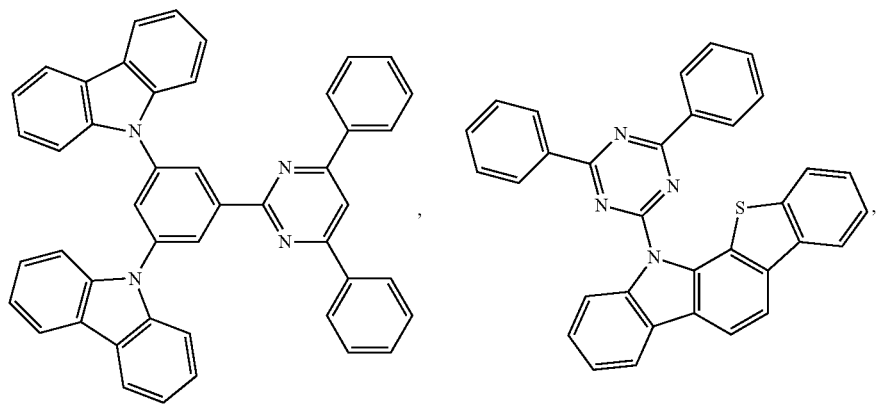

-continued
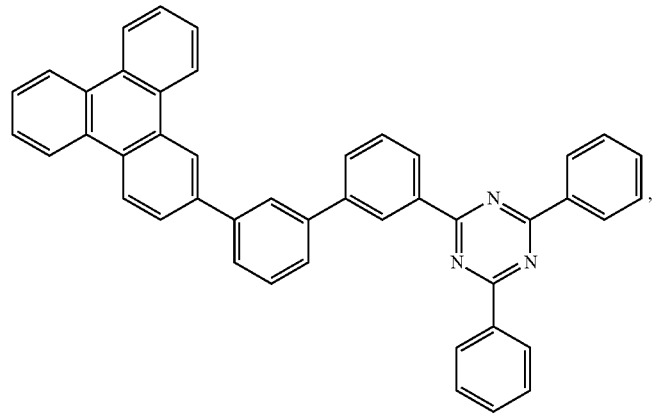
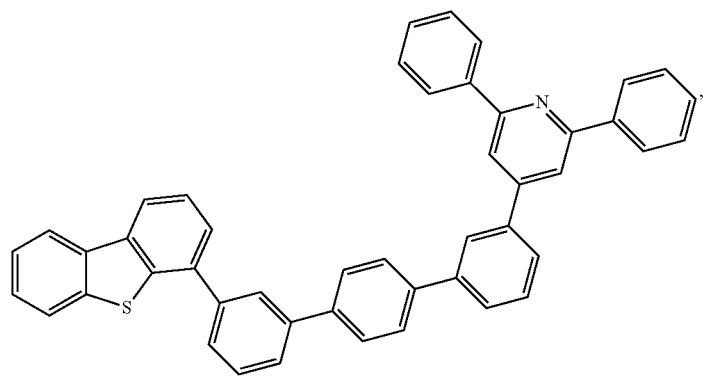
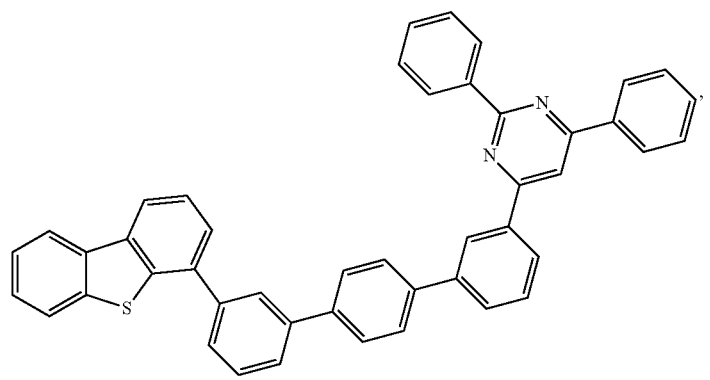
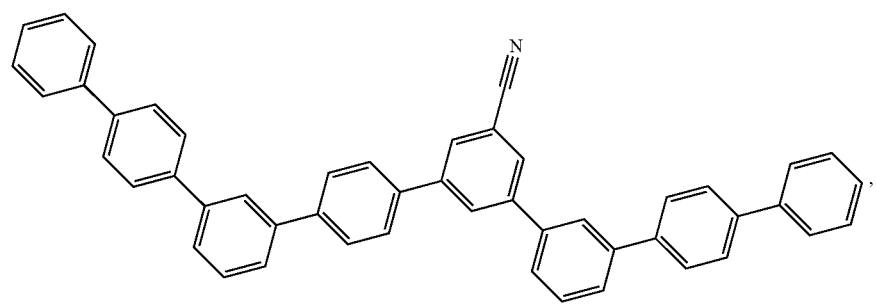

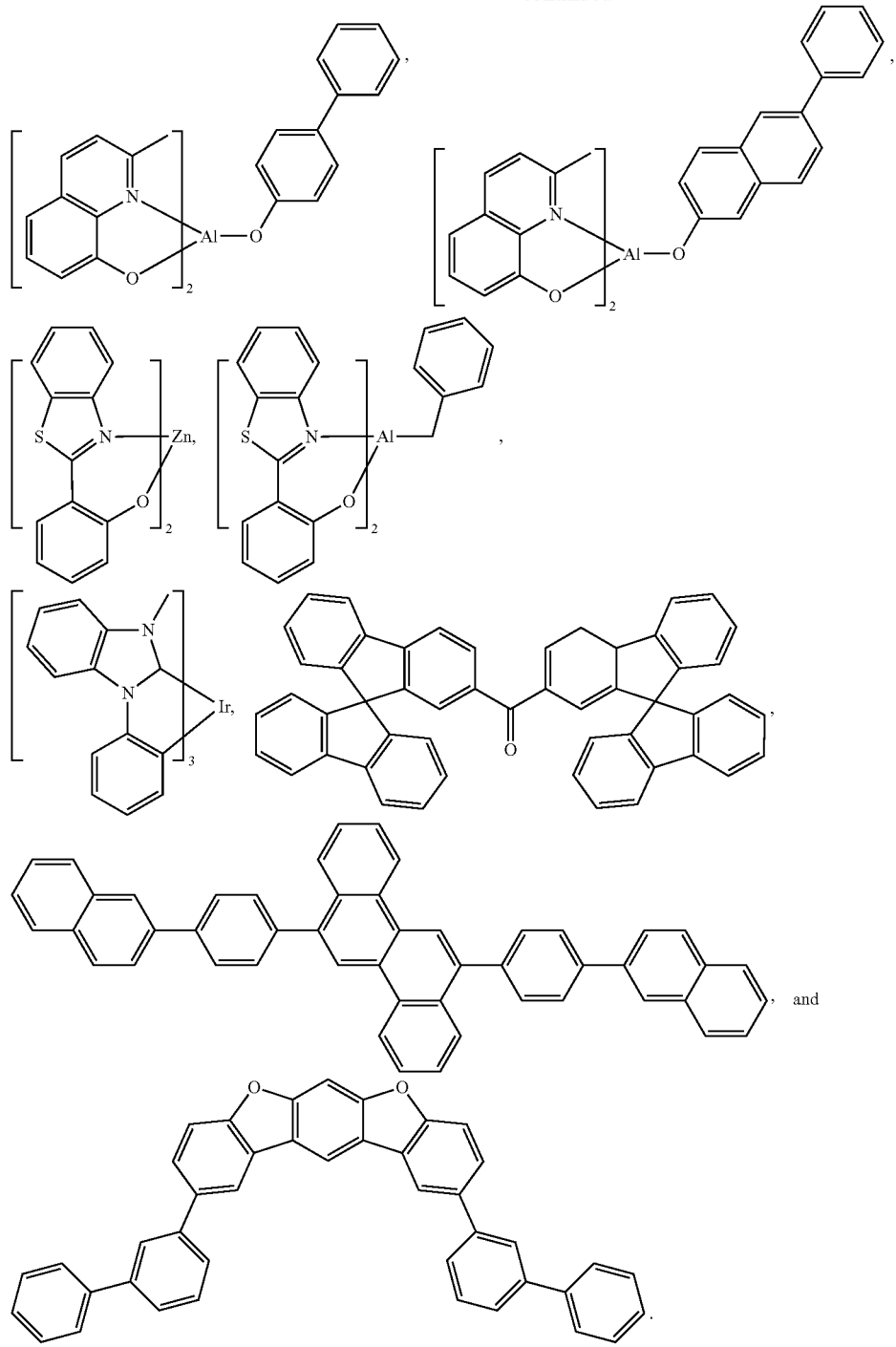

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.
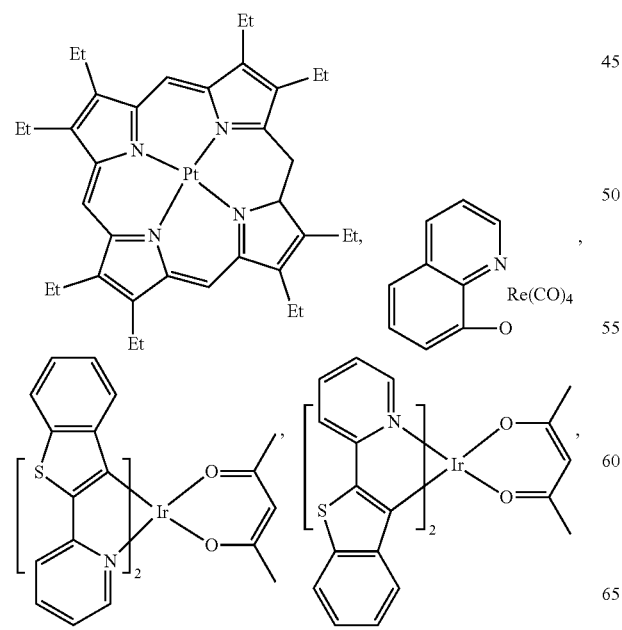
-continued
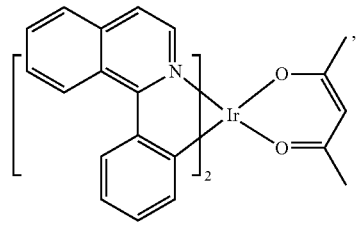
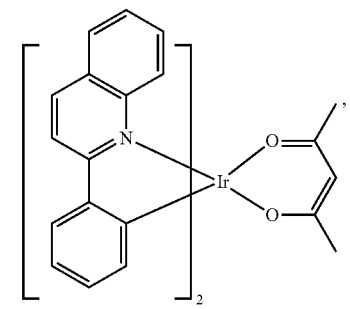
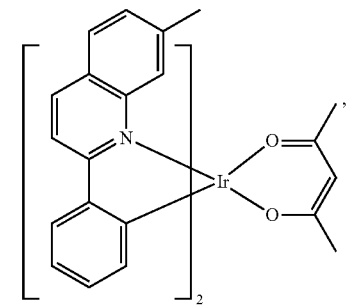
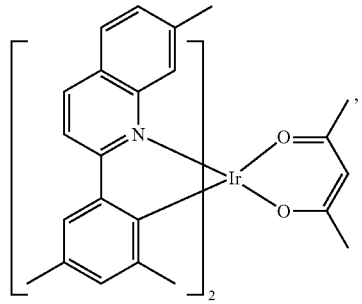
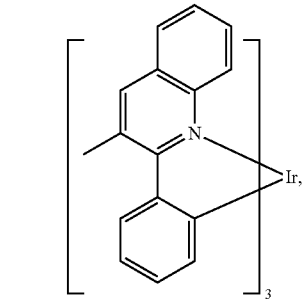

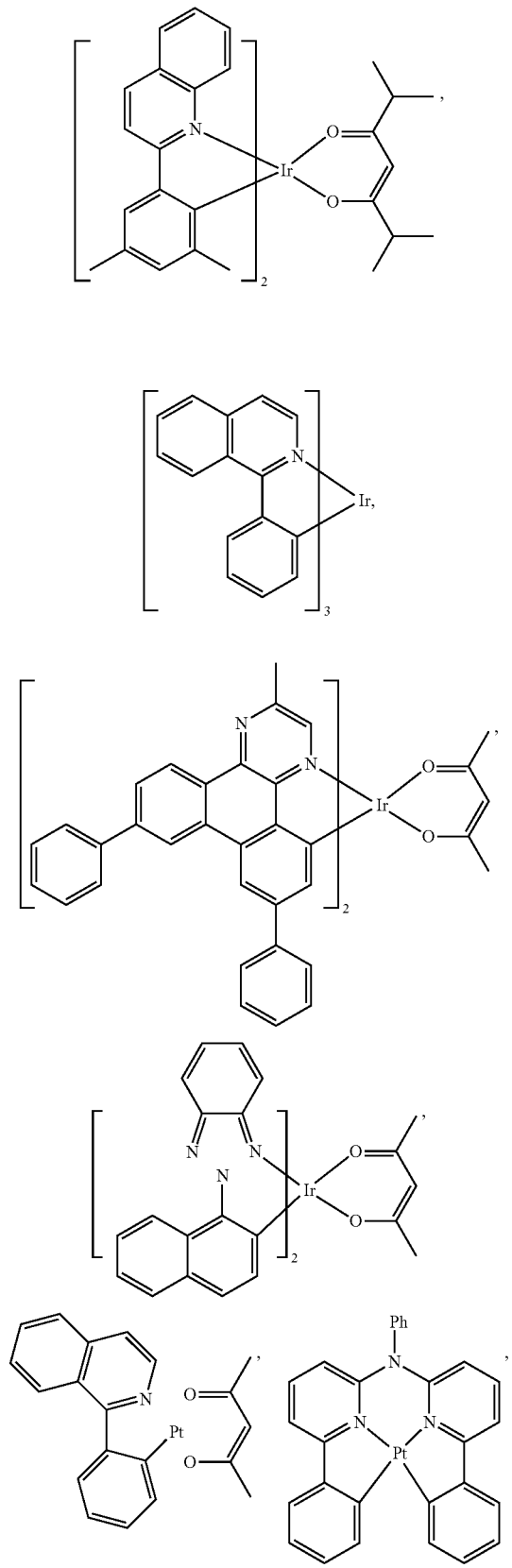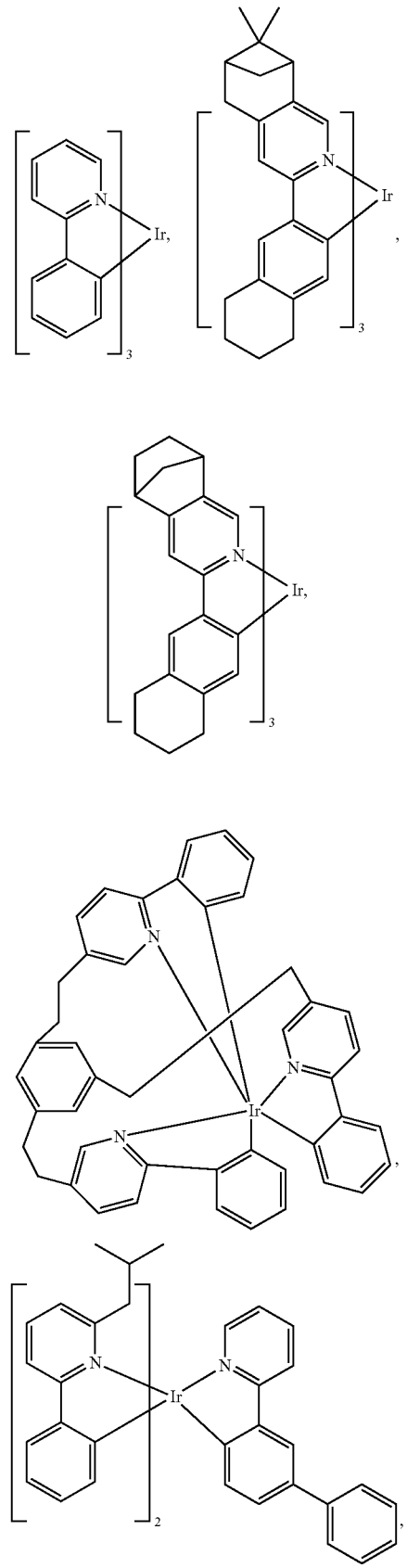

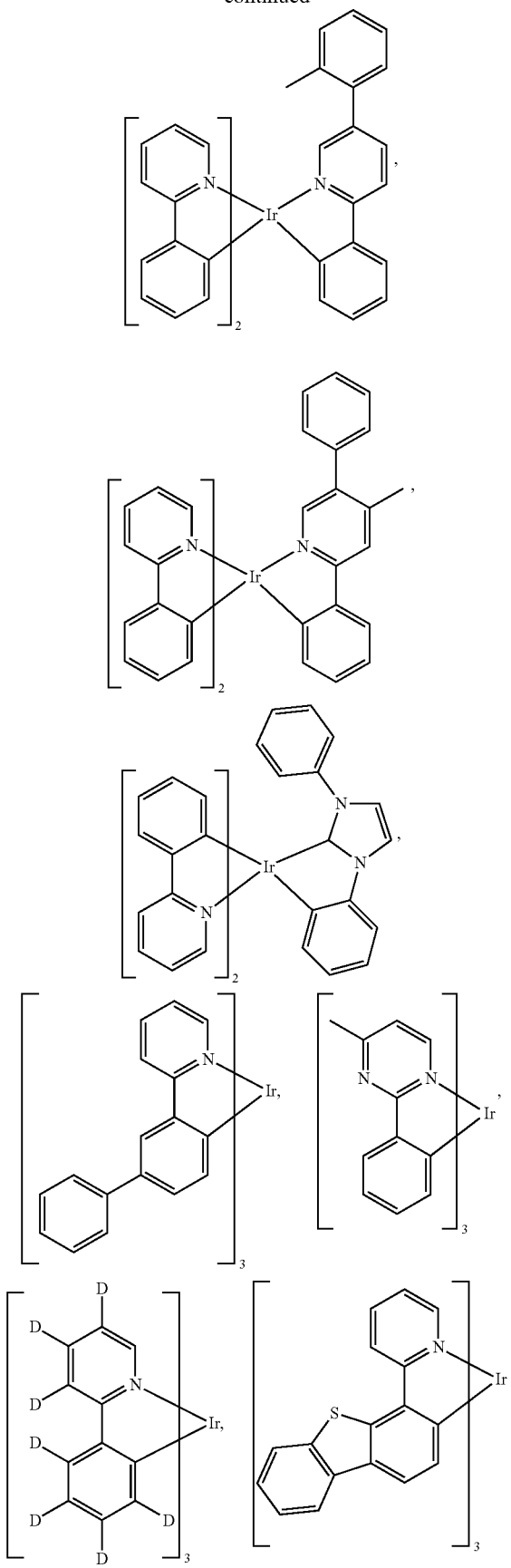
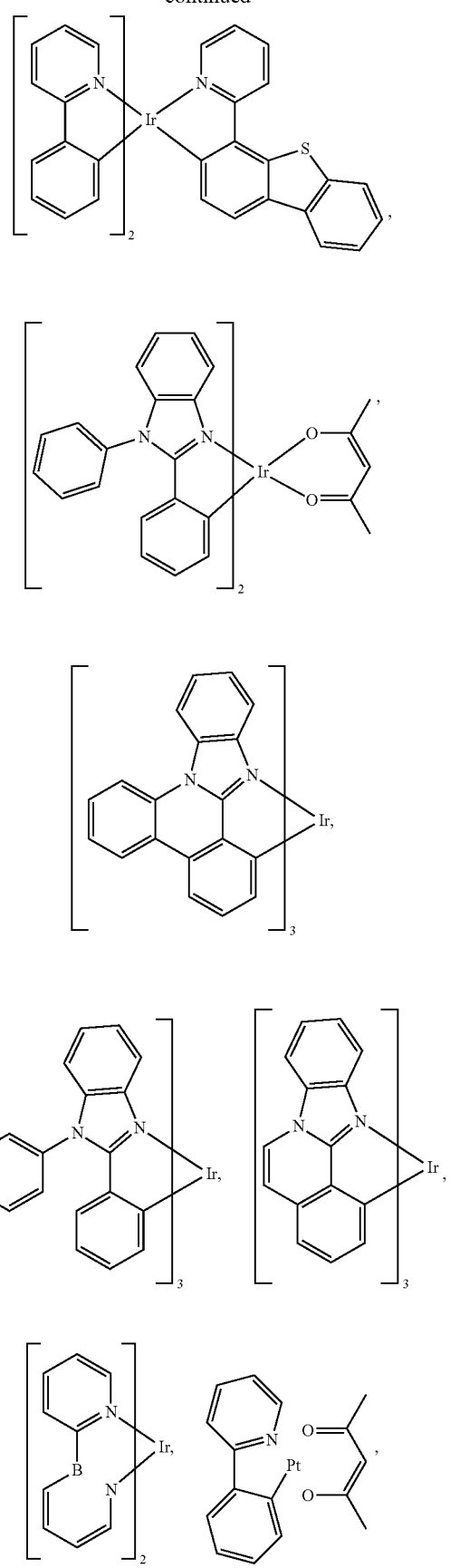

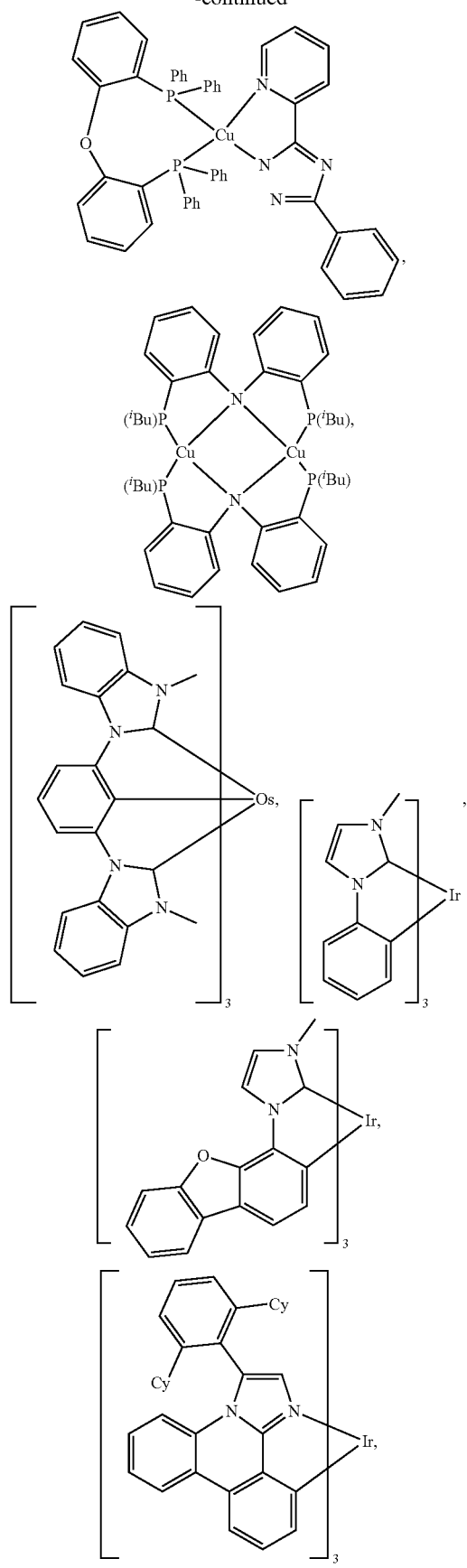
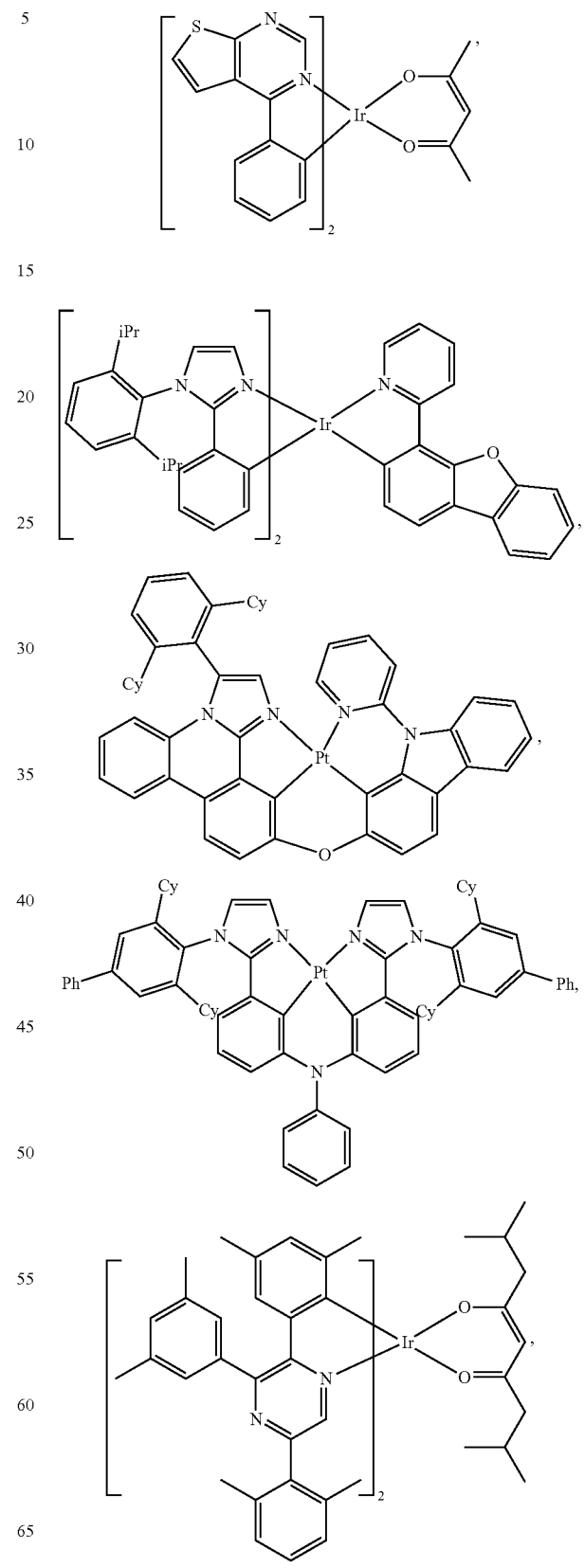

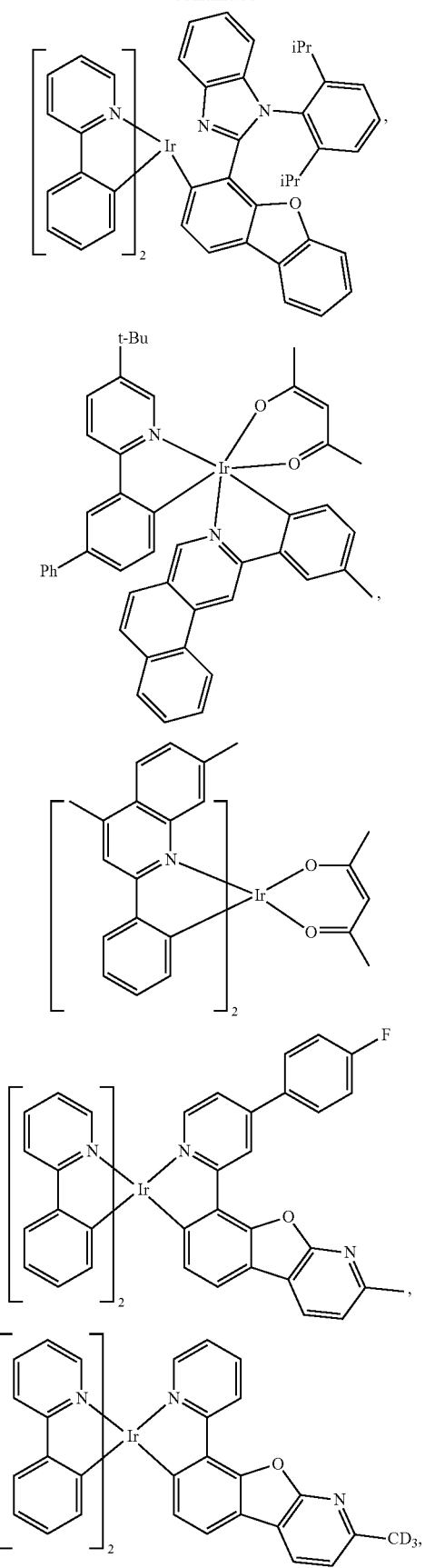
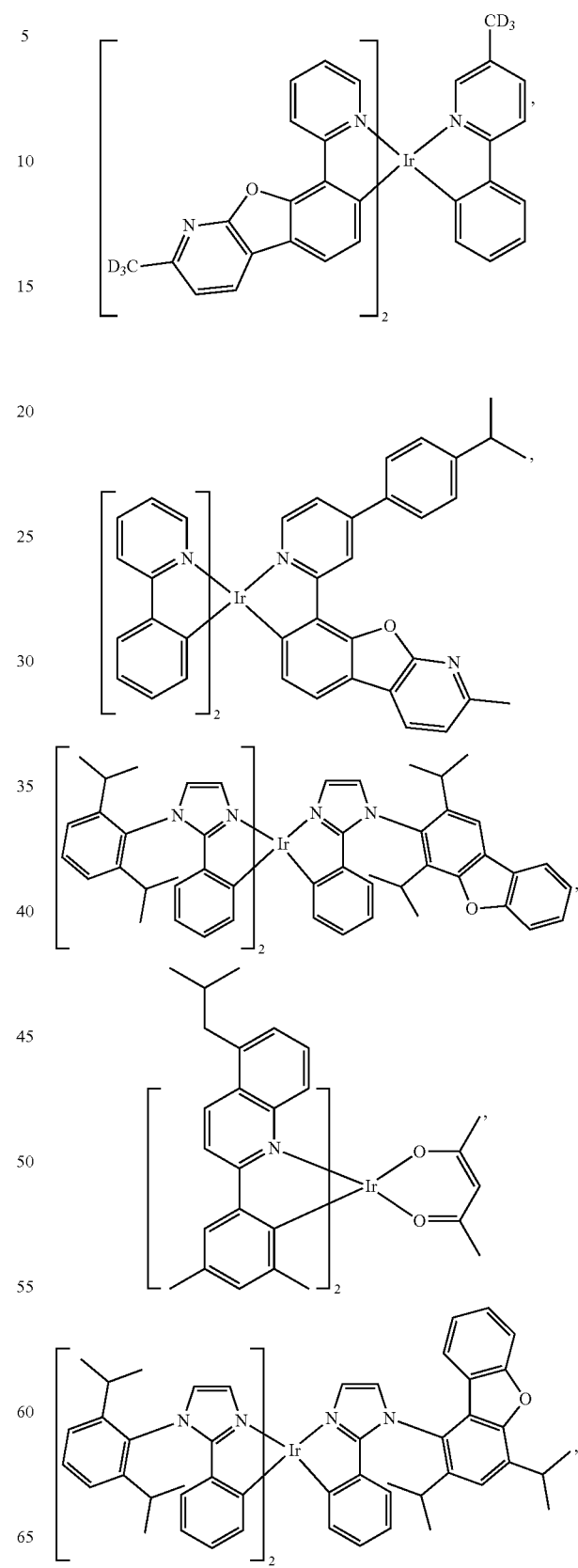

121
-continued
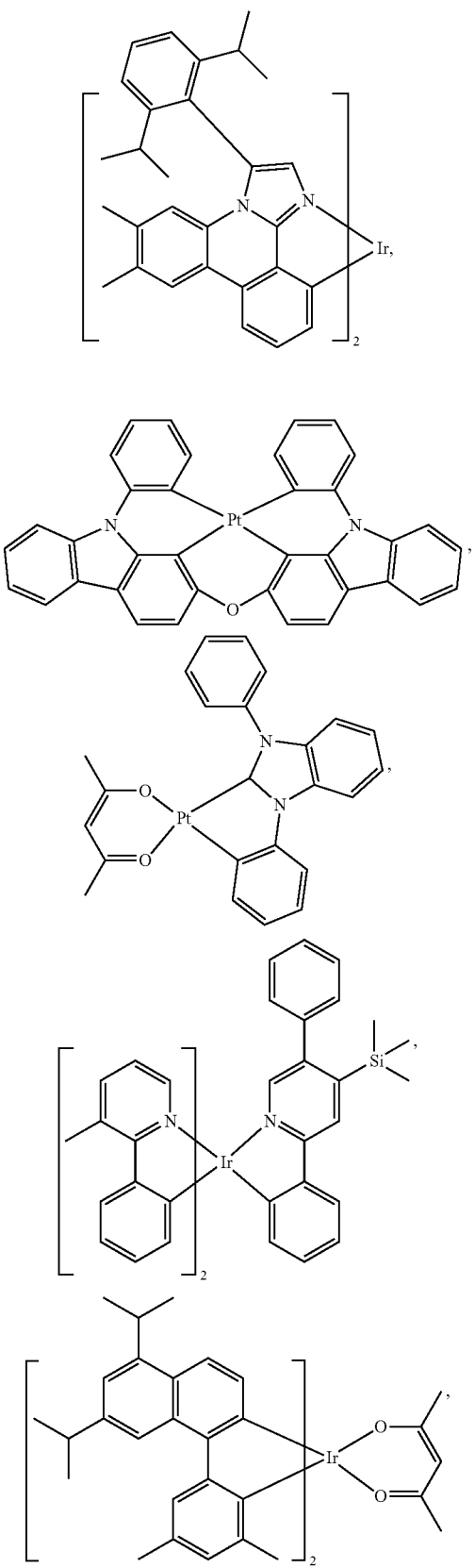
122
-continued
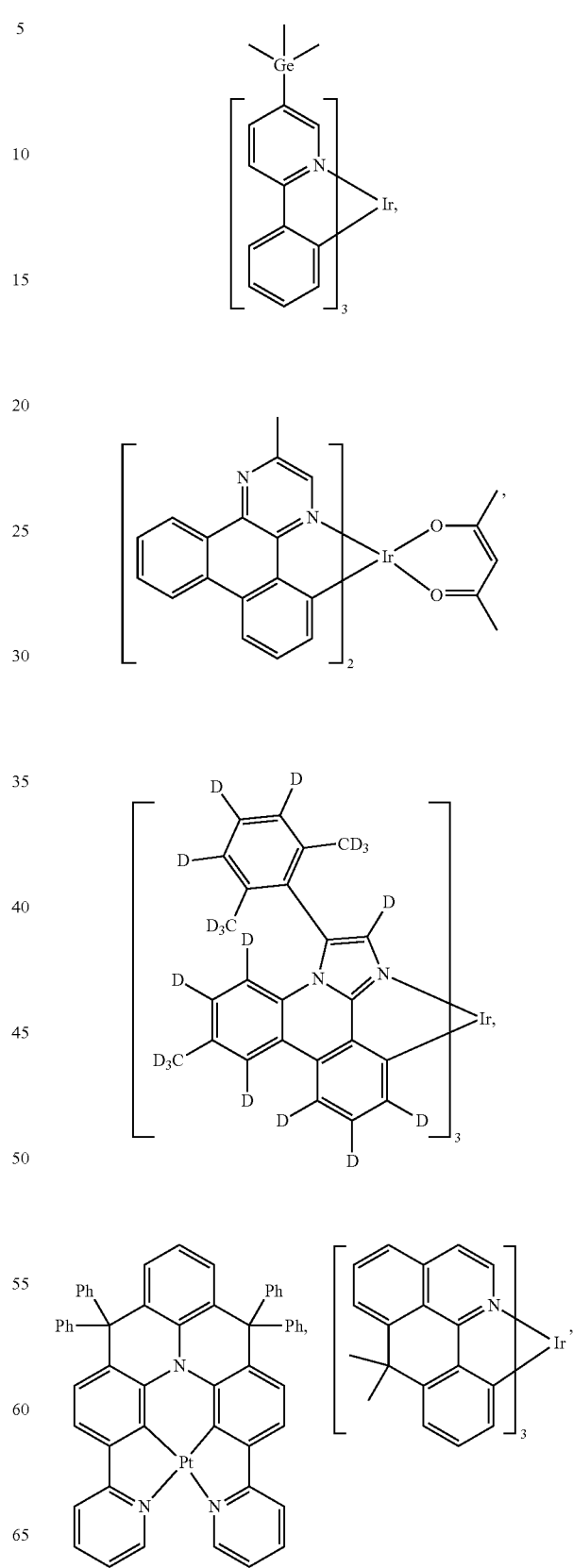

123
-continued
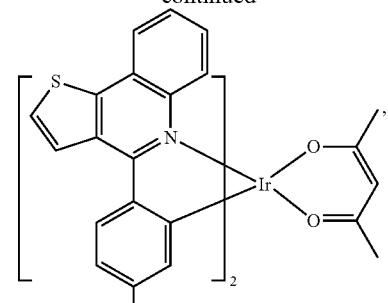
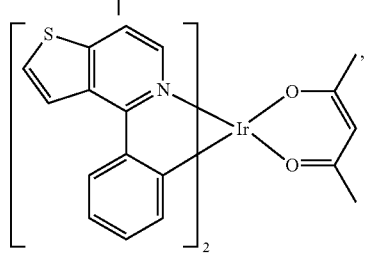
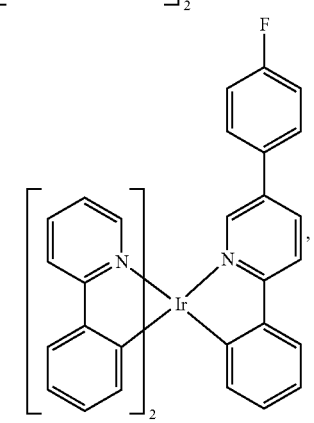
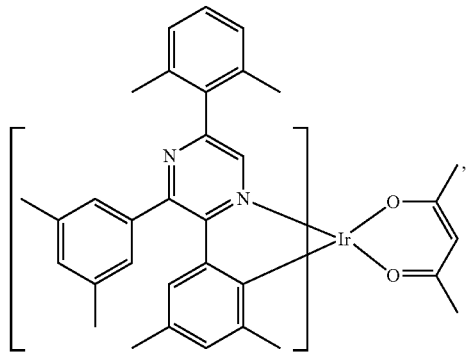
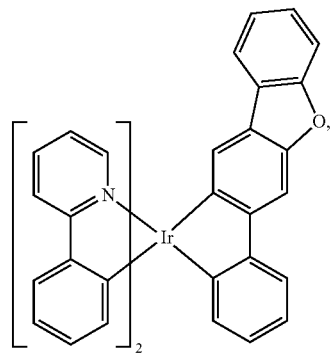
124
-continued
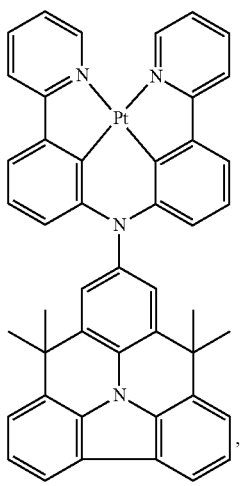
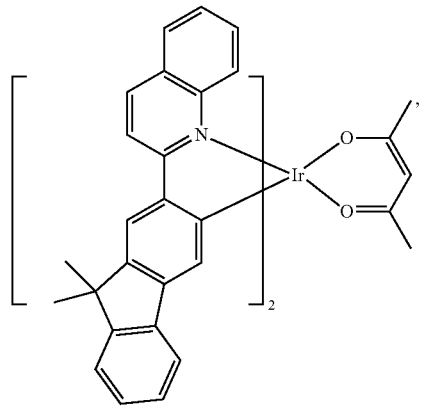
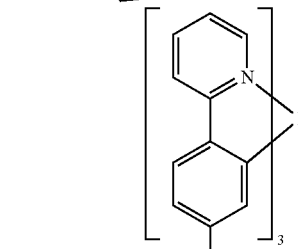
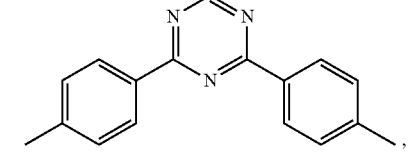
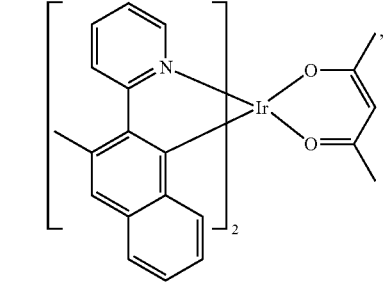

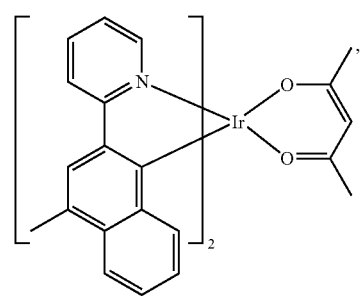
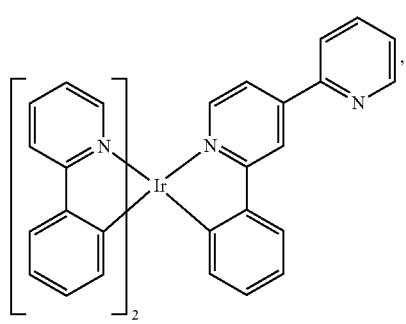
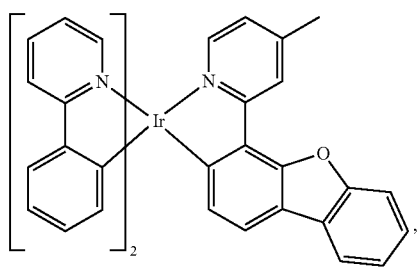
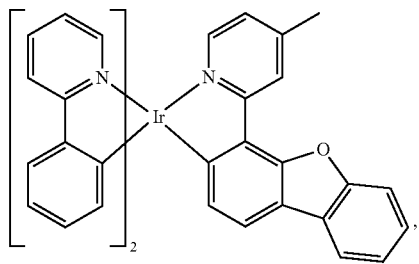
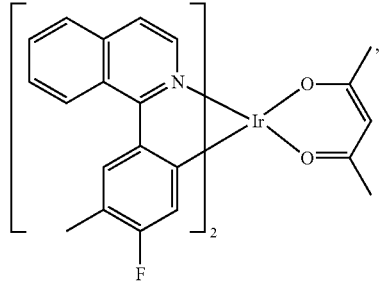
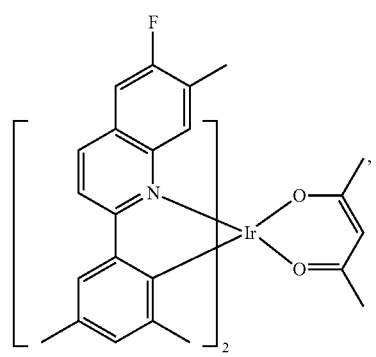
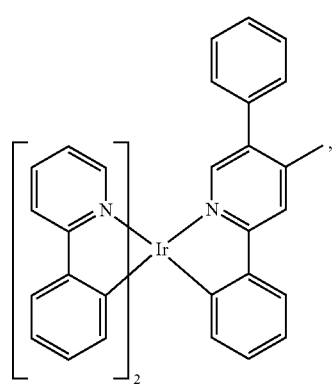
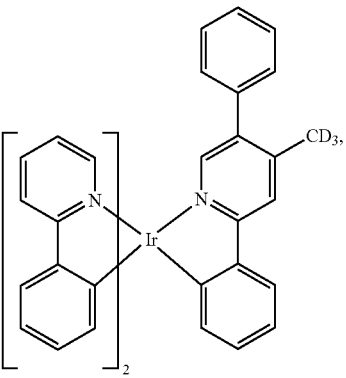
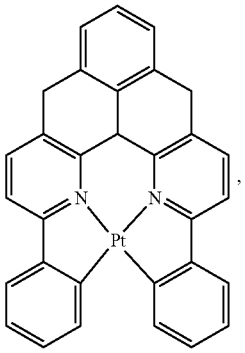

127
-continued
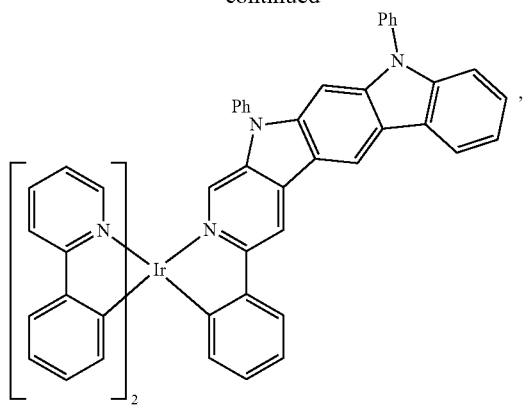
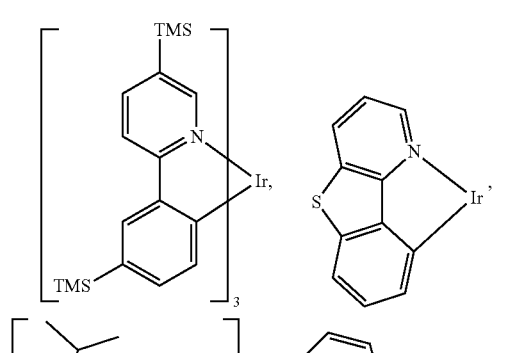
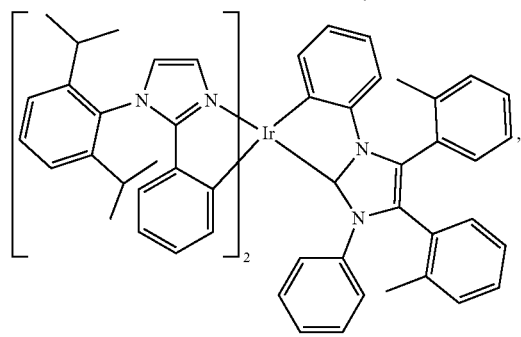
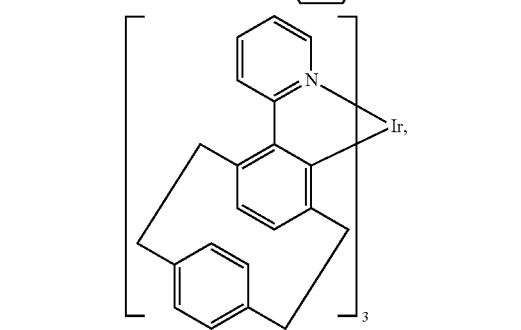
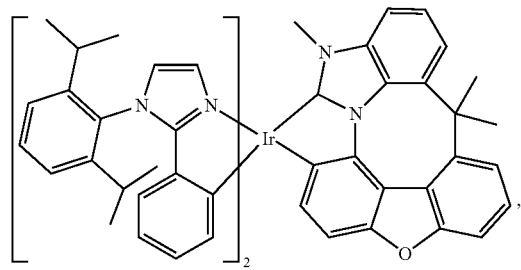
128
-continued
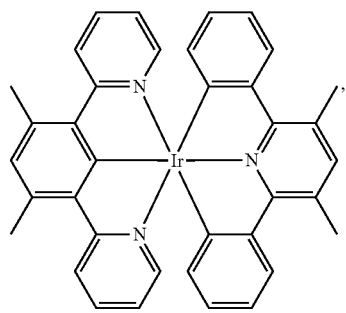
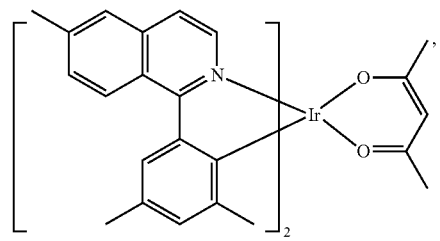
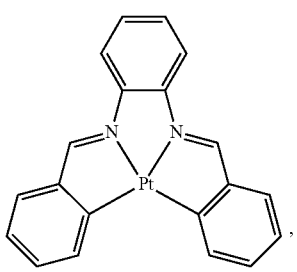
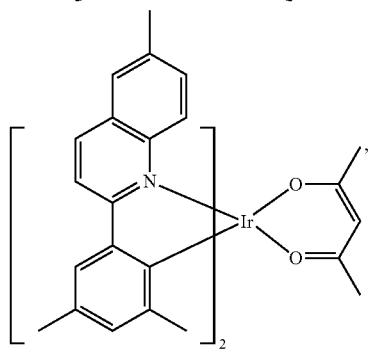
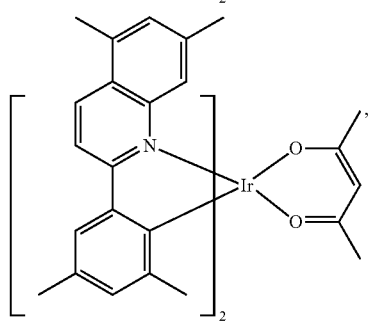

129
-continued
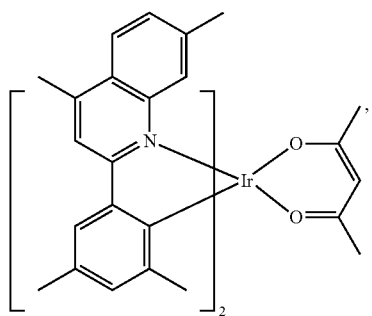
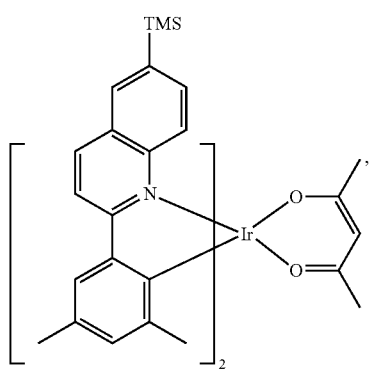
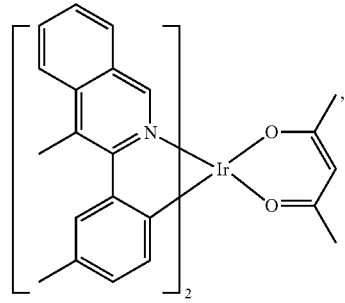
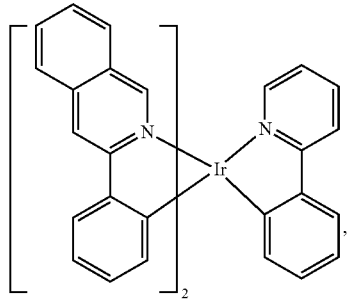
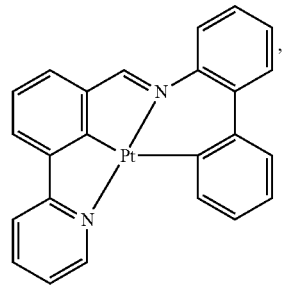
130
-continued
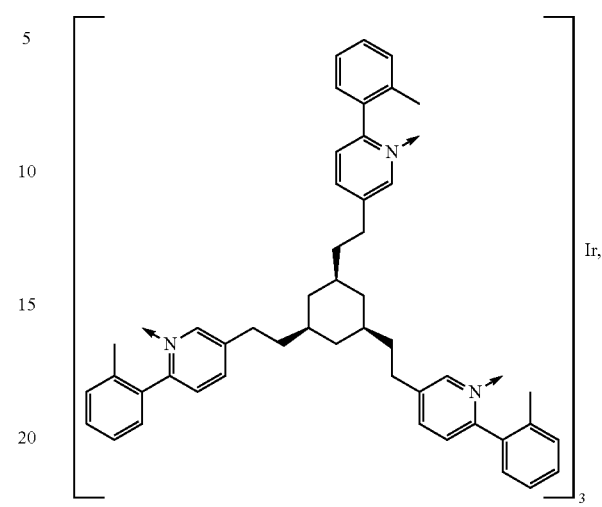
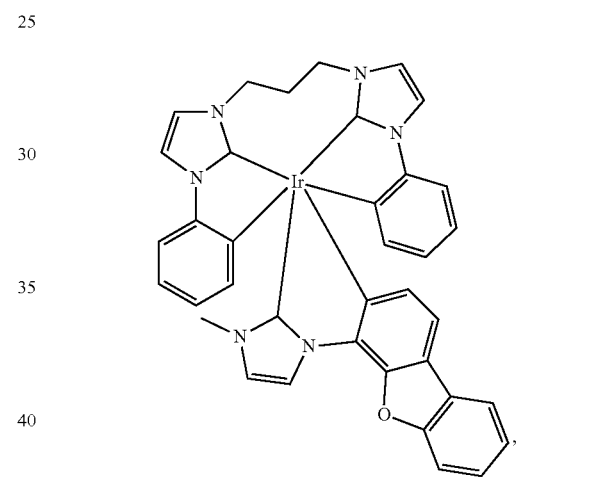
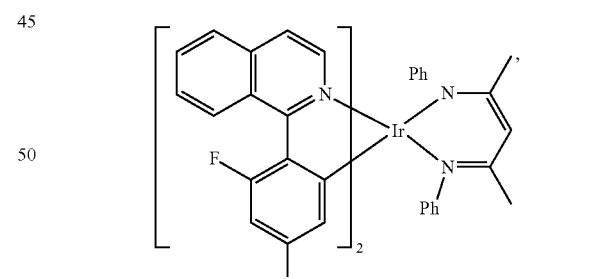
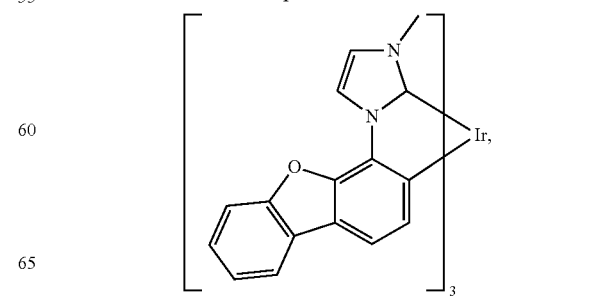

131
-continued
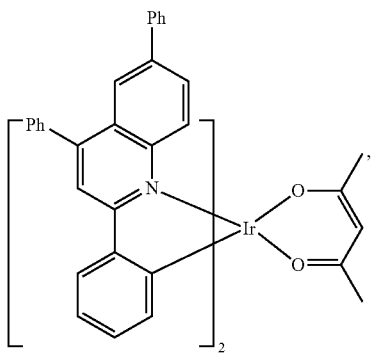
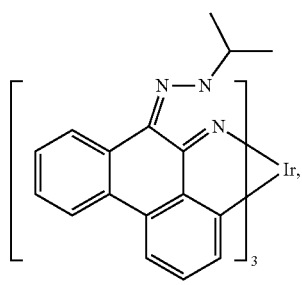
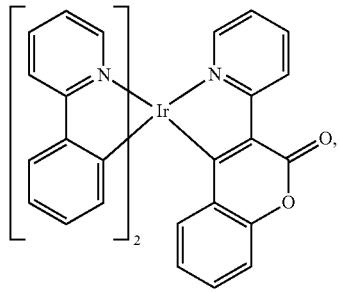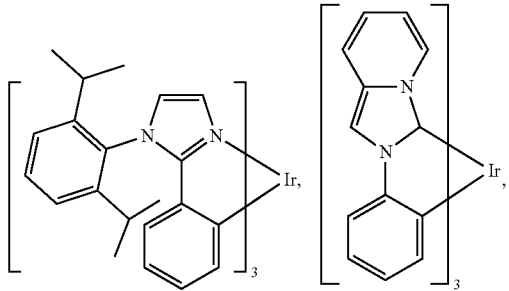
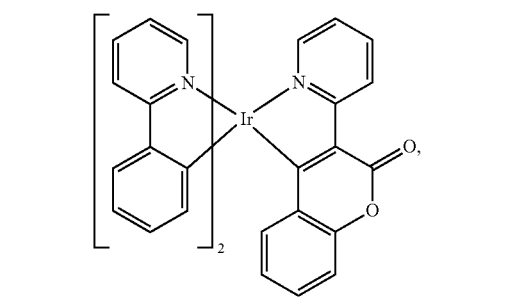
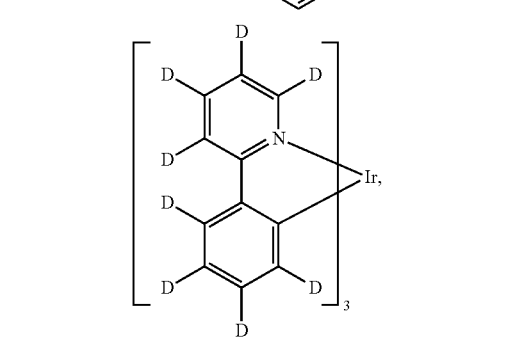
132
-continued
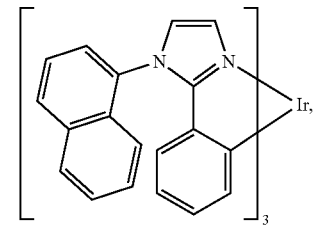
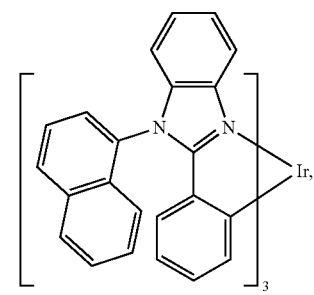
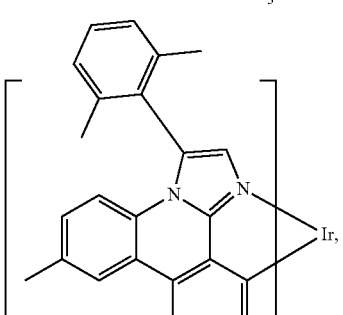
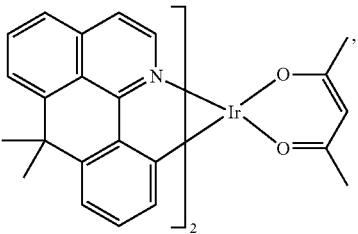
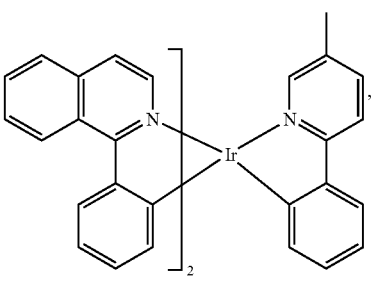
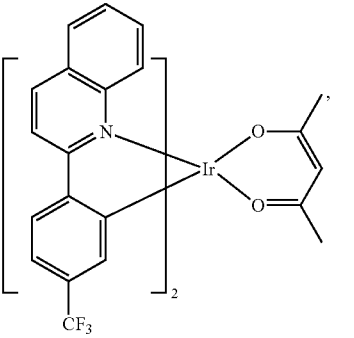

-continued

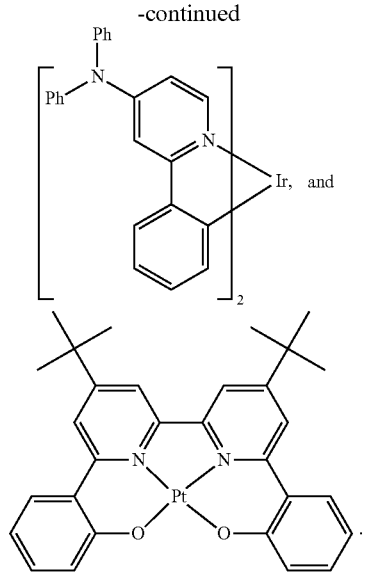

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

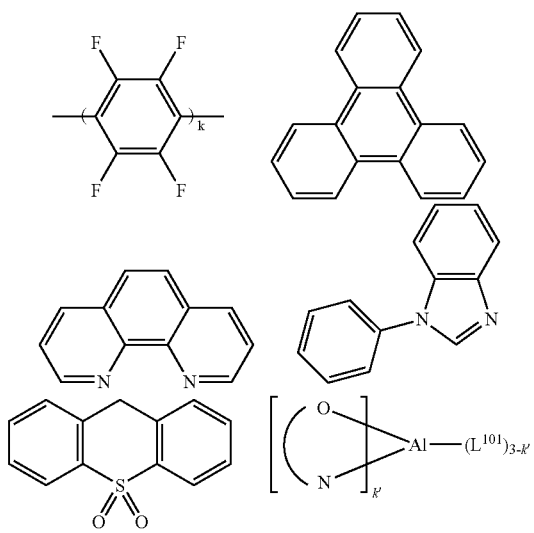

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

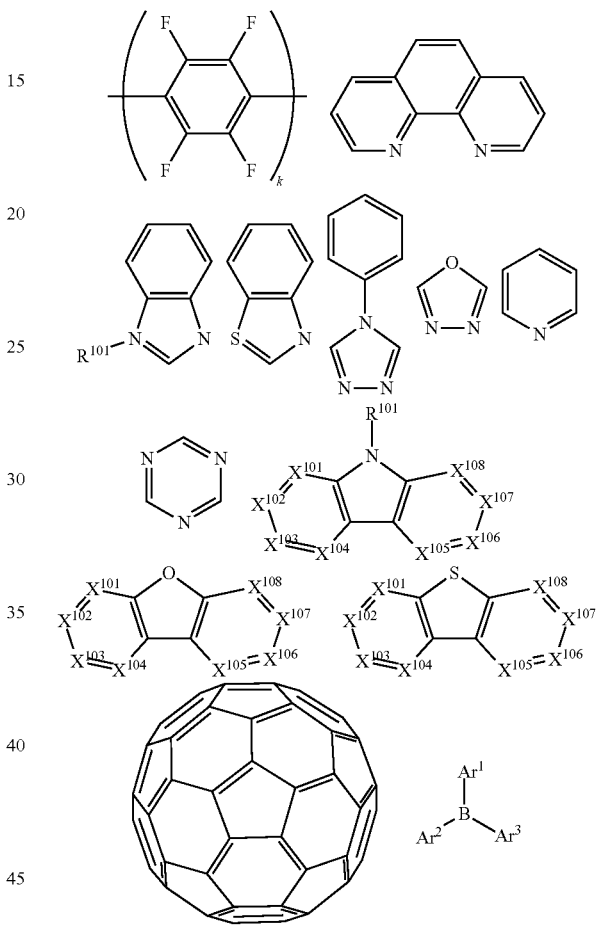

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

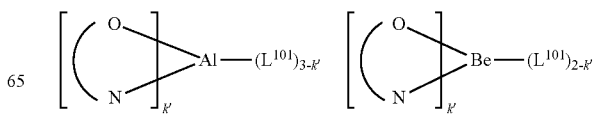

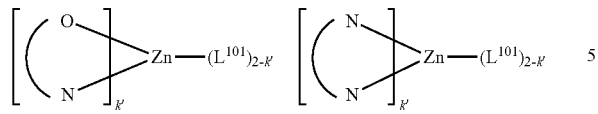

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

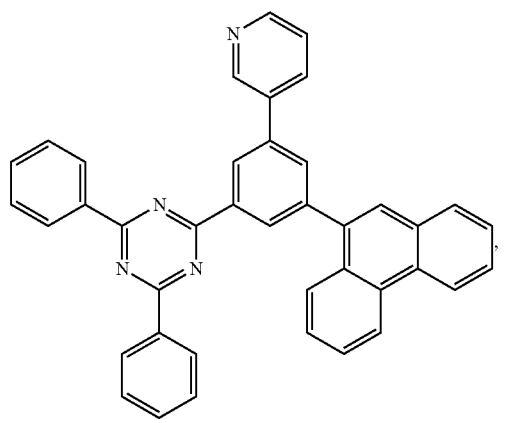

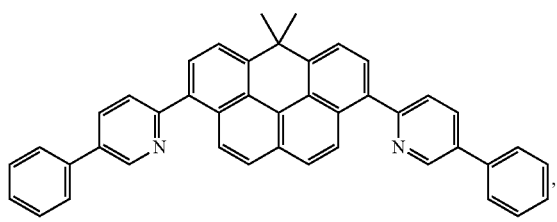

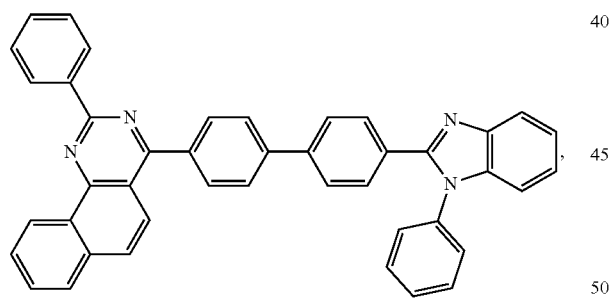

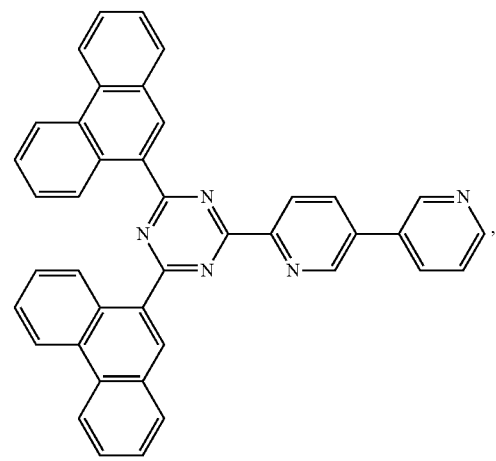

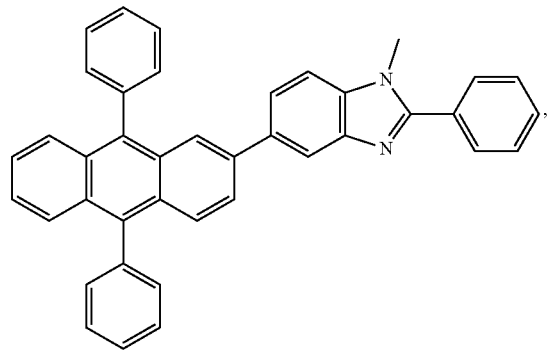

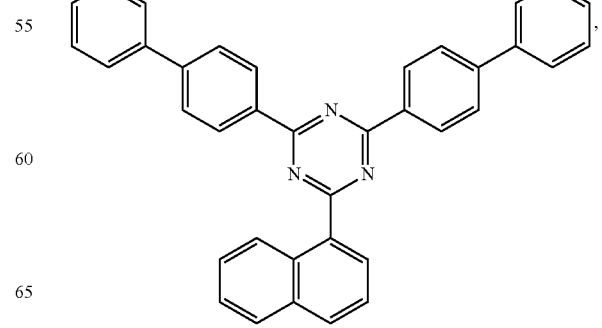

137
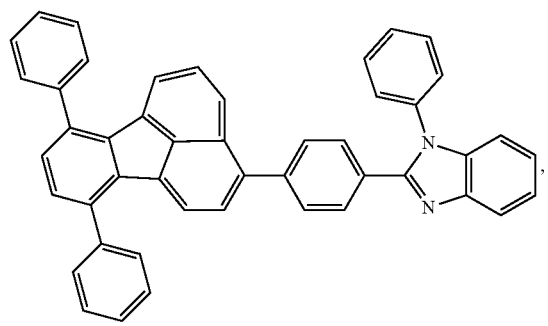
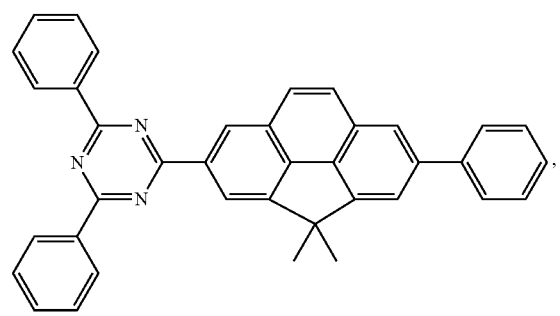
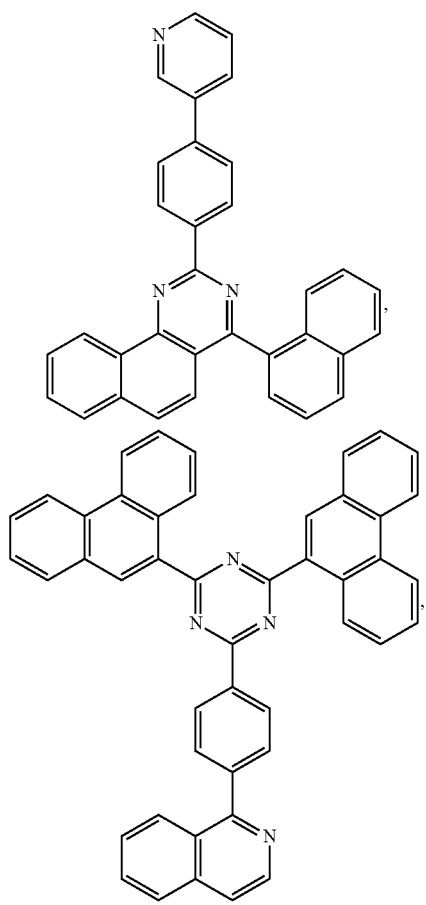
138
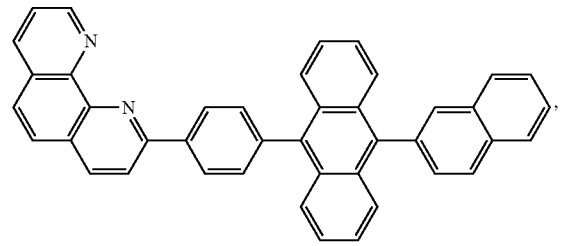
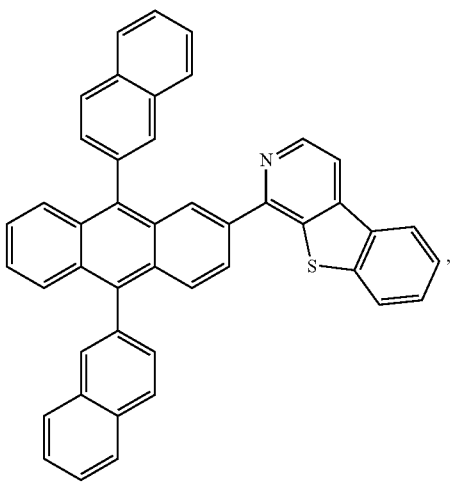
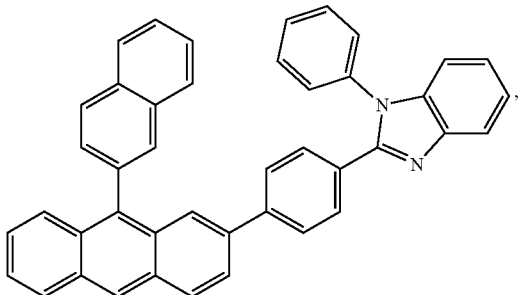
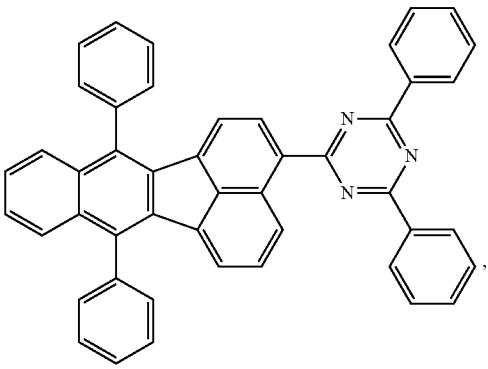

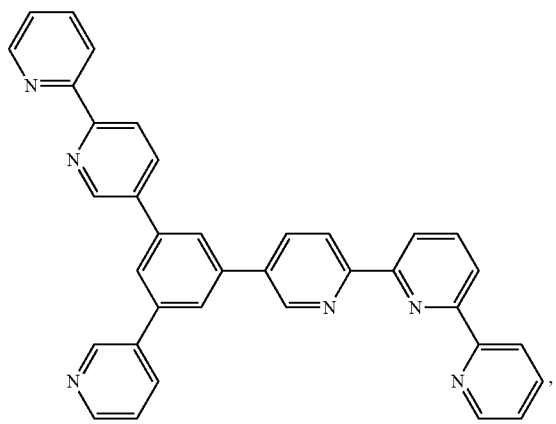
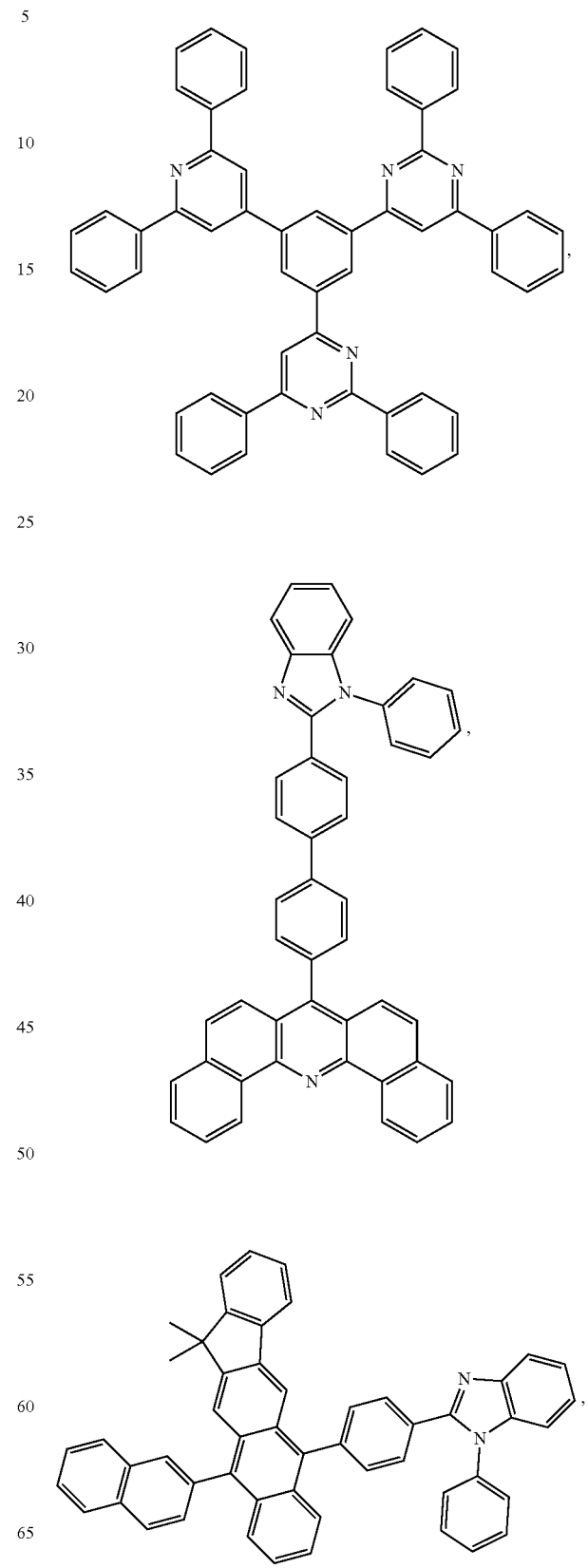

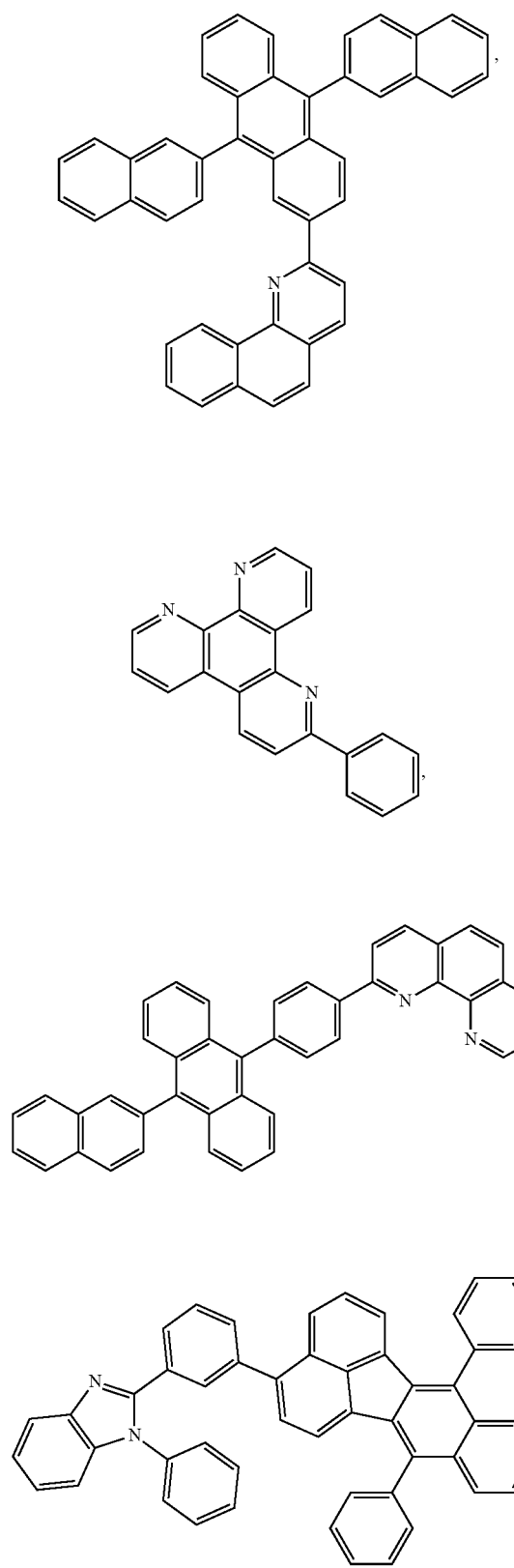
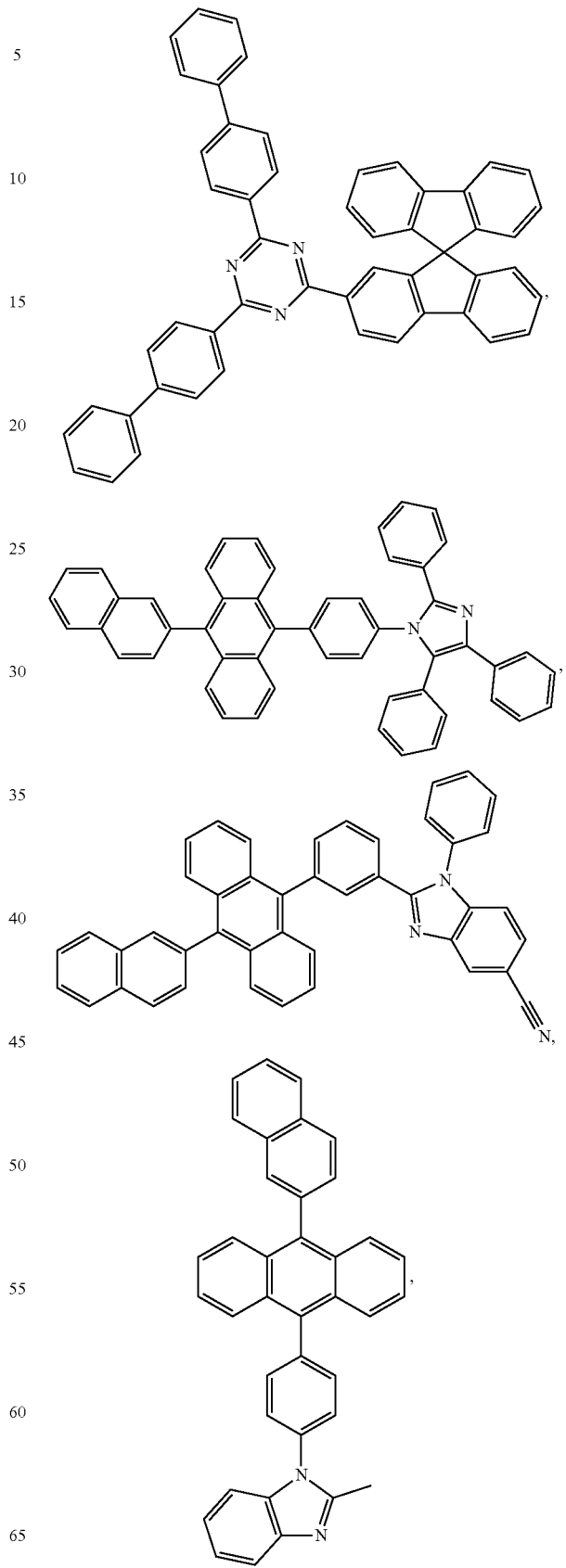

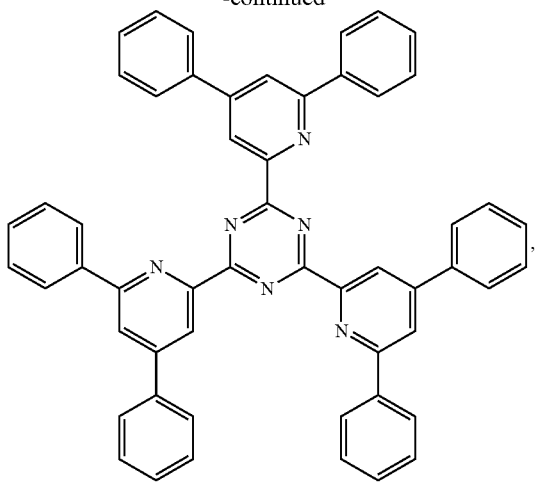

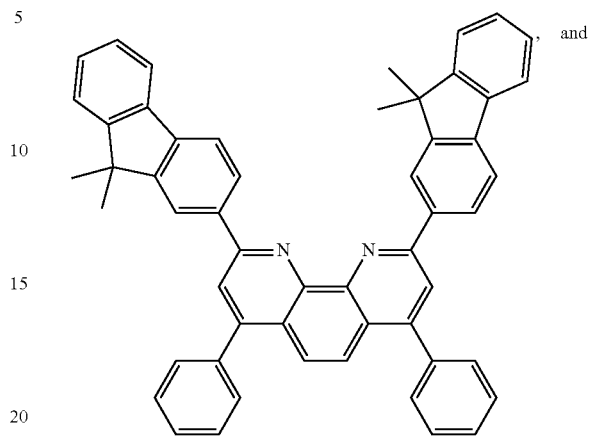

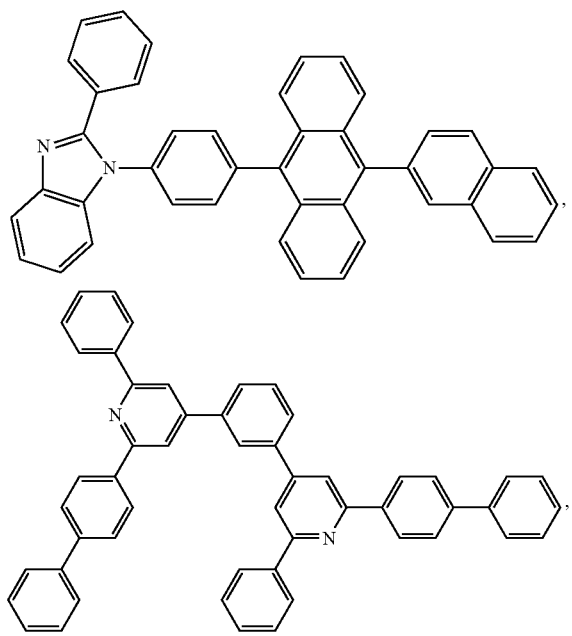

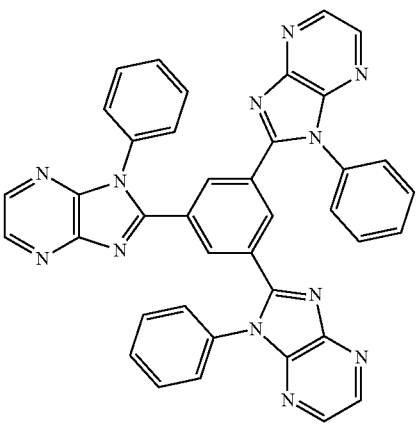

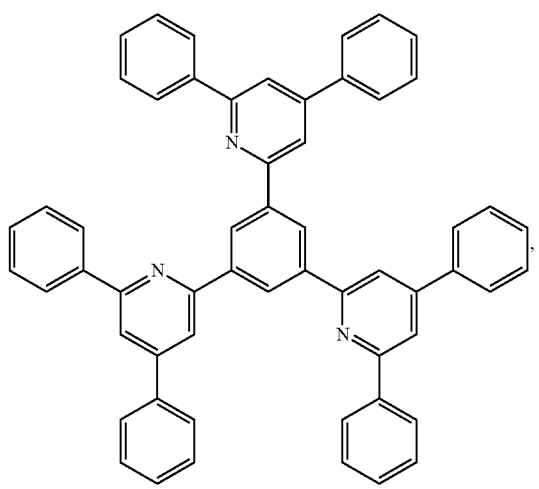

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

Synthetic scheme:

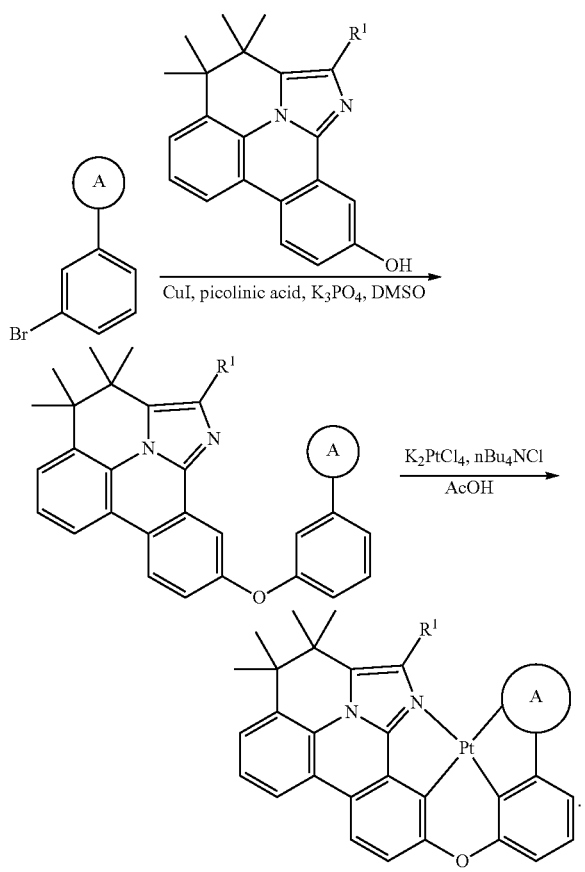

Synthesis of Compound 3

Synthesis 1-(3-bromophenyl)-2-((2,6-diisopropylphenyl)amino)ethan-1-one

A mixture of 2-bromo-1-(3-bromophenyl)ethan-1-one (3 g, 10.79 mmol) and 2,6-diisopropylaniline (4.02 g, 22.67 mmol) was stirred in ethanol (15 ml) at R.T. for 2 days. Ethanol was then removed and the mixture was triturated in diethyl ether. The resulting white solid (salt) was removed by filtration. The filtrate was concentrated and chromatographed on silica (THF/Hep=1/20) to obtain yellow oil (3 g, 74%).

Synthesis of 4-(3-bromophenyl)-1-(2,6-diisopropylphenyl)-1H-imidazole

A mixture of 1-(3-bromophenyl)-2-((2,6-diisopropylphenyl)amino)ethan-1-one (2.3 g, 6.14 mmol), formaldehyde, 37% in water (0.503 ml, 6.76 mmol), and ammonium acetate (4.74 g, 61.4 mmol) was heated in acetic acid (20 ml) and refluxed for 18 hrs. The mixture was cooled down and partitioned between ethyl acetate (EA) and brine and extracted with EA. The organic extract was basified with $Na_2CO_3$(sat) until basic, coated on celite and chromatographed on silica (EA/Hep=1/3) (460 mg, 20%).

Synthesis of 10-(3-(1-(2,6-diisopropylphenyl)-1H-imidazol-4-yl)phenoxy)-3,3,4,4-tetramethyl-3,4-dihydrodibenzo[b,ij]imidazo[2,1,5-de]quinolizine A mixture of 3,3,4,4-tetramethyl-3,4-dihydrodibenzo[b,ij]imidazo[2,1,5-de]quinolizin-10-ol (387 mg, 1.224 mmol), 4-(3-bromophenyl)-1-(2,6-diisopropylphenyl)-1H-imidazole (460 mg, 1.200 mmol), copper(I) iodide (45.7 mg, 0.240 mmol), picolinic acid (59.1 mg, 0.480 mmol), and potassium phosphate (509 mg, 2.400 mmol) was vacuumed and back-filled with nitrogen several times. DMSO (10 ml) was added to the reaction mixture and heated at 140° C. overnight. Cooled down and added DI water. The resulting solid (big chunks) was collected by filtration and dissolved in DCM and dried with $MgSO_4$, then chromatographed on silica (EA/DCM=1/4 to 1/2) (330 mg, 44%).

Synthesis of Compound 3

A mixture of 10-(3-(1-(2,6-diisopropylphenyl)-1H-imidazol-4-yl)phenoxy)-3,3,4,4-tetramethyl-3,4-dihydrodibenzo[b,ij]imidazo[2,1,5-de]quinolizine (0.32 g, 0.517 mmol), $K_2PtCl_4$ (0.215 g, 0.517 mmol), and tetrabutylammonium chloride (0.014 g, 0.052 mmol) was vacuumed and back-filled with nitrogen several times. Acetic acid (20 ml) was added to the reaction mixture and refluxed for 72 hrs. The reaction mixture was cooled down and DI water (50 mL) was added. The resulting solid was collected by filtrated and dissolved in DCM and dried with $MgSO_4$, and chromatographed on silica (DCM/Hep=3/2). The product was triturated in hexane and dried in vacuum oven (160 mg, 38%).

Synthesis of Compound 33

Synthesis of 3'-bromo-5'-chloro-2,4,6-triisopropyl-1,1'-biphenyl

A 100 mL two-necked flask was dried in the oven and charged with 1-bromo-3-chloro-5-iodobenzene (2.02 g, 6.37 mmol) and $NiCl_2(PPh_3)_2$ (0.208 g, 0.318 mmol). The reaction mixture was vacuum and back-filled with nitrogen. Diethyl ether (20 ml) and (2,4,6-triisopropylphenyl)magnesium bromide in THF (12.73 ml, 6.37 mmol) was added and heated at 55° C. for 18 hrs. The reaction mixture was then cooled down and coated on celite and chromatographed on silica (Heptane) (1.74 g, 69%).

Synthesis of 10-((5-chloro-2',4',6'-triisopropyl-[1,1'-biphenyl]-3-yl)oxy)-3,3,4,4-tetramethyl-3,4-dihydrodibenzo[b,ij]imidazo[2,1,5-de]quinolizine A mixture of 3,3,4,4-tetramethyl-3,4-dihydrodibenzo[b,ij]imidazo[2,1,5-de]quinolizin-10-ol (1.245 g, 3.94 mmol), 3'-bromo-5'-chloro-2,4,6-triisopropyl-1,1'-biphenyl (1.55 g, 3.94 mmol), copper(I) iodide (0.150 g, 0.787 mmol), picolinic acid (0.194 g, 1.574 mmol), and potassium phosphate (1.671 g, 7.87 mmol) was vacuumed and back-filled with nitrogen several times. DMSO (16 ml) was added to the reaction mixture and heated at 140° C. for 18 h. The reaction mixture was cooled down and DI water (30 mL) was added.

The resulting solid was collected by filtration and dissolved in DCM and dried with MgSO$_4$, then chromatographed on silica (DCM/EA=40/1) (1.25 g, 51%).

Synthesis of N1-phenyl-N2-(2',4',6'-triisopropyl-5-((3,3,4,4-tetramethyl-3,4-dihydrodibenzo[b,ij]imidazo[2,1,5-de]quinolizin-10-yl)oxy)-[1,1'-biphenyl]-3-yl)benzene-1,2-diamine A mixture of N1-phenylbenzene-1,2-diamine (0.393 g, 2.133 mmol), N1-phenylbenzene-1,2-diamine (0.393 g, 2.133 mmol), (allyl)PdCl-dimer (0.021 g, 0.058 mmol), cBRIDP (0.082 g, 0.233 mmol), and sodium 2-methylpropan-2-olate (0.466 g, 4.85 mmol) was vacuumed and back-filled with nitrogen several times. Toluene (15 ml) was added to the reaction mixture and refluxed for 3 hrs. The reaction mixture was cooled down and coated on celite and chromatographed on silica (DCM/EA=20/1) (890 mg, 59%).

Synthesis of 3-phenyl-1-(2',4',6'-triisopropyl-5-((3,3,4,4-tetramethyl-3,4-dihydrodibenzo[b,ij]imidazo[2,1,5-de]quinolizin-10-yl)oxy)-[1,1'-biphenyl]-3-yl)-1H-benzo[d]imidazol-3-ium Chloride N1-phenyl-N2-(2',4',6'-triisopropyl-5-((3,3,4,4-tetramethyl-3,4-dihydrodibenzo[b,ij]imidazo[2,1,5-de]quinolizin-10-yl)oxy)-[1,1'-biphenyl]-3-yl)benzene-1,2-diamine (0.89 g, 1.145 mmol) was dissolved in triethoxymethane (9.53 ml, 57.3 mmol) and hydrogen chloride (0.113 ml, 1.374 mmol) was added. The reaction mixture was heated at 80° C. for 18 hrs. then cooled down. The resulting white solid was triturated in diethyl ether and collected by filtrated and washed with diethyl ether and dried in the vacuum oven (690 mg, 73%).

Synthesis of Compound 33

A mixture of 3-phenyl-1-(2',4',6'-triisopropyl-5-((3,3,4,4-tetramethyl-3,4-dihydrodibenzo[b,ij]imidazo[2,1,5-de]quinolizin-10-yl)oxy)-[1,1'-biphenyl]-3-yl)-1H-benzo[d]imidazol-3-ium chloride (0.67 g, 0.814 mmol) and silver oxide (0.094 g, 0.407 mmol) was stirred in 1,2-dichloroethane (12 ml) at R.T. overnight. After removing 1,2-dichloroethane, Pt(COD)Cl$_2$ (0.304 g, 0.814 mmol) was added and the reaction mixture was vacuumed and back-filled with nitrogen. 1,2-dichlorobenzene (12 ml) was added and heated at 190° C. for 12 days. Removed solvent and coated on celite and chromatrographed on silica (DCM/Hep=1/1). The product was triturated in MeOH and dried in vacuum oven (193 mg, 24%).

Synthesis of Compound 177

Synthesis of 10-(3-(4-(2,6-diisopropylphenyl)-1H-pyrazol-1-yl)phenoxy)-3,3,4,4-tetramethyl-2-phenyl-3,4-dihydrodibenzo[b,ij]imidazo[2,1,5-de]quinolizine A mixture of 3,3,4,4-tetramethyl-2-phenyl-3,4-dihydrodibenzo[b,ij]imidazo[2,1,5-de]quinolizin-10-ol (0.591 g, 1.507 mmol), 1-(3-bromophenyl)-4-(2,6-diisopropylphenyl)-1H-pyrazole (0.55 g, 1.435 mmol), copper(I) iodide (0.055 g, 0.287 mmol), picolinic acid (0.071 g, 0.574 mmol), and potassium phosphate (0.609 g, 2.87 mmol) was vacuumed and back-filled with nitrogen several times. DMSO (10 ml) was added to the reaction mixture and heated at 140° C. for 18 h, then cooled down and DI water (20 mL) was added. The resulting solid was collected by filtration and dissolved in DCM and dried with MgSO$_4$ and chromatographed on silica (DCM/EA=40/1) (80% yield).

Synthesis of Compound 177

A mixture of 10-(3-(4-(2,6-diisopropylphenyl)-1H-pyrazol-1-yl)phenoxy)-3,3,4,4-tetramethyl-2-phenyl-3,4-dihydrodibenzo[b,ij]imidazo[2,1,5-de]quinolizine (0.78 g, 1.122 mmol), K$_2$PtCl$_4$ (0.466 g, 1.122 mmol), and tetrabutylammonium chloride (0.031 g, 0.112 mmol) in a Schlenk tube was vacuumed and back-filled with nitrogen several times. Acetic acid (30 ml) was added to the reaction mixture and refluxed for 72 h. The reaction mixture was cooled down and DI water (60 mL) was added. The resulting solid was collected by filtrated and dissolved in DCM and dried with MgSO$_4$ and chromatographed on silica (DCM/Hep=3/2). The product was triturated in hexane and dried in vacuum oven (21% yield).

Synthesis of Compound 178

Synthesis of 3,3,4,4-tetramethyl-2-phenyl-10-((4,4,5,5-tetramethyl-3-phenyl-4,5-dihydropyrazolo[1,5-a]quinolin-8-yl)oxy)-3,4-dihydrodibenzo[b,ij]imidazo[2,1,5-de]quinolizine A mixture of 3,3,4,4-tetramethyl-2-phenyl-3,4-dihydrodibenzo[b,ij]imidazo[2,1,5-de]quinolizin-10-ol (0.648 g, 1.652 mmol), 8-bromo-4,4,5,5-tetramethyl-3-phenyl-4,5-dihydropyrazolo[1,5-a]quinoline (0.6 g, 1.573 mmol), copper (I) iodide (0.060 g, 0.315 mmol), picolinic acid (0.077 g, 0.629 mmol), and potassium phosphate (0.668 g, 3.15 mmol) was vacuumed and back-filled with nitrogen several times. DMSO (10 ml) was added to the reaction mixture and heated at 140° C. for 18 hrs. then cooled down and DI water (20 mL) was added. The resulting solid (big chunks) was collected by filtration and dissolved in DCM and dried with MgSO$_4$. Chromatographed on silica (DCM/EA=20/1) (845 mg, 78%).

Synthesis of Compound 178

A mixture of 3,3,4,4-tetramethyl-2-phenyl-10-((4,4,5,5-tetramethyl-3-phenyl-4,5-dihydropyrazolo[1,5-a]quinolin-8-yl)oxy)-3,4-dihydrodibenzo[b,ij]imidazo[2,1,5-de]quinolizine (0.845 g, 1.219 mmol), K$_2$PtCl$_4$ (0.506 g, 1.219 mmol), and tetrabutylammonium chloride (0.034 g, 0.122 mmol) in a Schlenk tube was vacuumed and back-filled with nitrogen several times. Acetic acid (35 ml) was added to the reaction mixture and refluxed for 72 h. The reaction mixture was then cooled down and DI water (60 mL) was added. The resulting solid was collected by filtrated and dissolved in DCM and dried with MgSO$_4$ then chromatographed on silica (DCM/Hep=1/1). The product was triturated in hexane and dried in vacuum oven (678 mg, 63%).

Synthesis of Compound 179

Synthesis 1-(3-bromophenyl)-2-((2,6-diisopropylphenyl)amino)ethan-1-one

A mixture of 2-bromo-1-(3-bromophenyl)ethan-1-one (3 g, 10.79 mmol) and 2,6-diisopropylaniline (4.02 g, 22.67 mmol) was stirred in Ethanol (15 ml) at Room Temperature for 2 days. Then, EtOH was removed and the remaining product was triturated in diethyl ether. The resulting white solid (salt) was removed by filtration. The filtrate was concentrated and chromatographed on silica (THF/Hep=1/20) and obtained yellow oil (3 g, 74%).

Synthesis of 4-(3-bromophenyl)-1-(2,6-diisopropylphenyl)-1H-imidazole

A mixture of 1-(3-bromophenyl)-2-((2,6-diisopropylphenyl)amino)ethan-1-one (2.3 g, 6.14 mmol), formaldehyde, 37% in water (0.503 ml, 6.76 mmol), and ammonium acetate (4.74 g, 61.4 mmol) was heated in Acetic Acid (20 ml) at reflux for 18 h. The mixture was cooled down and partitioned between ethyl acetate (EA) and brine and extracted with EA. The organic extract was basified with $Na_2CO_3$(sat) until basic. Coated on celite and chromatographed on silica (EA/Hep=1/3) (460 mg, 20%).

Synthesis of 10-(3-(1-(2,6-diisopropylphenyl)-1H-imidazol-4-yl)phenoxy)-3,3,4,4-tetramethyl-2-phenyl-3,4-dihydrodibenzo[b,ij]imidazo[2,1,5-de]quinolizine A mixture of 3,3,4,4-tetramethyl-2-phenyl-3,4-dihydrodibenzo[b,ij]imidazo[2,1,5-de]quinolizin-10-ol (585 mg, 1.490 mmol), 4-(3-bromophenyl)-1-(2,6-diisopropylphenyl)-1H-imidazole (560 mg, 1.461 mmol), copper(I) iodide (55.6 mg, 0.292 mmol), picolinic acid (71.9 mg, 0.584 mmol), and potassium phosphate (620 mg, 2.92 mmol) was vacuumed and back-filled with nitrogen several times. Dimethyl sulfoxide (DMSO) (10 ml) was added to the reaction mixture and heated at 140° C. for 18 hours. The reaction mixture was cooled down and DI water (20 mL) was added. The resulting solid was collected by filtration and dissolved in dichloromethane (DCM) and dried with $MgSO_4$ and chromatographed on silica (EA/DCM=1/9) (0.55 g, 54%).

Synthesis of Compound 179

A mixture of 10-(3-(1-(2,6-diisopropylphenyl)-1H-imidazol-4-yl)phenoxy)-3,3,4,4-tetramethyl-2-phenyl-3,4-dihydrodibenzo[b,ij]imidazo[2,1,5-de]quinolizine (0.55 g, 0.791 mmol), $K_2PtCl_4$ (0.329 g, 0.791 mmol), and tetrabutylammonium chloride (0.022 g, 0.079 mmol) was vacuumed and back-filled with nitrogen several times. Acetic Acid (25 ml) was added to the reaction mixture and refluxed for one week. The reaction mixture was cooled down and DI water (50 mL) was added. The resulting solid was collected by filtrated and dissolved in DCM and dried with $MgSO_4$ and chromatographed on silica (DCM/Hep=3/2). The product was triturated in MeOH and dried in vacuum oven (494 mg, 70%).

TABLE 1

| Structure | PLQY in PMMA (%) | Excited state lifetime at 77 K (μs) |
|---|---|---|
| Compound 3 | 92 | 5.04 |

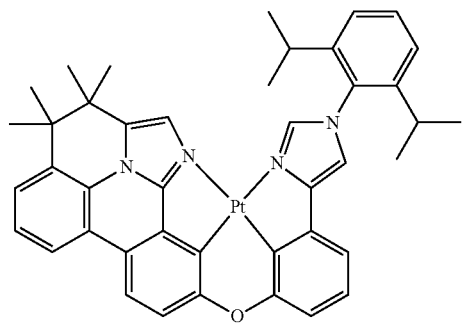

| | | |
|---|---|---|
| Compound 22 | 75 | 3.44 |

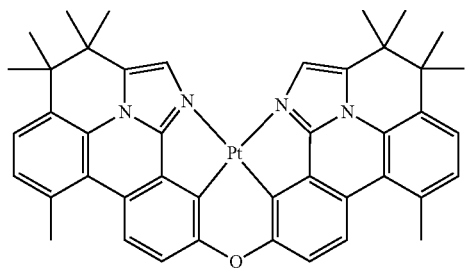

TABLE 1-continued
| Structure | PLQY in PMMA (%) | Excited state lifetime at 77 K (μs) |
|---|---|---|
| Compound 33 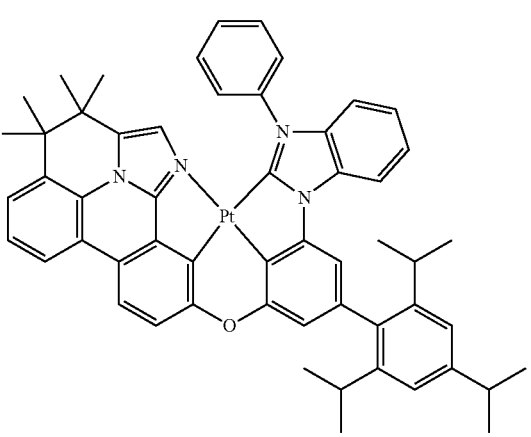 | 100 | 2.82 |
| Compound 177 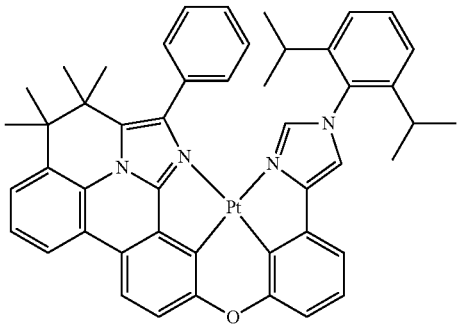 | 92 | 5.50 |
| Compound 178 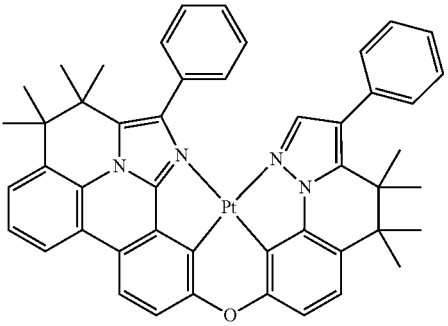 | 100 | 5.40 |
| Compound 179 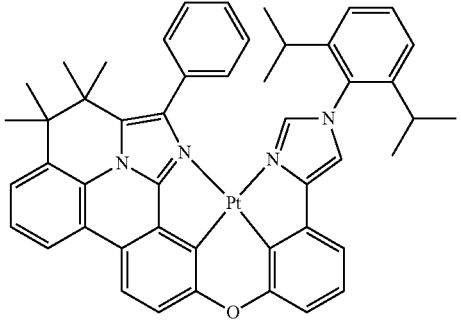 | 89 | 5.35 |

TABLE 1-continued

| | Structure | PLQY in PMMA (%) | Excited state lifetime at 77 K (μs) |
|---|---|---|---|
| Comparative Example 1 | 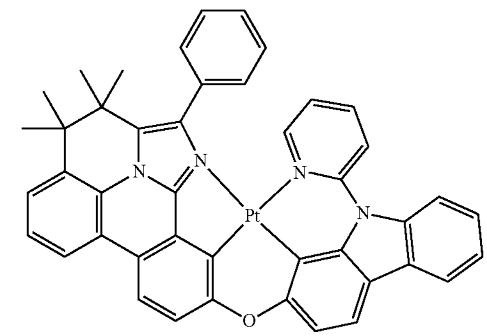 | 70 | 7.30 |
| Comparative Example 2 | 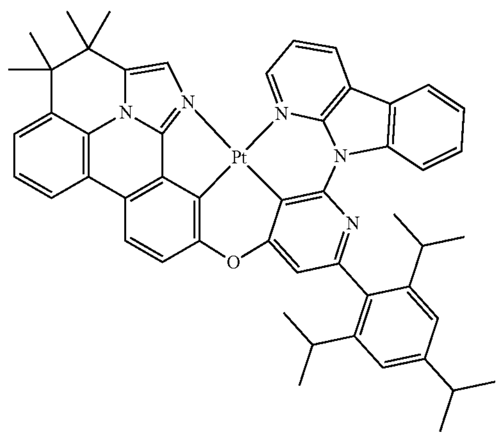 | 67 | 10.7 |

Table 1 shows PLQY, and excited state lifetime for the inventive Compound 3, 22, 33, 177, 178, and 179 versus Comparative Example 1-2. The inventive compounds showed higher PLQYs, and shorter excited state lifetimes as compared to those of Comparative Examples. High PLQYs indicate that inventive compounds are very efficient emitters, which often times lead to efficient device performance. Both high PLQY and short excited state lifetime of inventive compound are achieved via the introduction of 5,6,5-metallocycle molecular construction. In comparison, both Comparative Examples are 5,6,6-metallocycle. 5,6,5-metallocycle gives much planar geometry which is closer to the ideal square planar, leading to a more efficient electronic transition between $S_0$ to $T_1$ states without too much geometric reorganization. The readily transition between $S_0$ to $T_1$ states generally increases radiative rate and suppresses nonradiative rate, resulting in overall high PLQY and short excited state lifetime.

OLED Device Fabrication:

OLEDs were grown on a glass substrate pre-coated with an indium-tin-oxide (ITO) layer having a sheet resistance of 15-Ω/sq. Prior to any organic layer deposition or coating, the substrate was degreased with solvents and then treated with an oxygen plasma for 1.5 minutes with 50 W at 100 mTorr and with UV ozone for 5 minutes. The devices were fabricated in high vacuum ($<10^{-6}$ Torr) by thermal evaporation. The anode electrode was 750 Å of indium tin oxide (ITO). The device example had organic layers consisting of, sequentially, from the ITO surface, 100 Å thick Compound A (HIL), 250 Å layer of Compound B (HTL), 50 Å of Compound C (EBL), 300 Å of Compound D doped with 15 or 20% of Emitter listed in Table 1 (EML), 50 Å of Compound E (BL), 300 Å of Compound G doped with 35% of Compound F (ETL), 10 Å of Compound G (EIL) followed by 1,000 Å of Al (Cath). All devices were encapsulated with a glass lid sealed with an epoxy resin in a nitrogen glove box (<1 ppm of $H_2O$ and $O_2$,) immediately after fabrication with a moisture getter incorporated inside the package. Doping percentages are in volume percent.

The structure of the compounds used in the experimental devices are:

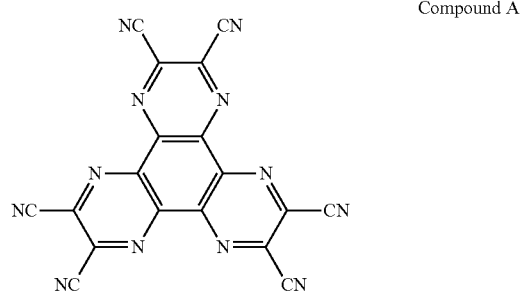

Compound A

Compound B
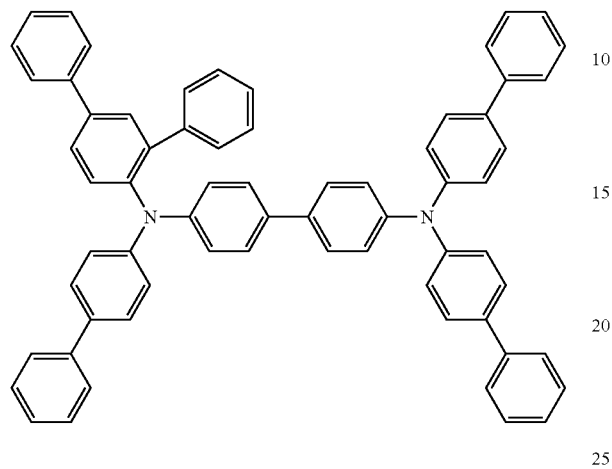
Compound C
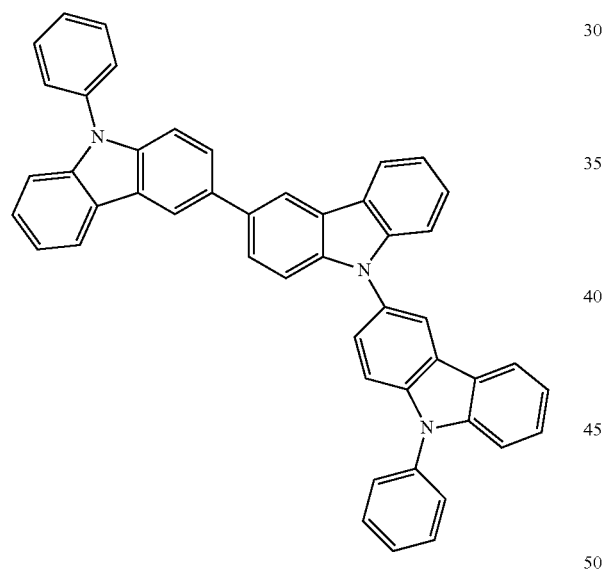
Compound D
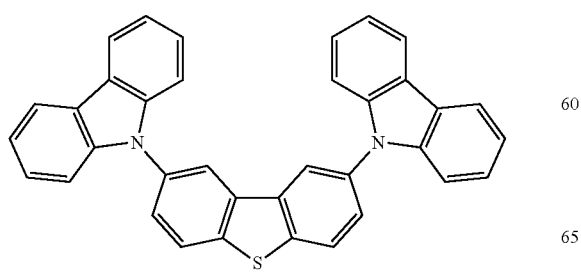
Compound E
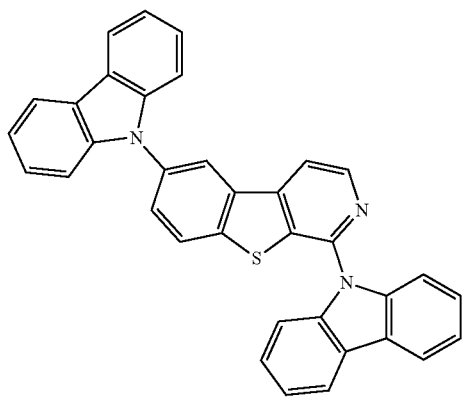
Compound F
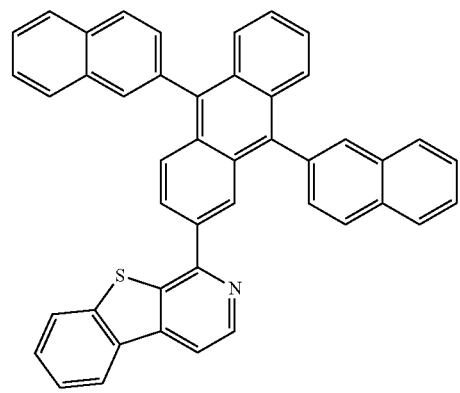
Compound G
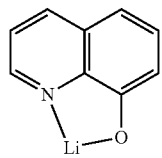

TABLE 2

| | Device Data | | | | | | | |
|---|---|---|---|---|---|---|---|---|
| | 1931 CIE | | λ max | FWHM | at 1,000 nit | | | |
| | | | | | Voltage | LE | EQE | PE |
| Device | x | y | [nm] | [nm] | [a.u.][a] | [a.u.] | [a.u.] | [a.u.] |
| Compound 3 | 0.144 | 0.241 | 465 | 21 | 69 | 89 | 149 | 707 |
| Compound 22 | 0.153 | 0.434 | 484 | 19 | 72 | 199 | 249 | 1480 |
| Compound 33 | 0.158 | 0.504 | 489 | 21 | 85 | 156 | 179 | 1000 |
| Compound 177 | 0.138 | 0.246 | 468 | 17 | 77 | 342 | 140 | 553 |
| Compound 178 | 0.142 | 0.263 | 468 | 19 | 75 | 92 | 149 | 667 |
| Compound 179 | 0.144 | 0.272 | 468 | 22 | 65 | 110 | 179 | 927 |
| Comparative Example 1 | 0.163 | 0.255 | 460 | 54 | 70 | 85 | 130 | 667 |
| Comparative Example 2 | 0.401 | 0.475 | 566 | 116 | 100 | 100 | 100 | 100 |

[a]a.u. = arbitrary units; all data is normalized relative to Comparative Example 2.

Table 2 shows device data for the inventive Compound 3, 22, 33, 177, 178, and 179 versus Comparative Example 1-2. The higher EQEs of inventive compounds are in agreement of their high PLQYs as compared to those of comparative examples. In addition, all inventive compounds exhibit very narrow electroluminescent spectra with a full-width-half-maximum (FWHM) less than 25 nm, whereas Comparative Example 1 and 2 have a FWHM of 54 and 116 nm, respectively. This again demonstrates the benefit of adopting the planar 5,6,5-metallocycle geometry to minimize structural distortion. Less structural distortion in both ground and excited states usually result in narrower emission spectrum. The narrow emission is important to achieve saturate color. It is desirable to have the CIEy coordinate as small as possible to reach saturate blue. For example, Compound 3 has a smaller CIEy (0.241) than that of Comparative Example 1 (0.255). Despite Compound 3's longer peak wavelength, it has a more saturate blue emission color.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

I claim:

1. A compound having the formula:

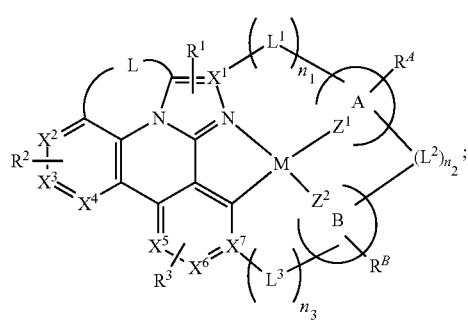

Formula I wherein rings A and B are each independently a 5- or 6-membered carbocyclic or heterocyclic ring;
wherein at least one of rings A and B is a 5-membered carbocyclic or heterocyclic ring;
wherein $Z^1$, $Z^2$, $X^1$ to $X^7$ are each independently selected from the group consisting of carbon and nitrogen;
wherein each of $R^1$, $R^2$, $R^3$, $R^A$ and $R^B$ independently represents none to a maximum possible number of substitutions;
wherein each of $R^1$, $R^2$, $R^3$, $R^A$ and $R^B$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein any two substitutions in $R^1$, $R^2$, $R^3$, $R^A$ and $R^B$ are optionally joined or fused into a ring;
wherein $n_1$, $n_2$, and $n_3$ each independently is 0 or 1;
wherein when $n_1$, $n_2$ or $n_3$ is 1, each of the respective $L^1$, $L^2$, or $L^3$ is independently selected from the group consisting of a direct bond, BR, NR, PR, O, S, Se, C=O, S=O, SO₂, CRR', SiRR', GeRR', alkyl, cycloalkyl, and combinations thereof, wherein R and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein when $n_1$, $n_2$ or $n_3$ is 0, the respective $L^1$, $L^2$, or $L^3$ is not present;
wherein $n_1+n_2+n_3$ is at least 2;
wherein when $L^1$ is present, $X^1$ is carbon; when $L^3$ is present, $X^7$ is carbon;
wherein L is a linking group selected from the group consisting of —CR'R"—CR'R"—, —CR'R'—CR"R"—, —CH₂—CH₂—, —CR'R'—CR'R'—CR'R'—, —CR'R'—NR'—, —CR'=CR'—CR'R'—, —O—SiR'R'—, —CR'R'—S—, —CR'R'—O—, and —CR'R'—SiR'R'—,
wherein each R' is independently selected from the group consisting of H, deuterium, alkyl, cycloalkyl, aryl, heteroaryl, partially or fully deuterated variations thereof, and combinations thereof, wherein each R" is independently selected from the group consisting of alkyl, cycloalkyl, aryl, heteroaryl, partially or fully deuterated variations thereof, and combinations thereof, wherein R's and R"s are optionally joined or fused to form a 5-membered or 6-membered ring; and wherein M is Pt or Pd.

2. The compound of claim 1, wherein each of $R^1$, $R^2$, $R^3$, $R^A$, $R^B$, R and R' is independently selected from the group consisting of hydrogen, deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof.

3. The compound of claim 1, wherein the linking atoms in L form at least one single aliphatic bond between two linking atoms.

4. The compound of claim 1, wherein ring A is a 5-membered aromatic ring and ring B is a 6-membered aromatic ring; or ring A is a 6-membered aromatic ring and ring B is a 5-membered aromatic ring; or rings A and B are 5-membered aromatic rings.

5. The compound of claim 1, wherein at least one of rings A and B is selected from the group consisting of imidazole, pyrazole, thiazole, oxazole, and derived carbene thereof.

6. The compound of claim 1, wherein $X^1$ to $X^7$ are carbon.

7. The compound of claim 1, wherein at least one of $X^1$ to $X^7$ is nitrogen.

8. The compound of claim 1, wherein $L^2$ is present and is a direct bond.

9. The compound of claim 1, wherein at least one pair of substituents in $R^A$, $L^2$, and $R^B$ are joined or fused into a ring.

10. The compound of claim 1, wherein the linking group L is selected from the group consisting of:

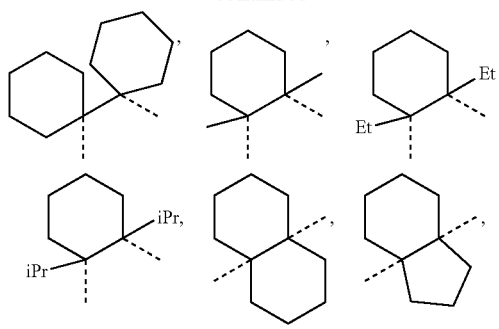

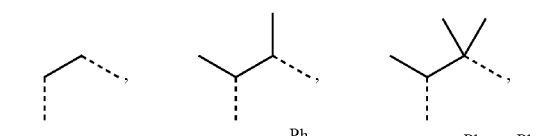

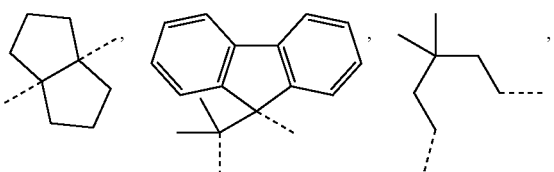

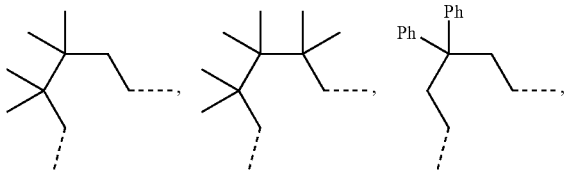

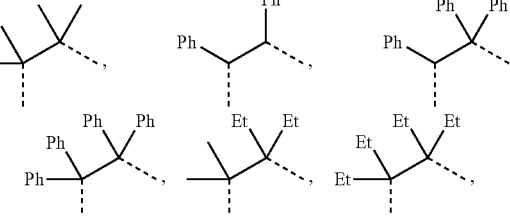

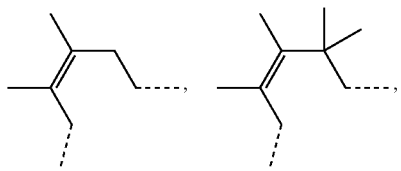

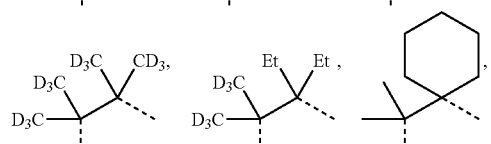

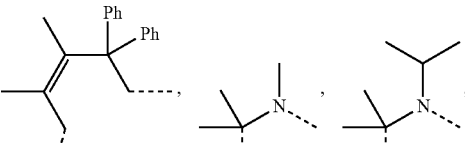

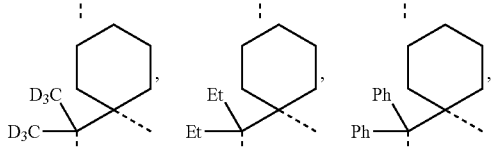

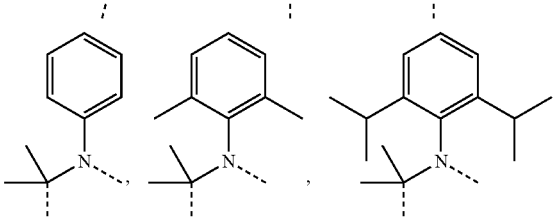

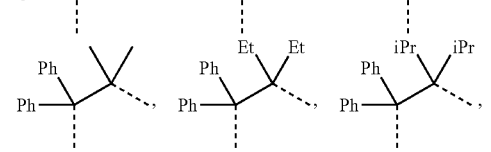

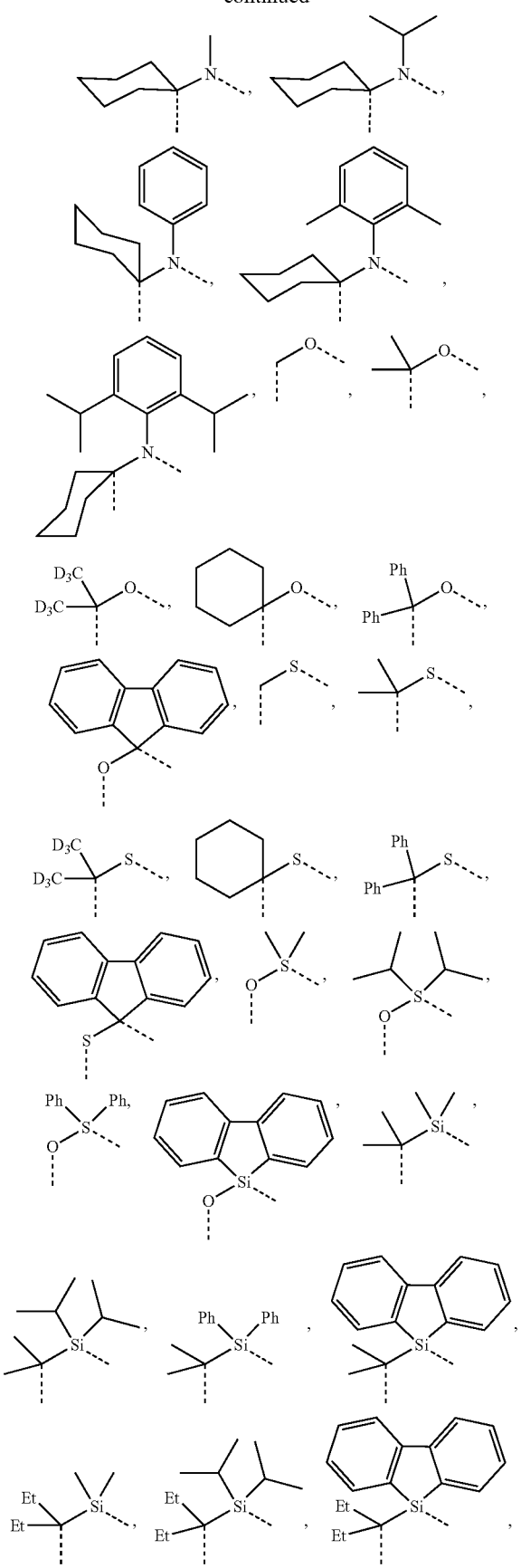
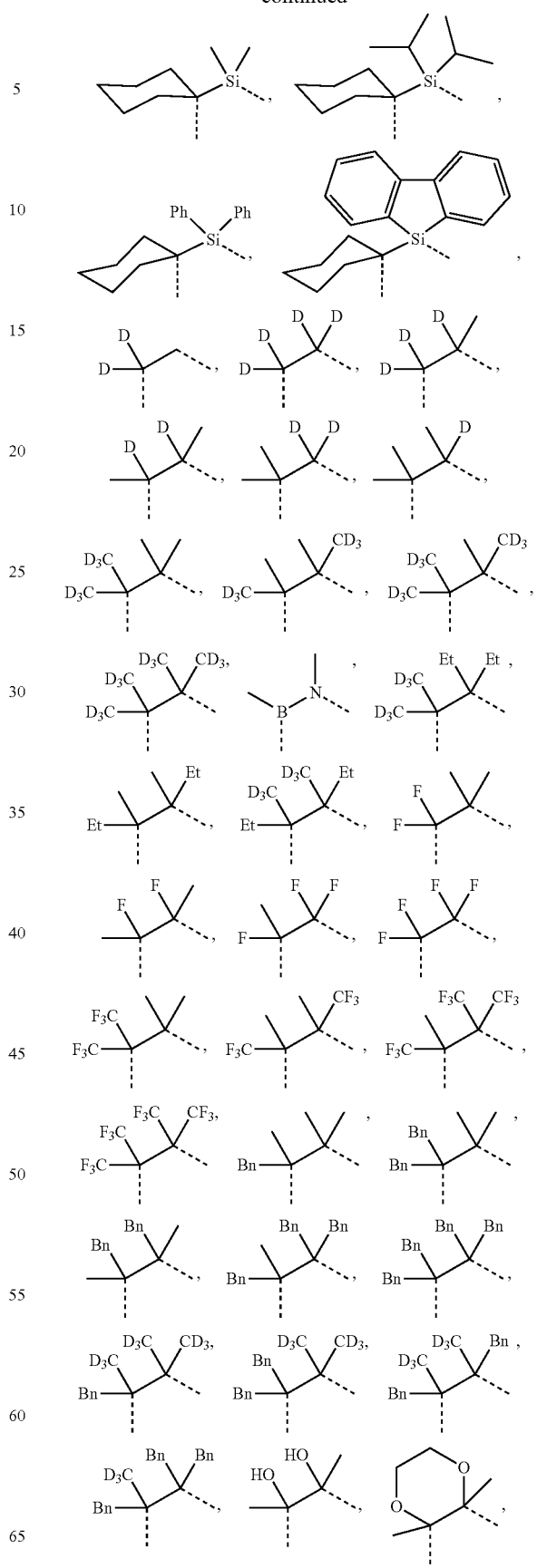

-continued
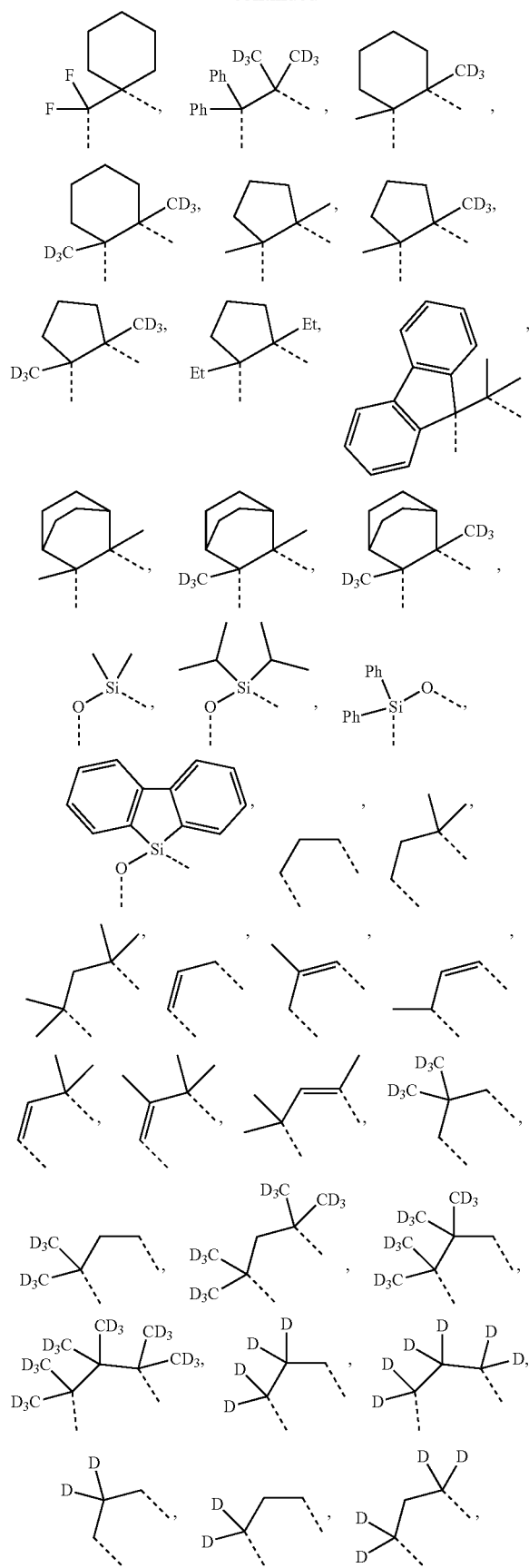
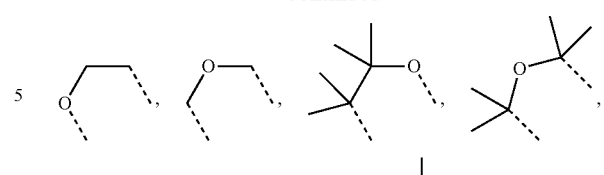
and
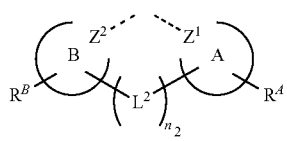
11. The compound of claim 1, wherein the partial structure of
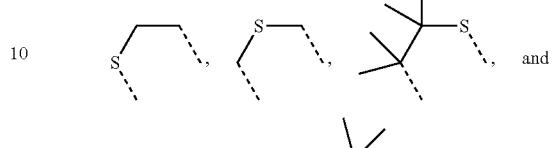
in Formula I is selected from the group consisting of:
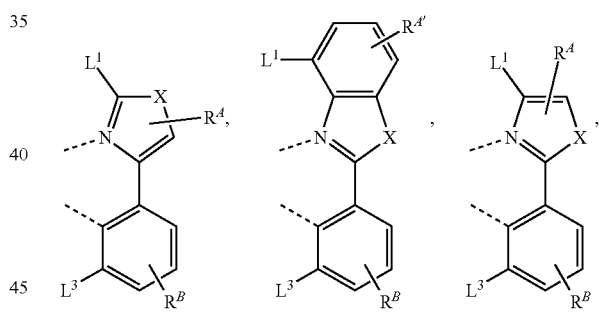
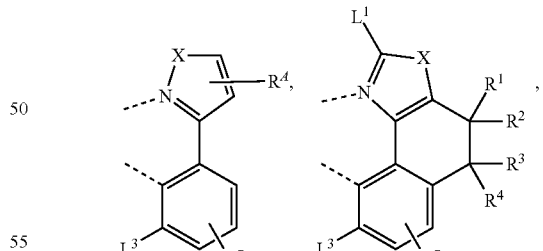
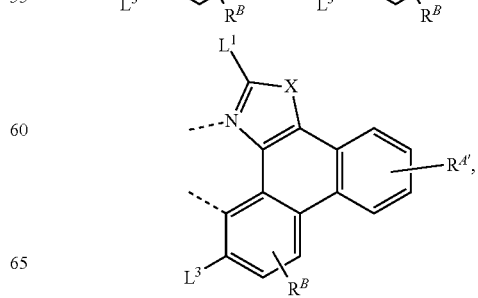

-continued
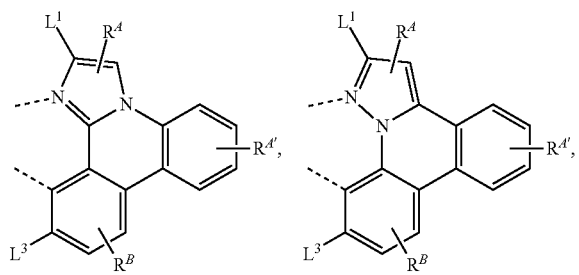
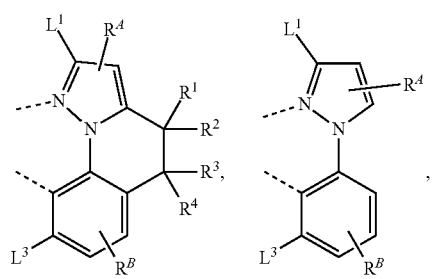
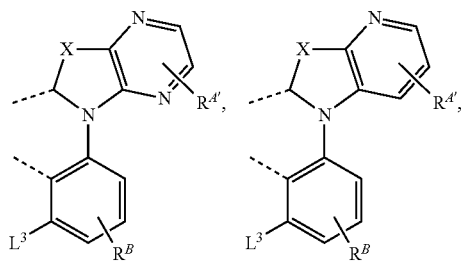
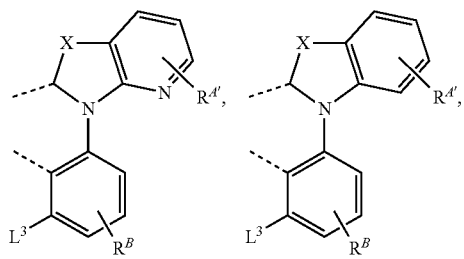
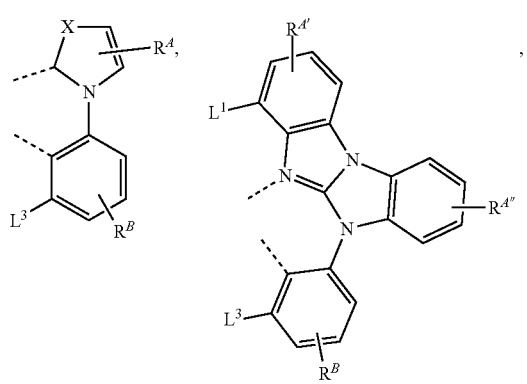
-continued
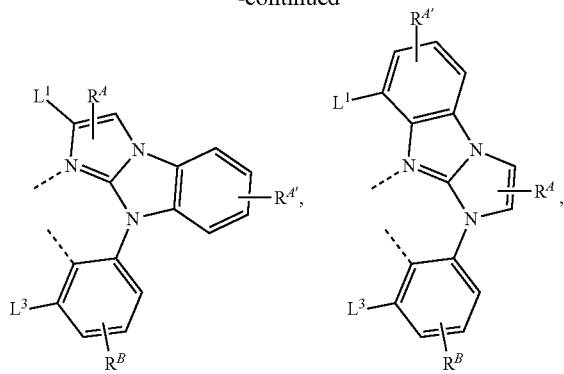
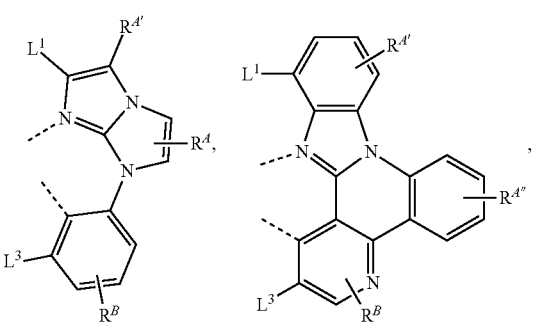
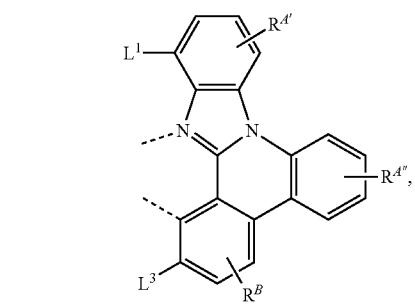
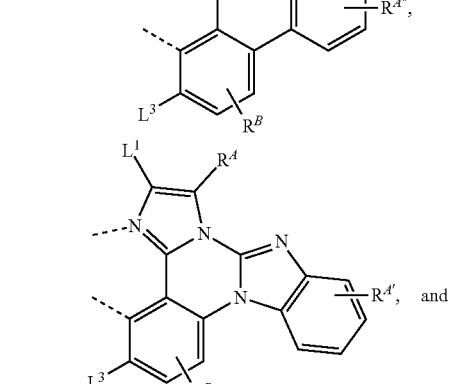 and
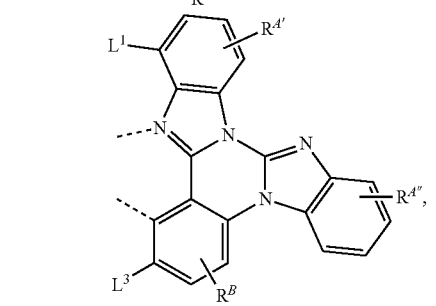

wherein X is one of O, S, NR', BR', CR'R", or SiR'R"; and wherein each of $R^4$, $R^{A'}$, $R^{A''}$, and R" is independently selected from the group consisting of hydrogen, deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof.

12. The compound of claim 1, wherein the compound is selected from group consisting of Compound x, wherein x is an integer defined by 44i+j−44, wherein i is an integer from 1 to 34, and j is an integer from 1 to 44;

wherein each Compound x has a structure according to formula $Pt(L_{Ai})(L_{Bj})$;

wherein $L_{Ai}$ and $L_{Bj}$ are based on the following formulas:

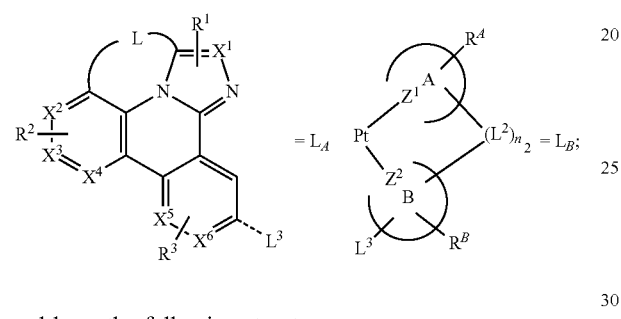

and have the following structures:

$L_{A1}$

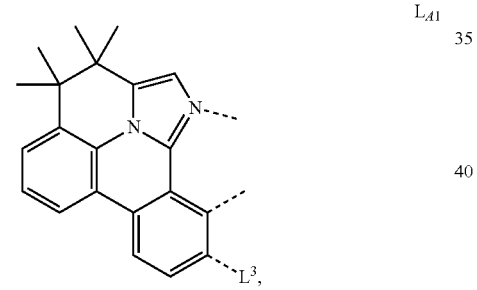

$L_{A2}$

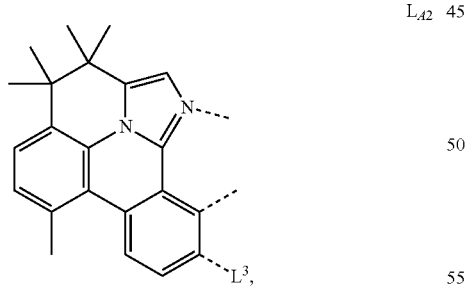

$L_{A3}$

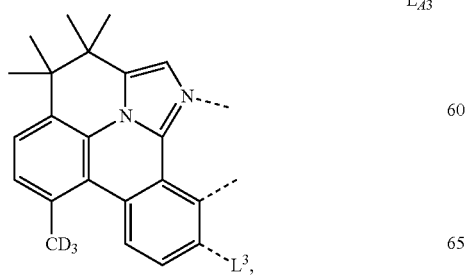

-continued $L_{A4}$

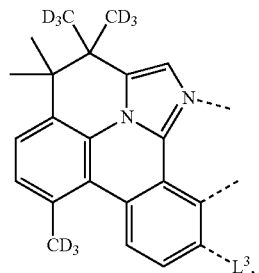

$L_{A5}$

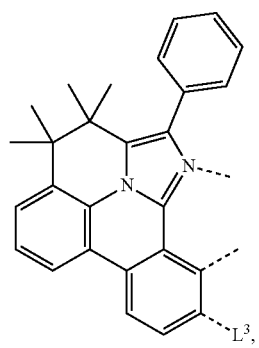

$L_{A6}$

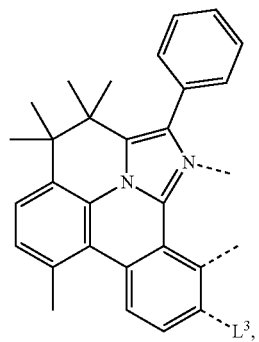

$L_{A7}$

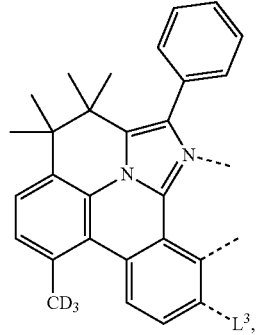

13. A formulation comprising the compound of claim 1.

14. An organic light emitting device (OLED) comprising:
an anode;
a cathode; and
an organic layer, disposed between the anode and the cathode, comprising a compound having the formula:

Formula I

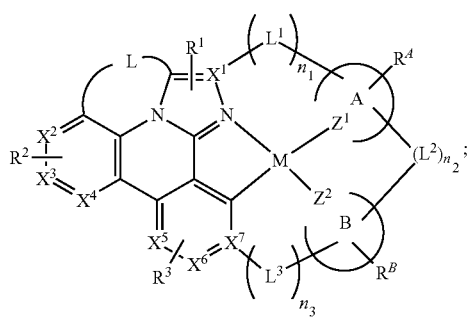

wherein rings A and B are each independently a 5- or 6-membered carbocyclic or heterocyclic ring;
wherein at least one of rings A and B is a 5-membered carbocyclic or heterocyclic ring;
wherein $Z^1$, $Z^2$, $X^1$ to $X^7$ are each independently selected from the group consisting of carbon and nitrogen;
wherein each of $R^1$, $R^2$, $R^3$, $R^A$ and $R^B$ independently represents none to a maximum possible number of substitutions;
wherein $R^1$, $R^2$, $R^3$, $R^A$ and $R^B$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein any two substitutions in $R^1$, $R^2$, $R^3$, $R^A$ and $R^B$ are optionally joined or fused into a ring;
wherein $n_1$, $n_2$, and $n_3$ each independently is 0 or 1;
wherein when $n_1$, $n_2$ or $n_3$ is 1, each of the respective $L^1$, $L^2$, or $L^3$ is independently selected from the group consisting of a direct bond, BR, NR, PR, O, S, Se, C=O, S=O, SO$_2$, CRR', SiRR', GeRR', alkyl, cycloalkyl, and combinations thereof, wherein R and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein when $n_1$, $n_2$ or $n_3$ is 0, the respective $L^1$, $L^2$, or $L^3$ is not present;
wherein $n_1+n_2+n_3$ is at least 2;
wherein when $L^1$ is present, $X^1$ is carbon; when $L^3$ is present, $X^7$ is carbon;
wherein L is a linking group selected from the group consisting of —CR'R"—CR'R"—, —CR'R'—CR"R"—, —CR'R'—CR'R'—CR'R'—, —CR'R'—NR'—, —CR'=CR'—CR'R'—, —O—SiR'R'—, —CR'R'—S—, —CRR'—O—, and —CR'R'—SiR'R'—,
wherein each R' is independently selected from the group consisting of H, deuterium, alkyl, cycloalkyl, aryl, heteroaryl, partially or fully deuterated variations thereof, and combinations thereof,
wherein each R" is independently selected from the group consisting of alkyl, cycloalkyl, aryl, heteroaryl, partially or fully deuterated variations thereof, and combinations thereof,
wherein R's and R"s are optionally joined or fused to form a 5-membered or 6-membered ring; and
wherein M is Pt or Pd.

15. The OLED of claim 14, wherein the organic layer is an emissive layer and the compound is an emissive dopant or a non-emissive dopant.

16. The OLED of claim 14, wherein the organic layer further comprises a host, wherein host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

17. The OLED of claim 14, wherein the organic layer further comprises a host, wherein the host is selected from the group consisting of:

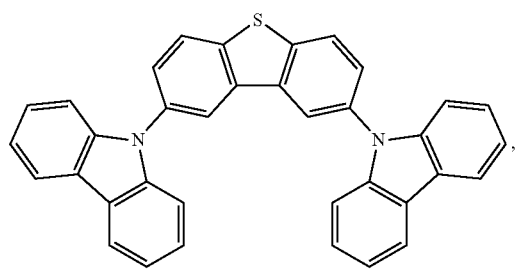

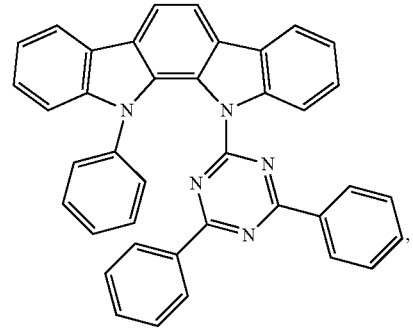

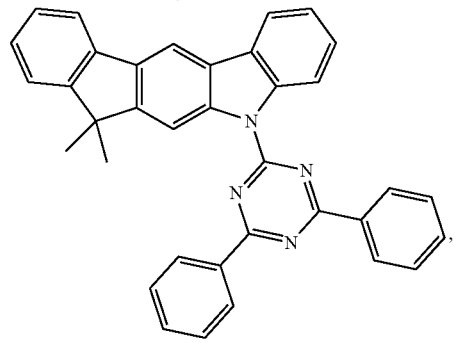

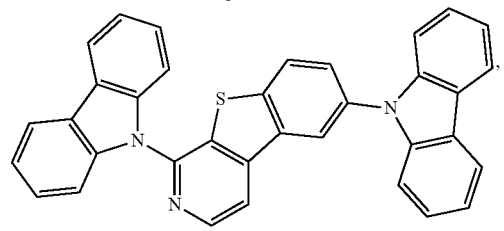

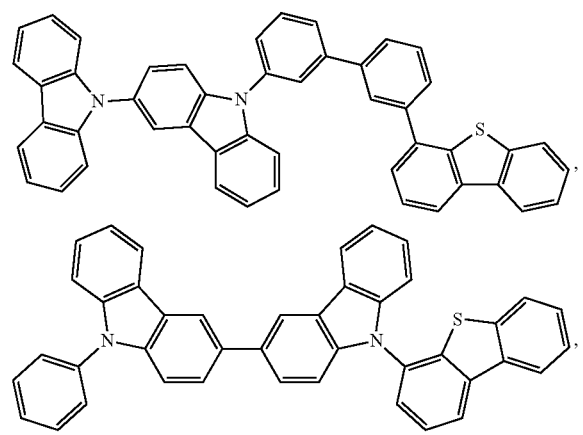
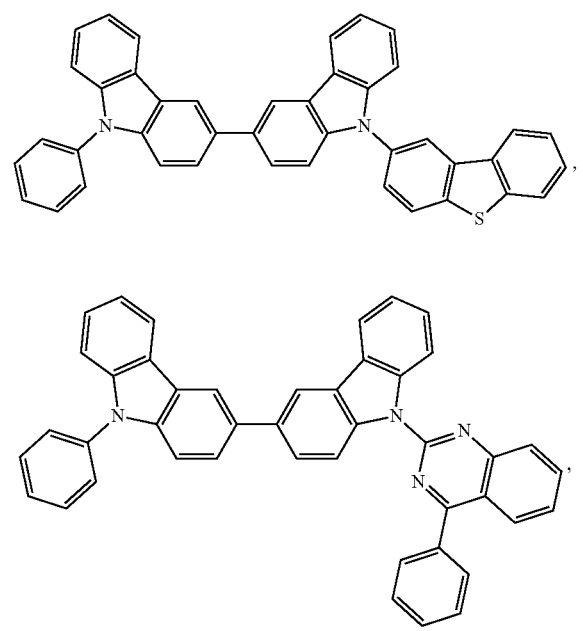
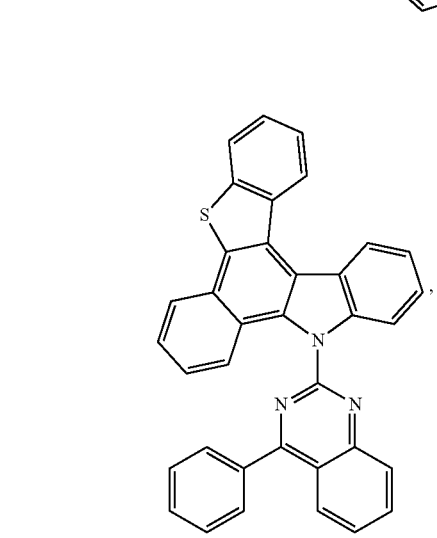
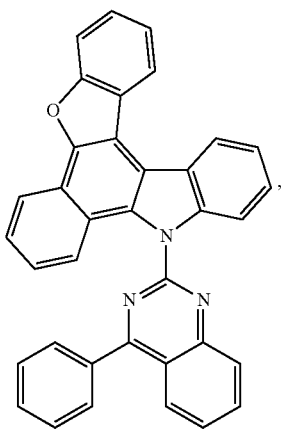
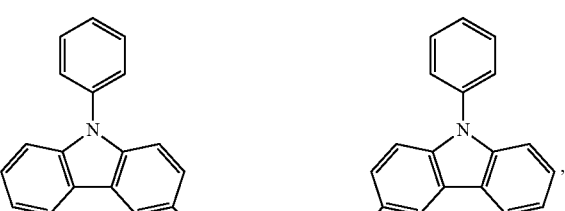
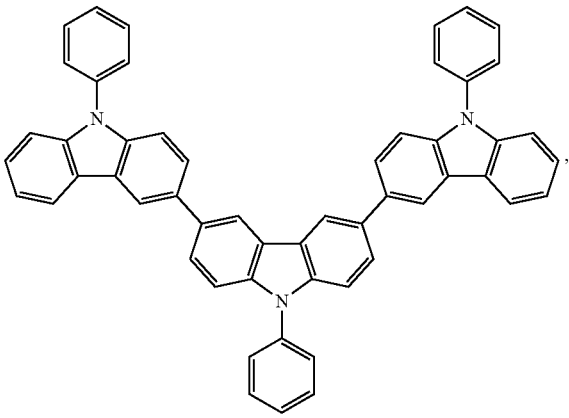
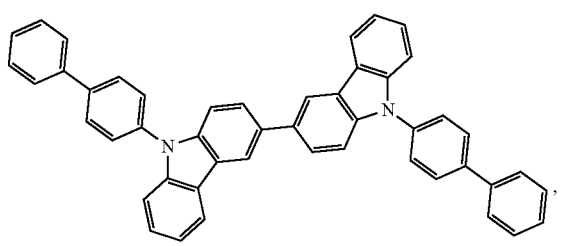
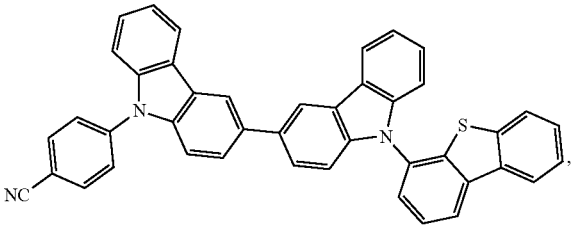

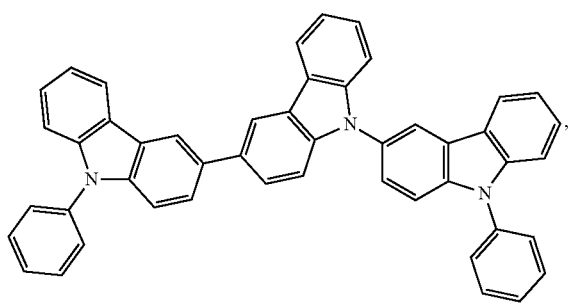
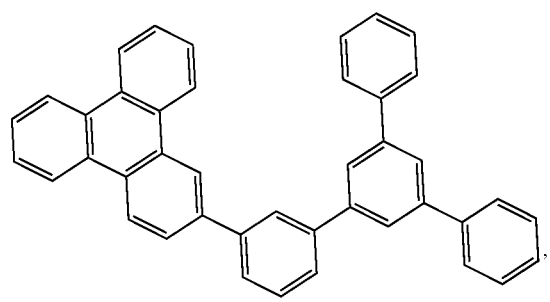
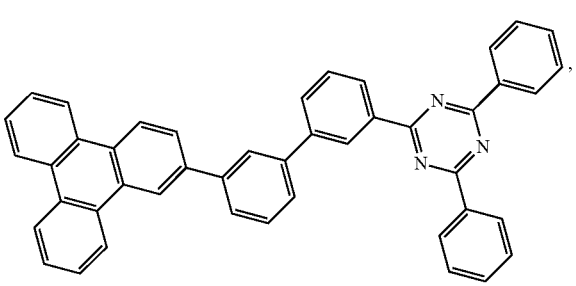
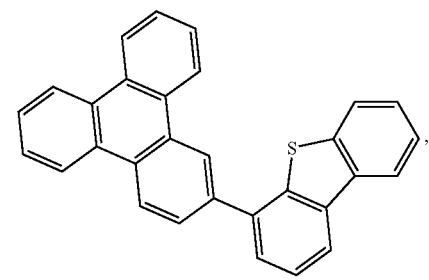
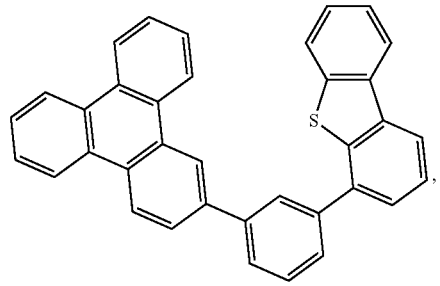
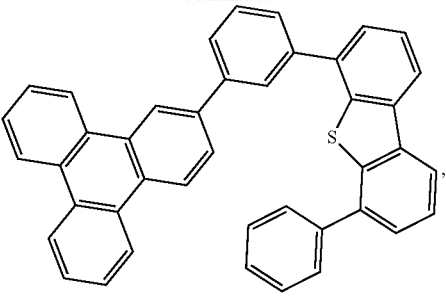
and combinations thereof.
18. A consumer product comprising an organic light-emitting device (OLED) comprising:
   an anode;
   a cathode; and
   an organic layer, disposed between the anode and the cathode, comprising a compound having the formula:
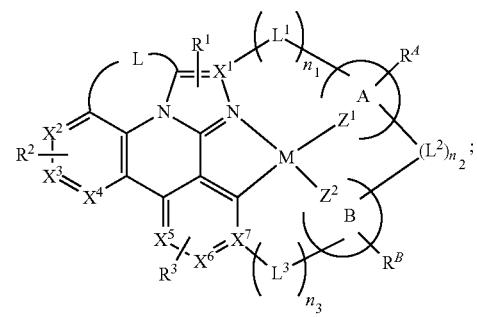
Formula I wherein rings A and B are each independently a 5- or 6-membered carbocyclic or heterocyclic ring;

wherein at least one of rings A and B is a 5-membered carbocyclic or heterocyclic ring;

wherein $Z^1$, $Z^2$, $X^1$ to $X^7$ are each independently selected from the group consisting of carbon and nitrogen;

wherein each of $R^1$, $R^2$, $R^3$, $R^A$ and $R^B$ independently represents none to a maximum possible number of substitutions;

wherein $R^1$, $R^2$, $R^3$, $R^A$ and $R^B$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any two substitutions in $R^1$, $R^2$, $R^3$, $R^A$ and $R^B$ are optionally joined or fused into a ring;

wherein $n_1$, $n_2$, and $n_3$ each independently is 0 or 1;

wherein when $n_1$, $n_2$ or $n_3$ is 1, each of the respective $L^1$, $L^2$, or $L^3$ is independently selected from the group consisting of a direct bond, BR, NR, PR, O, S, Se, C=O, S=O, SO$_2$, CRR', SiRR', GeRR', alkyl, cycloalkyl, and combinations thereof, wherein R and R' are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein when $n_1$, $n_2$ or $n_3$ is 0, the respective $L^1$, $L^2$, or $L^3$ is not present;

wherein $n_1+n_2+n_3$ is at least 2;

wherein when $L^1$ is present, $X^1$ is carbon; when $L^3$ is present, $X^7$ is carbon;

wherein L is a linking group selected from the group consisting of —CR'R"—CR'R"—, —CR'R'—CR"R"—, —CH$_2$—CH$_2$—, —CR'R'—CR'R'—CR'R'—, —CR'=CR'—CR'R'—, —O—SiR'R'—, —CR'R'—S—, —CR'R'—O—, and —CR'R'—SiR'R'—, wherein each R' is independently selected from the group consisting of H, deuterium, alkyl, cycloalkyl, aryl, heteroaryl, partially or fully deuterated variations thereof, and combinations thereof, wherein each R" is independently selected from the group consisting of alkyl, cycloalkyl, aryl, heteroaryl, partially or fully deuterated variations thereof, and combinations thereof, wherein R's and R"s are optionally joined or fused to form a 5-membered or 6-membered ring; and wherein M is Pt or Pd.

19. The consumer product of claim 18, wherein the consumer product is selected from the group consisting of a flat panel display, a computer monitor, a medical monitors television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a microdisplay, a 3-D display, a virtual reality or augmented reality display, a vehicle, a large area wall, a theater or stadium screen, and a sign.

* * * * *

UNITED STATES PATENT AND TRADEMARK OFFICE
CERTIFICATE OF CORRECTION

PATENT NO. : 10,301,338 B2  Page 1 of 7
APPLICATION NO. : 15/948031
DATED : May 28, 2019
INVENTOR(S) : Hsiao-Fan Chen It is certified that error appears in the above-identified patent and that said Letters Patent is hereby corrected as shown below:

In the Claims

In Claim 10, Column 161, Lines 59-67, please delete:

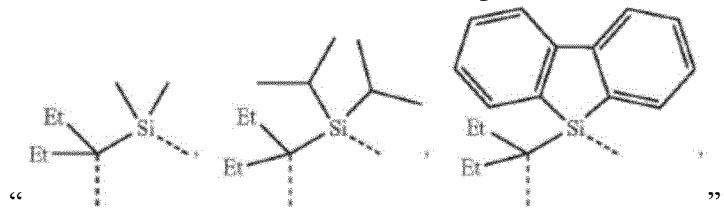

"                     ,                     ,                     "

And insert:

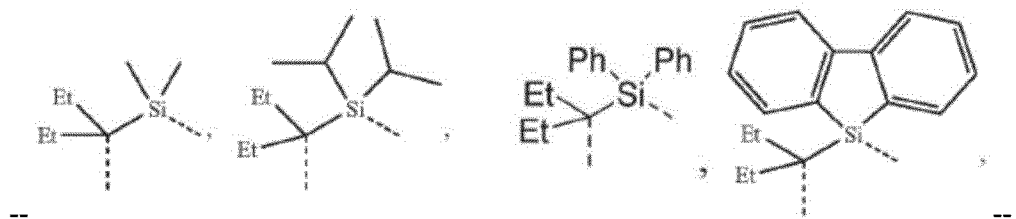

--                     ,                     ,                     ,                     --

In Claim 12, Column 168, Line 59, after structure L$_{A7}$, please insert:

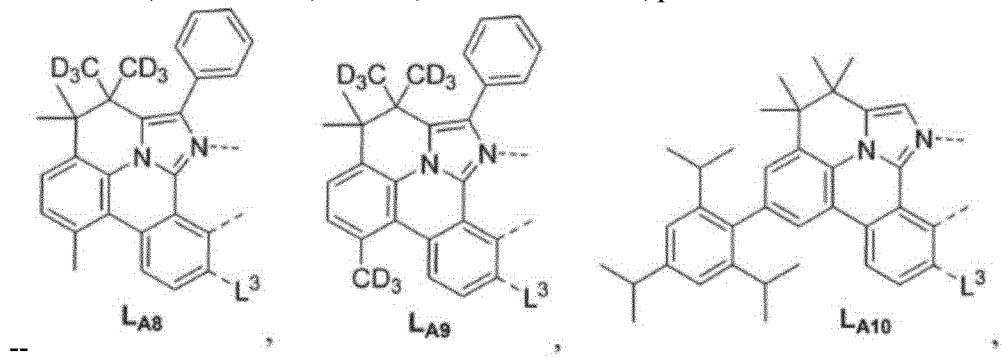

--                     ,                     ,                     ,                     --

Signed and Sealed this
Seventeenth Day of September, 2019

Andrei Iancu
*Director of the United States Patent and Trademark Office*

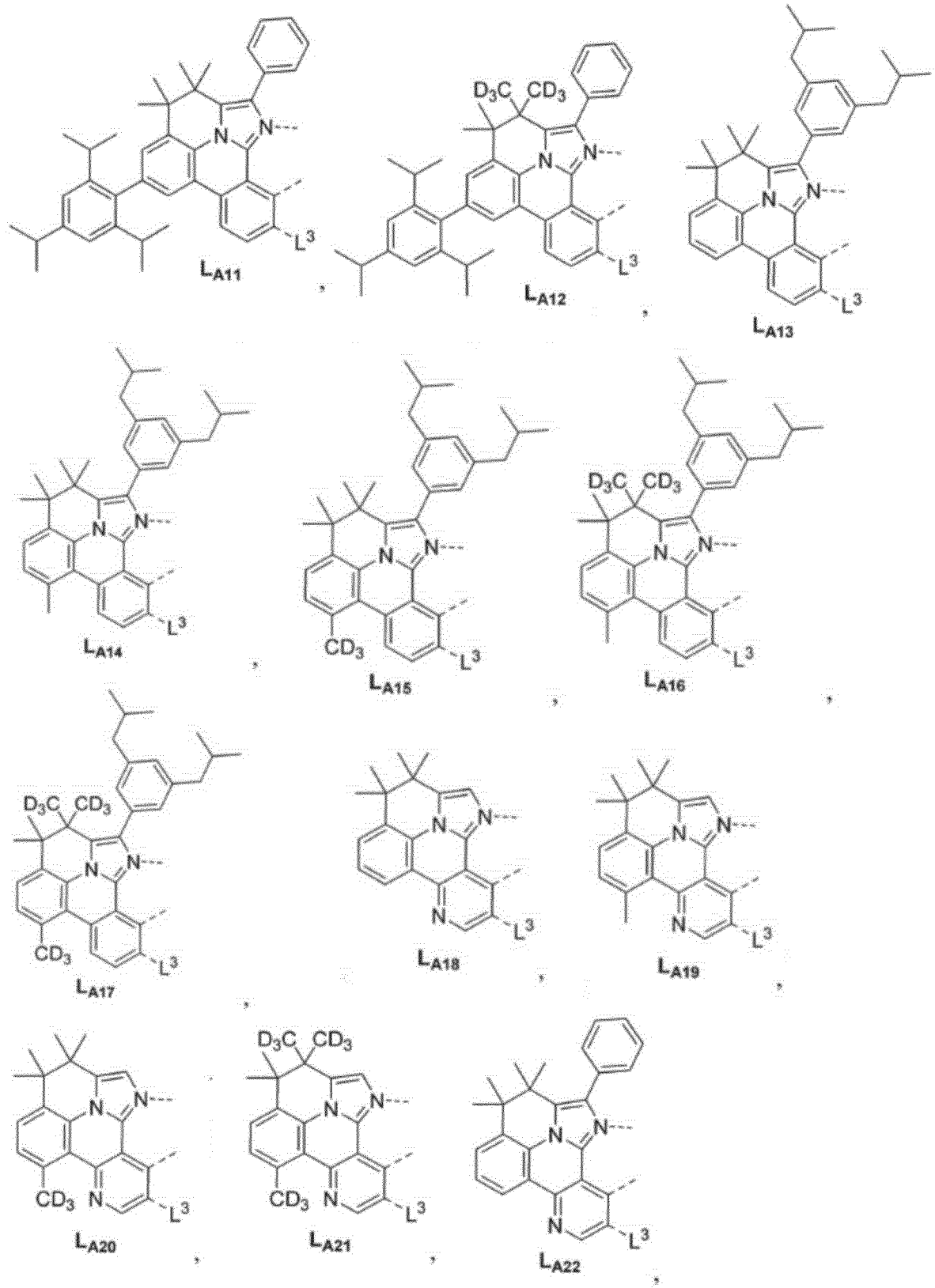

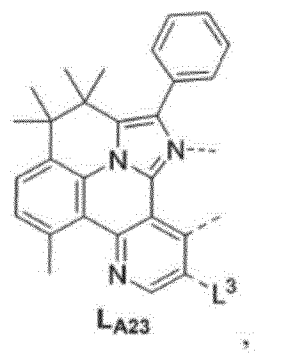 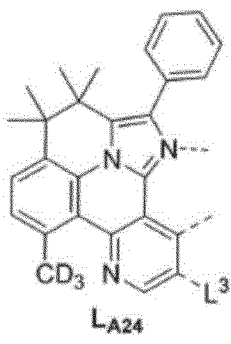 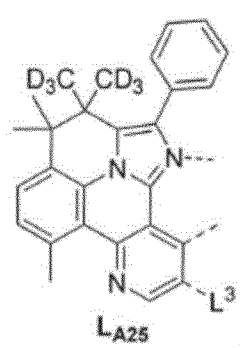
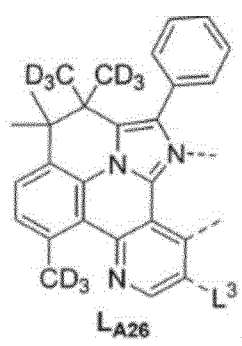 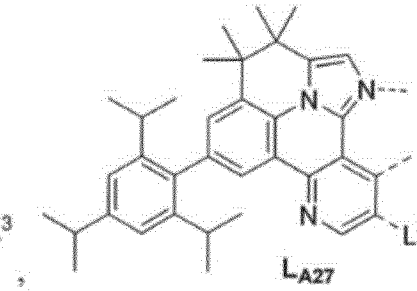 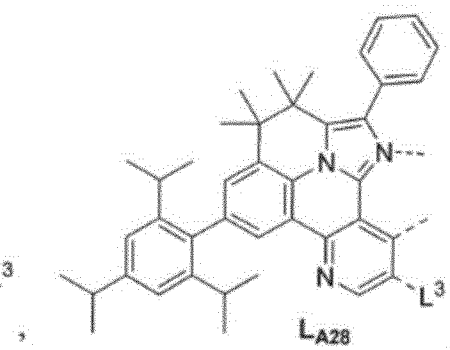
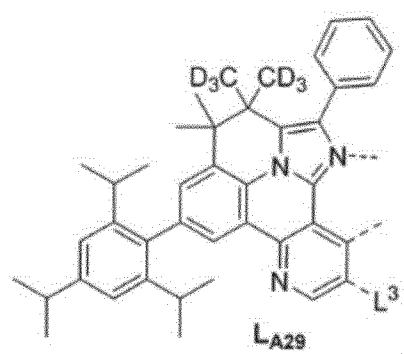 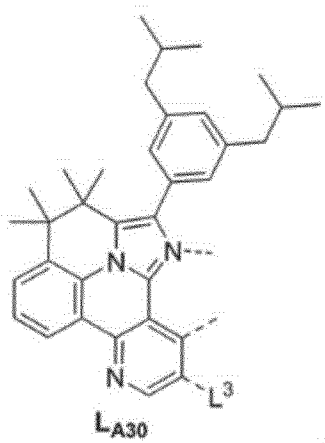 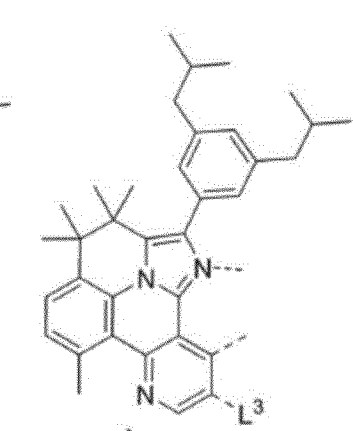

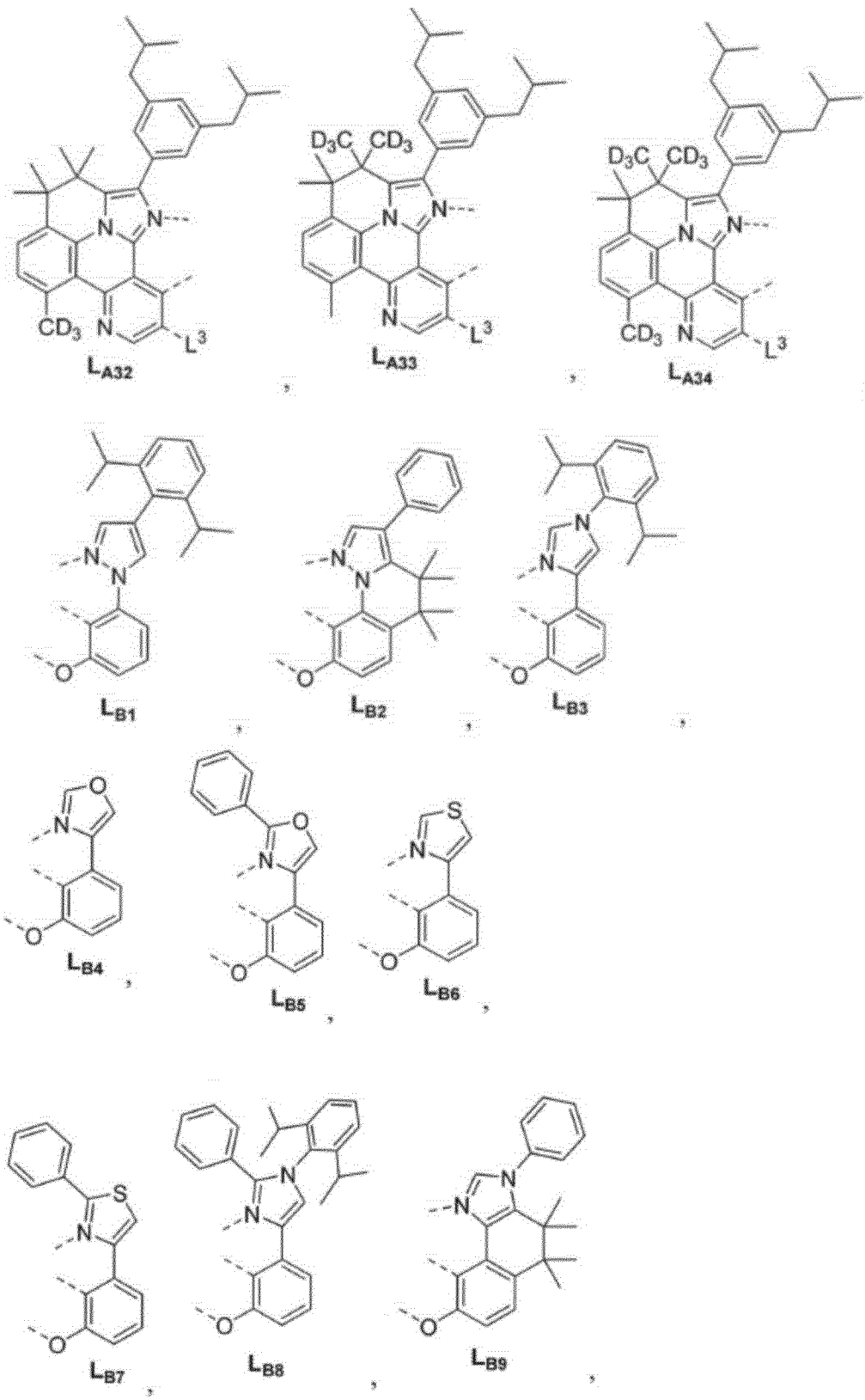

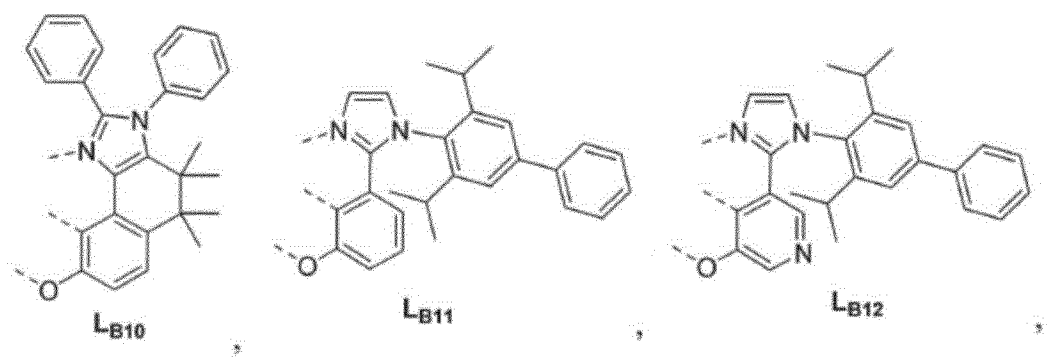
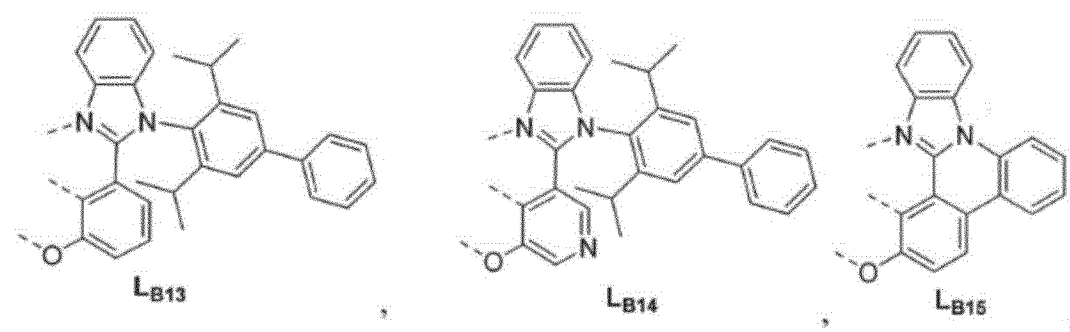
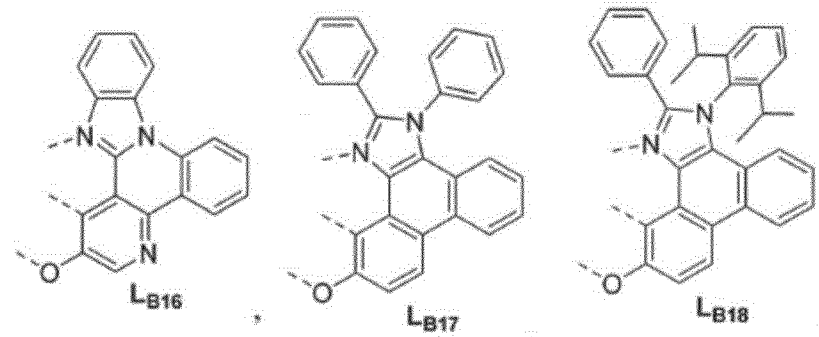
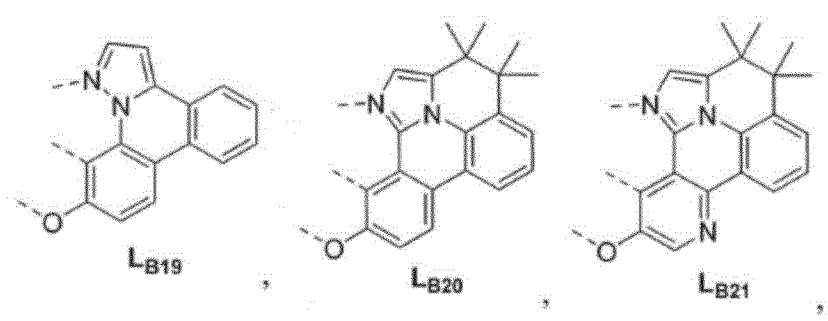

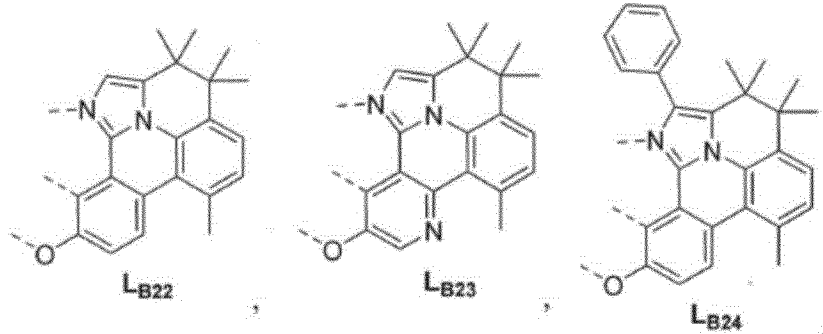
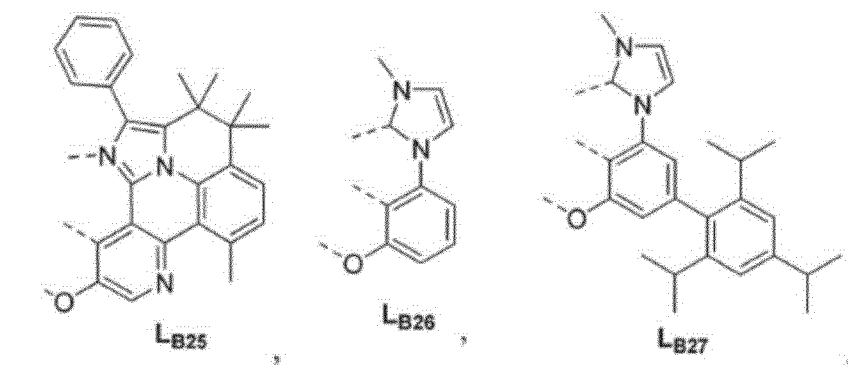
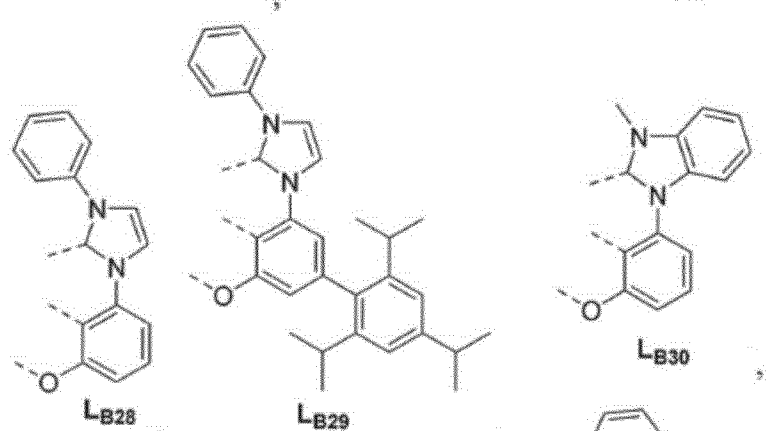
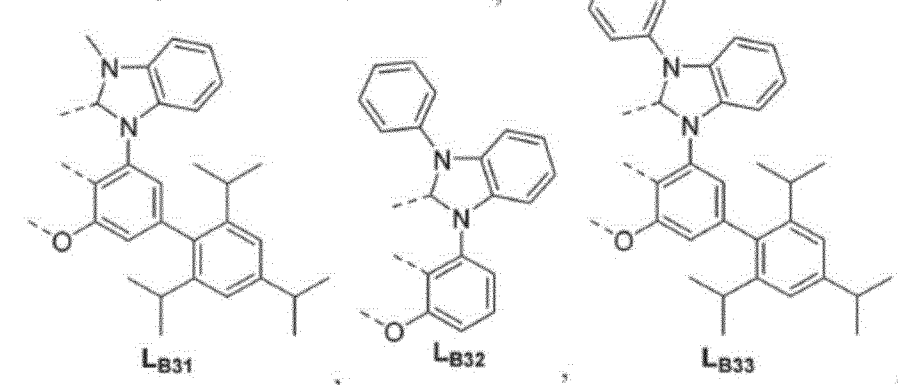

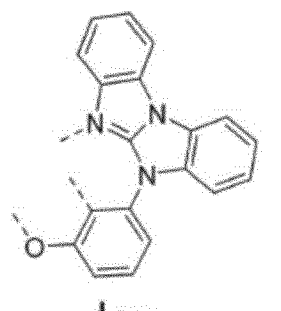 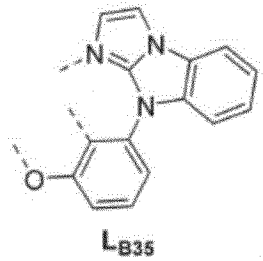 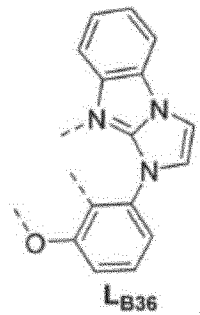
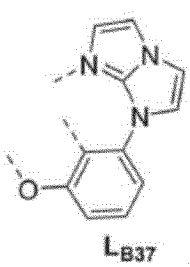 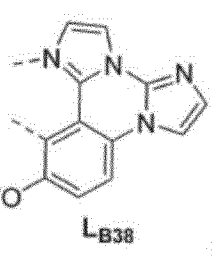 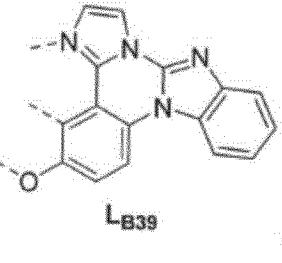
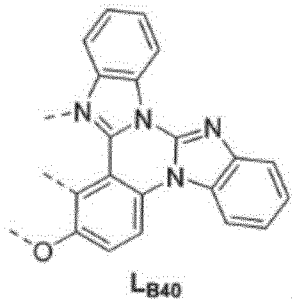 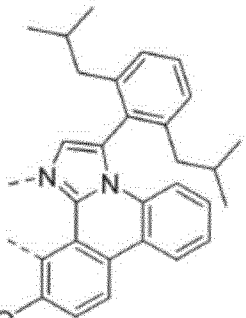 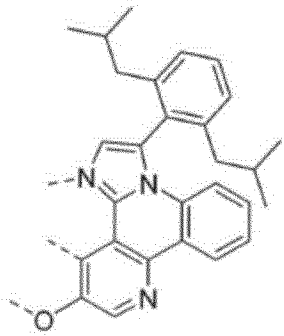
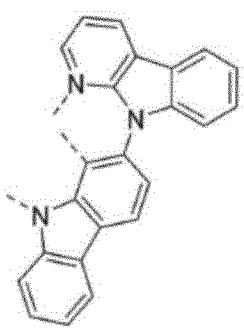 and 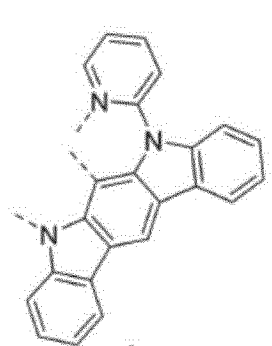 --